(12) United States Patent
Farmer

(10) Patent No.: US 9,394,326 B2
(45) Date of Patent: Jul. 19, 2016

(54) CATALYSTS AND METHODS FOR POLYMER SYNTHESIS

(75) Inventor: Jay J. Farmer, Ithaca, NY (US)

(73) Assignee: Novomer, Inc., Ithaca, NY (US)

( * ) Notice: Subject to any disclaimer, the term of this patent is extended or adjusted under 35 U.S.C. 154(b) by 0 days.

(21) Appl. No.: 14/237,447

(22) PCT Filed: Aug. 8, 2012

(86) PCT No.: PCT/US2012/049934
§ 371 (c)(1),
(2), (4) Date: Feb. 6, 2014

(87) PCT Pub. No.: WO2013/022932
PCT Pub. Date: Feb. 14, 2013

(65) Prior Publication Data
US 2014/0171617 A1 Jun. 19, 2014

Related U.S. Application Data

(60) Provisional application No. 61/521,065, filed on Aug. 8, 2011.

(51) Int. Cl.
| | |
|---|---|
| C08G 64/34 | (2006.01) |
| C07F 15/06 | (2006.01) |
| B01J 31/18 | (2006.01) |
| B01J 31/22 | (2006.01) |
| C07D 307/33 | (2006.01) |
| C08G 64/00 | (2006.01) |

(52) U.S. Cl.
CPC ............. *C07F 15/065* (2013.01); *B01J 31/182* (2013.01); *B01J 31/183* (2013.01); *B01J 31/1815* (2013.01); *B01J 31/1835* (2013.01); *B01J 31/2243* (2013.01); *C07D 307/33* (2013.01); *C08G 64/34* (2013.01); *B01J 2231/14* (2013.01); *B01J 2231/341* (2013.01); *B01J 2531/0216* (2013.01); *B01J 2531/0252* (2013.01); *B01J 2531/31* (2013.01); *B01J 2531/62* (2013.01); *B01J 2531/845* (2013.01)

(58) Field of Classification Search
CPC ........................................................ C08G 64/34
USPC .............. 528/405; 544/225; 548/106; 556/34
See application file for complete search history.

(56) References Cited

U.S. PATENT DOCUMENTS

| | | |
|---|---|---|
| 6,870,004 B1 | 3/2005 | Nguyen et al. |
| 7,304,172 B2 | 12/2007 | Coates et al. |
| 7,399,822 B2 | 7/2008 | Coates et al. |
| 7,674,873 B2 | 3/2010 | Coates et al. |
| 7,723,256 B2 | 5/2010 | Coates et al. |
| 8,278,239 B2 | 10/2012 | Coates et al. |
| 8,633,123 B2 | 1/2014 | Allen et al. |
| 8,946,109 B2 | 2/2015 | Allen et al. |
| 8,951,930 B2 | 2/2015 | Allen et al. |
| 8,956,989 B2 | 2/2015 | Allen et al. |
| 2003/0162961 A1 | 8/2003 | Coates et al. |
| 2006/0135743 A1 | 6/2006 | Park et al. |
| 2009/0227740 A1 | 9/2009 | Ying et al. |
| 2010/0121026 A1 | 5/2010 | Lee et al. |
| 2010/0234548 A1 | 9/2010 | Kolling et al. |
| 2011/0152497 A1 | 6/2011 | Allen et al. |
| 2015/0252145 A1 | 9/2015 | Allen et al. |

FOREIGN PATENT DOCUMENTS

| | | |
|---|---|---|
| CN | 101270112 A | 9/2008 |
| CN | 101974024 A | 2/2011 |
| WO | WO-2010/022388 A2 | 2/2010 |
| WO | WO-2010/033703 A1 | 3/2010 |

OTHER PUBLICATIONS

Fan, Q.-h. et al., Highly effective soluble polymer-supported catalysts for asymmetric hydrogenation, J. Am. Chem. Soc., 121: 7407-7408 (1999).
Nakano, K. et al., Selective formation of polycarbonate over cyclic carbonate: copolymerization of epoxides with carbon dioxide catalyzed by a cobalt(III) complex with a piperidinium end-capping arm, Angew. Chem. Int. Ed., 45(43): 7274-7277 (2006).
Qin, Z. et al., Cobalt-Based Complexes for the Copolymerization of Propylene Oxide and CO2: Active and Selective Catalysts for Polycarbonate Synthesis Angew. Chem. Int. Ed., 42(44): 5484-5487 (2003).
Ready, J.M. and Jacobsen E.N., Highly active oligomeric (salen)co catalysts for asymmetric epoxide ring-opening reactions, J. Am. Chem. Soc., 123: 2687-2688 (2001).
Wilen, S.H., et al., Strategies in Optical Resolutions, Tetrahedron 33: 2725-2736 (1977).
Yu et al., The First Optically Active BINOL-BINAP Copolymer Catalyst: Highly Stereoselective Tandem Asymmetric Reactions, J. Am. Chem., 122: 6500-6501 (2000).
International Search Report for PCT/US2012/049934 mailed Oct. 29, 2012.

*Primary Examiner* — Duc Truong
(74) *Attorney, Agent, or Firm* — Choate, Hall & Stewart LLP; Charles E. Lyon; John P. Rearick

(57) ABSTRACT

The present invention provides oligomeric metal complexes having more than one metal center and methods of using such complexes. The provided metal complexes are useful in the copolymerization of carbon dioxide and epoxides.

40 Claims, No Drawings

CATALYSTS AND METHODS FOR POLYMER SYNTHESIS

CROSS REFERENCE TO RELATED APPLICATIONS

The present application claims priority to U.S. provisional patent application Ser. No. 61/521,065, filed Aug. 8, 2011, the entire contents of which are hereby incorporated by reference.

BACKGROUND

Catalysts capable of effecting the copolymerization of epoxides and carbon dioxide to form aliphatic polycarbonates (APCs) have been known in the art since the 1960s. The early catalysts were based on heterogeneous zinc compounds and suffered from low reactivity, a lack of selectivity for polymer formation vs. cyclic carbonate formation, and a tendency to produce polycarbonates contaminated with ether linkages.

Improved catalysts based on transition metals have been discovered over the past decade or so. These newer catalysts have increased reactivity and improved selectivity. Nevertheless, even using highly active catalysts such as those disclosed in U.S. Pat. No. 7,304,172, the reaction times required to make high molecular weight polymer are typically quite long. In addition, the best-performing catalysts disclosed in the '172 patent require the addition of a separate co-catalyst to achieve optimum activity.

Attempts to address these shortcomings have been made. Catalysts described by Nozaki and co-workers (*Angew. Chem. Int. Ed.* 2006, 45, 7274-7277) tether an amine co-catalyst to a ligand of the catalyst. These next-generation catalytic systems suffer from lengthy and complicated syntheses and undesirable induction times prior to onset of polymerization. There remains a need for catalysts that have increased activity that will further reduce the polymerization time required to produce high molecular weight APCs.

SUMMARY

The present invention provides, among other things, metal complexes having more than one metal center and comprising a tethered activating moiety. The present invention also provides methods of using such complexes. In some embodiments, provided metal complexes have activity in the copolymerization of carbon dioxide and epoxides.

In certain embodiments, the present invention provides metal complexes and methods for using the same in the copolymerization of carbon dioxide and epoxides. In some embodiments, provided metal complexes have the structure:

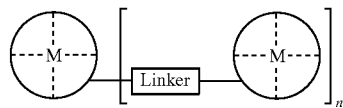

wherein M,

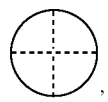

the linker, and n are as defined and described in classes and subclasses herein.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl. In certain embodiments, the term aliphatic group encompasses aliphatic groups wherein one or more hydrogen atoms are replaced with a halogen atom. In certain embodiments, the term aliphatic group encompasses chlorinated or fluorinated aliphatic groups including perfluorinated compounds.

The term "epoxide", as used herein, refers to a substituted or unsubstituted oxirane. Such substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic. In certain embodiments, the term "3- to 8-membered carbocycle" refers to a 3- to 8-membered saturated or partially unsaturated monocyclic carbocyclic ring The term "alkyl," as used herein, refers to saturated, straight- or branched-chain hydrocarbon radicals derived by removal of a single hydrogen atom from an aliphatic moiety. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived by the removal of a single hydrogen atom from a straight- or branched-chain aliphatic moiety having at least one carbon-carbon double bond. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, allyl, 1,3-butadienyl, butenyl, 1-methyl-2-buten-1-yl, allyl, 1,3-butadienyl, allenyl, and the like.

The term "alkynyl," as used herein, refers to a monovalent group derived by the removal of a single hydrogen atom from a straight- or branched-chain aliphatic moiety having at least one carbon-carbon triple bond. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refer to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, and spiro[4.5]decane, to name but a few.

The term "aryl" used alone or as part of a larger moiety as in "aralkyl", "aralkoxy", or "aryloxyalkyl", refers to monocyclic and polycyclic ring systems having a total of six to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the term "8- to 14-membered aryl" refers to an 8- to 14-membered polycyclic aryl ring.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one to six carbon atoms are independently replaced by one or more of oxygen, sulfur, nitrogen, or phosphorus. Heteroaliphatic groups may be substituted or unsubstituted, branched or unbranched, cyclic or acyclic, and include saturated, unsaturated or partially unsaturated groups.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or polycyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 14-membered heteroaryl" refers to a 5- to 6-membered monocyclic heteroaryl ring having 1 to 3 heteroatoms independently selected from nitrogen, oxygen, or sulfur, or an 8- to 14-membered bicyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is saturated, partially unsaturated, or aromatic and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 7-membered heterocyclic" refers to a 3- to 7-membered saturated or partially unsaturated monocyclic heterocyclic ring having 1 to 2 heteroatoms independently selected from nitrogen, oxygen, or sulfur. In some embodiments, the term "3- to 8-membered heterocyclic" refers to a 3- to 8-membered saturated or partially unsaturated monocyclic heterocyclic ring having 1 to 2 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "acyl" as used herein refers to a group having a formula —C(O)R where R is hydrogen or an optionally substituted aliphatic, aryl, or heterocyclic group.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy) methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protecting Groups in Organic Synthesis*, T. W. Greene and P. G. M. Wuts, 3$^{rd}$ edition, John Wiley & Sons, 1999, the entirety of which is incorporated herein by reference.

When substituents are described herein, the term "radical" or "optionally substituted radical" is sometimes used. In this context, "radical" means a moiety or functional group having an available position for attachment to the structure on which the substituent is bound. In general the point of attachment would bear a hydrogen atom if the substituent were an independent neutral molecule rather than a substituent. The terms "radical" or "optionally-substituted radical" in this context are thus interchangeable with "group" or "optionally-substituted group".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted group" or "optionally substituted radical" may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond that crosses a bond in a ring of the depicted molecule. This convention indicates that one or more of the substituents may be attached to the ring at any available position (usually in place of a hydrogen atom of the parent structure). In cases where an atom of a ring so substituted has two substitutable positions, two groups may be present on the same ring atom. Unless otherwise indicated, when more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}$Ph, which may be substituted with R°; —$(CH_2)_{0-4}O(CH_2)_{0-1}$Ph which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$;

—OP(O)R°$_2$; —OP(O)(OR°)$_2$; SiR°$_3$; —(C$_{1-4}$ straight or branched) alkylene)O—N(R°)$_2$; or —(C$_{1-4}$ straight or branched)alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-4}$C(O)N(R°)$_2$; —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●_2$, —NO$_2$, —SiR$^●_3$, —OSiR$^●_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with intervening atom(s) form an unsubstituted 3-12-membered saturated, partially unsaturated, or aryl mono- or bicyclic ring having 0-4 heteroatoms independently selected from nitrogen, oxygen, or sulfur. A substitutable nitrogen may be substituted with three R$^†$ substituents to provide a charged ammonium moiety —N$^+$(R$^†$)$_3$, wherein the ammonium moiety is further complexed with a suitable counterion.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "catalyst" refers to a substance the presence of which increases the rate and/or extent of a chemical reaction, while not being consumed or undergoing a permanent chemical change itself.

As used herein, the term "multidentate" refers to ligands having multiple sites capable of coordinating to a single metal center.

As used herein, the term "activating moiety" refers to a moiety comprising one or more activating functional groups. In certain embodiments, an activating moiety improves the catalytic activity of a metal complex. In some embodiments, such improved catalytic activity is characterized by higher conversion of starting materials compared to a metal complex lacking an activating moiety. In some embodiments, such improved catalytic activity is characterized by higher rate of conversion of starting materials compared to a metal complex lacking an activating moiety. In some embodiments, such improved catalytic activity is characterized by higher yield of product compared to a metal complex lacking an activating moiety.

DETAILED DESCRIPTION OF CERTAIN EMBODIMENTS

The present invention encompasses the recognition that there remains a need for metal complexes useful in the copolymerization of epoxides and carbon dioxide. Metal complexes provided by the present invention can show significant advantages for uses in the copolymerization of epoxides and carbon dioxide. While not wishing to be bound by any particular theory, it is believed that metal complexes of the present invention provide enhanced reactivity and/or selectivity when compared to known metal complexes. In certain embodiments, a provided metal complex is highly selective for a copolymerization reaction, resulting in little or no cyclic carbonate formation. In certain embodiments, a provided metal complex is highly selective for polycarbonate formation.

The present invention provides, among other things, metal complexes for the copolymerization of carbon dioxide and epoxides and methods of using the same. In certain embodiments, provided metal complexes contain two or more metal atoms. In certain embodiments, the metal atoms are complexed to ligands connected by a linker moiety, and at least one activating moiety is tethered to the metal complex. In some embodiments, an activating moiety comprises one or more activating functional groups. In certain embodiments, at least one activating functional group present on the tethered moiety can act as a polymerization co-catalyst and thereby increase the rate of the copolymerization. In some embodiments, provided metal complexes act as polymerization catalysts.

I. Metal Complexes

In certain embodiments, the present invention provides oligomeric metal complexes and methods for using the same in the copolymerization of carbon dioxide and epoxides. In some embodiments, provided metal complexes have a structure D-1:

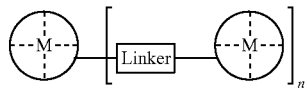

wherein:
each M is independently a metal atom;
each

is independently a multidentate ligand;
each linker is independently an optionally substituted $C_{2-30}$ aliphatic group wherein one or more carbons are optionally and independently replaced by -Cy-, —$NR^y$—, —$N(R^y)C(O)$—, —$C(O)N(R^y)$—, —$N(R^y)C(O)O$—, —$OC(O)N(R^y)$—, —$N(R^y)C(O)$ $N(R^y)$—, —$OC(O)O$—, —O—, —$C(O)$—, —$OC(O)$—, —$C(O)O$—, —S—, —$Si(R^y)_2$—, —SO—, —$SO_2$—, —$C(=S)$—, —$C(=NR^y)$—, or —N=N—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-12 membered bivalent saturated, partially unsaturated, or aryl bicyclic ring having 0-5 heteroatoms independently selected from nitrogen, oxygen, or sulfur; and
  each $R^y$ is independently —H, or an optionally substituted radical selected from the group consisting of $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, a 5-6 membered heteroaryl ring having 1-3 heteroatoms independently selected from nitrogen, oxygen, or sulfur, and 8- to 10-membered aryl; and
n is from 1 to 50;
wherein the oligomeric complex comprises one or more activating groups

where ⸺ is a tethering moiety covalently coupled to the ligand system, m is an integer from 1 to 4 representing the number of Z groups present on an individual tether moiety; and each Z is independently an activating functional group;

and wherein the repeating units of n are optionally joined to form a cyclic oligomeric complex.

In certain embodiments, $R^y$ is not H. In certain embodiments, $R^y$ is, independently at each occurrence an optionally substituted moiety selected from the group consisting of: $C_{1-6}$ aliphatic and phenyl.

In certain embodiments, provided metal complexes have a structure selected from formula D-II, D-III, or D-IV:

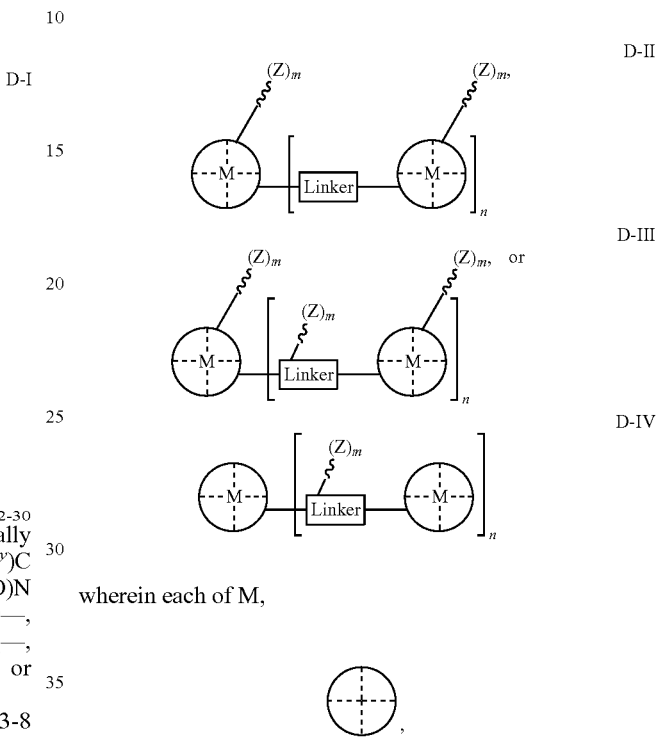

wherein each of M,

the linker, Z, m, and n is as defined above and described in classes and subclasses herein, both singly and in combination.

It will be appreciated that the n bracketed portion of metal complexes of formulae D-I, D-II, D-III, and D-IV, when n is greater than 1, are repeated to form oligomeric complexes. For example, formula D-IV having an n of 3 will be understood to be:

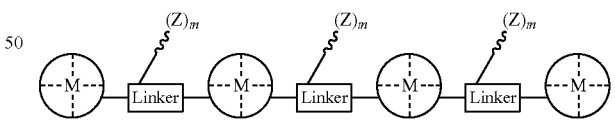

wherein each of M, m, Z, and the linker is as defined above and described in classes and subclasses herein, both singly and in combination.

In some embodiments, each linker is independently an optionally substituted $C_{2-20}$ aliphatic group wherein one or more carbons are optionally and independently replaced by -Cy-, —$NR^y$—, —$N(R^y)C(O)$—, —$C(O)N(R^y)$—, —$N(R^y)C(O)O$—, —$OC(O)N(R^y)$—, —$N(R^y)C(O)$ $N(R^y)$—, —$OC(O)O$—, —O—, —$C(O)$—, —$OC(O)$—, —$C(O)O$—, —S—, —$Si(R^y)_2$—, —SO—, —$SO_2$—, —$C(=S)$—, —$C(=NR^y)$—, or —N=N—. In some embodiments, each linker is independently an optionally substituted $C_{2-20}$ aliphatic group wherein one or more carbons are optionally and independently replaced by -Cy-, —O—, —C(O)—, —S—, —Si(R$^y$)$_2$—, —SO—, or —SO$_2$—. In some embodiments, each linker is independently an optionally substituted C$_{2-10}$ aliphatic group wherein one or more carbons are optionally and independently replaced by -Cy-, —NR$^y$—, —N(R$^y$)C(O)—, —C(O)N(R$^y$)—, —N(R$^y$)C(O)O—, —OC(O)N(R$^y$)—, —N(R$^y$)C(O)N(R$^y$)—, —OC(O)O—, —O—, —C(O)—, —OC(O)—, —C(O)O—, —S—, —Si(R$^y$)$_2$—, —SO—, —SO$_2$—, —C(=S)—, —C(=NR$^y$)—, or —N=N—. In some embodiments, each linker is independently an optionally substituted C$_{2-10}$ aliphatic group wherein one, two, three, or four carbons are optionally and independently replaced by -Cy-, —NR$^y$—, —N(R$^y$)C(O)—, —C(O)N(R$^y$)—, —O—, —C(O)—, —OC(O)—, —C(O)O—, —S—, —Si(R$^y$)$_2$—, —SO—, —SO$_2$—, —C(=S)—, —C(=NR$^y$)—, or —N=N—. In some embodiments, each linker is independently an optionally substituted C$_{2-10}$ aliphatic group wherein one, two, three, or four carbons are optionally and independently replaced by —O—, —C(O)—, —OC(O)—, —C(O)O—, —OC(O)O—, —S—, —Si(R$^y$)$_2$—, —SO—, or —SO$_2$—.

In some embodiments, a linker is a C$_{2-10}$ straight or branched, saturated or unsaturated hydrocarbon chain optionally substituted with one or more halogen atoms, wherein two, three, or four methylene are replaced by —O—, —C(O)—, —OC(O)—, —C(O)O— or —OC(O)O—.

In some embodiments, a linker is a polyether chain. In certain embodiments, a linker comprises a polyalkylene glycol. In certain embodiments a polyalkylene glycol is selected from polyethylene glycol and polypropylene glycol. In certain embodiments, such polyethers comprise from 2 to about 20 repeating units. In certain embodiments, such polyethers comprise from 2 to about 10 repeating units. In certain embodiments, such polyethers comprise from 2 to 5 repeating units.

In some embodiments, a linker is selected based on the desired synthetic step to be employed in oligomerizing the metal complexes. Suitable synthetic steps for oligomerization include, but are not limited to: ester formation, ether formation, amide formation, urethane formation, urea formation, triazole formation, olefin metathesis and the like.

In the case of ester formation, a metal complex bearing a hydroxyl moiety on each aryl ring may be subjected to esterification conditions in the presence of a diacid. Alternatively, a metal complex bearing a carboxylic acid moiety on each aryl ring may be subjected to esterification conditions in the presence of a diol. In either of these cases, the linker will then comprise at least two ester groups as well as the carbon skeleton of the diacid diol used for the coupling. Alternatively, metal complexes bearing both an acid and a hydroxyl group can be subjected to esterification. Many suitable diols and diacids are commercially available including both aromatic and aliphatic compounds as well as hydroxy- and carboxy-terminated polymers, any of these may be employed to provide complexes of the present invention. Suitable diols, diacids and esterification conditions will be readily apparent to the skilled artisan. In other embodiments, thioether formation is used, for example by coupling a metal complex bearing a thiol moiety on each aryl ring with a bis-maleimide. The schemes below show several suitable approaches:

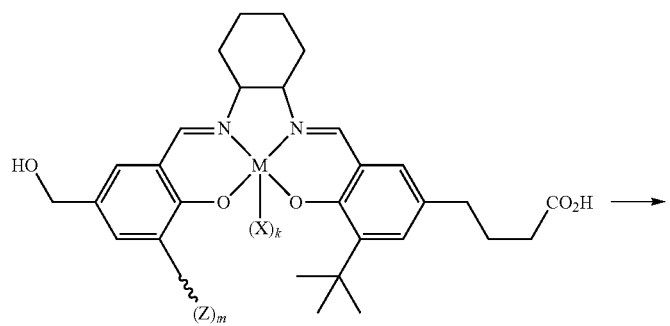

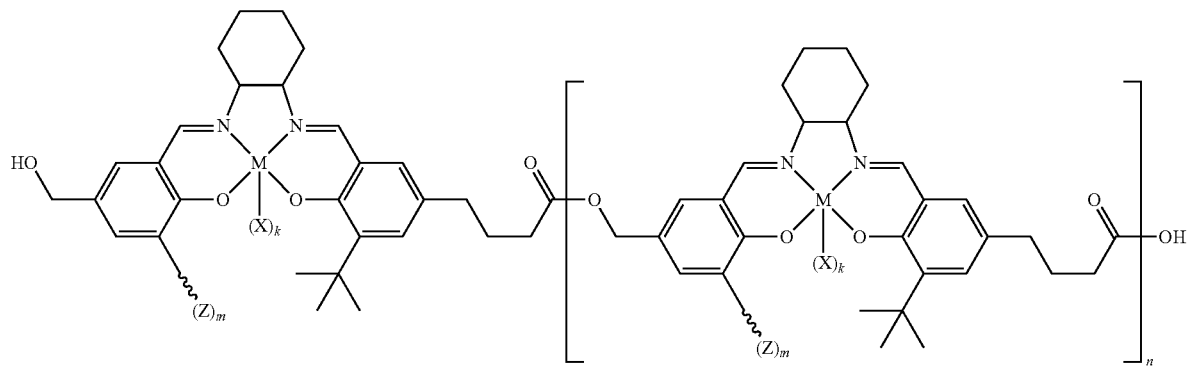

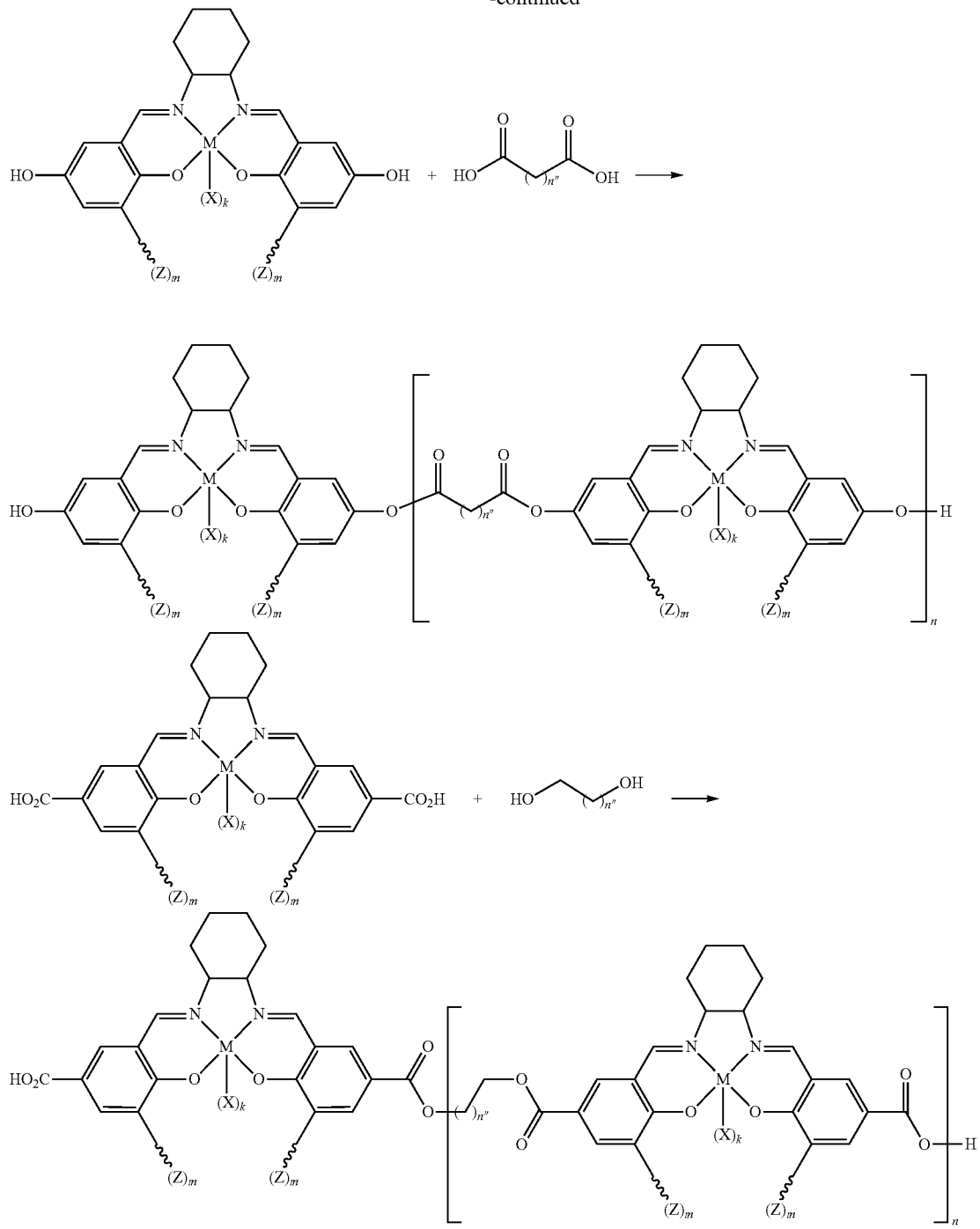

wherein each n″ is independently from 0-30 and each carbon comprising an n″ bracketed group may be optionally substituted, and M, X, k, and k, and —ᴧᴧᴧ(Z)$_m$ are defined below and in the classes and subclasses herein. In alternative approaches, the bracketed groups —(CH$_2$)$_{n''}$— in the schemes above may be substituted for an optionally substituted aryl ring, a heterocycle, a heteroaliphatic group, a polymer, etc.

In another embodiment, the oligomerization of the metal complexes may be effected by treating a metal complex bearing a hydroxyl moiety on each aryl ring with a diisocyanate. In this case, the linker will comprise two urethane moieties in addition to the carbon skeleton of the selected diisocyanate. In a related embodiment, the oligomerization may be accomplished by treating a metal complex bearing a secondary amine moiety on each aryl ring with a diisocyanate. In this instance, the linker moiety will comprise two urea moieties in addition to the carbon chain of the diisocycanate. Many suitable diisocyanates are commercially available including both aromatic and aliphatic diisocyanates as well as isocyanate-terminated polymers, and any of these may be employed to provide complexes of the present invention. The schemes below show several suitable approaches:

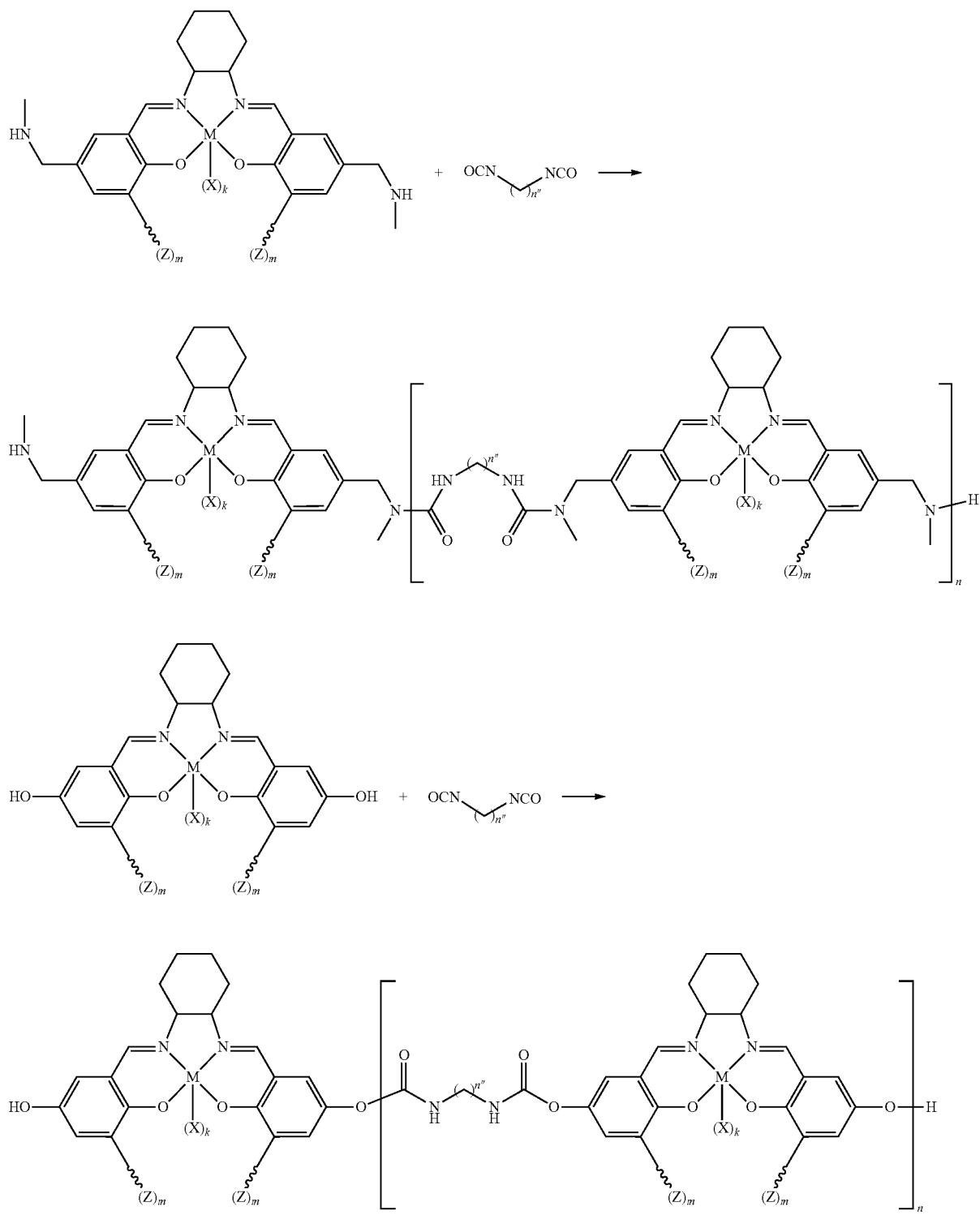

wherein each n" is independently from 0-30 and each carbon comprising an n" bracketed group may be optionally substituted, and M, X, k, and ─ⁿⁿⁿ(Z)$_m$ are defined below and in the classes and subclasses herein. In alternative approaches, the bracketed groups ─(CH$_2$)$_{n''}$ in the schemes above may be substituted for an optionally substituted aryl ring, a heterocycle, a heteroaliphatic group, a polymer, etc.

ikewise, if a metal complex bearing an olefin on both aryl rings is treated to olefin metathesis conditions (either alone or in the presence of additional dienes), the linker will comprise a double bond as well as other carbon atoms from the alkene groups and/or the optionally provided diene.

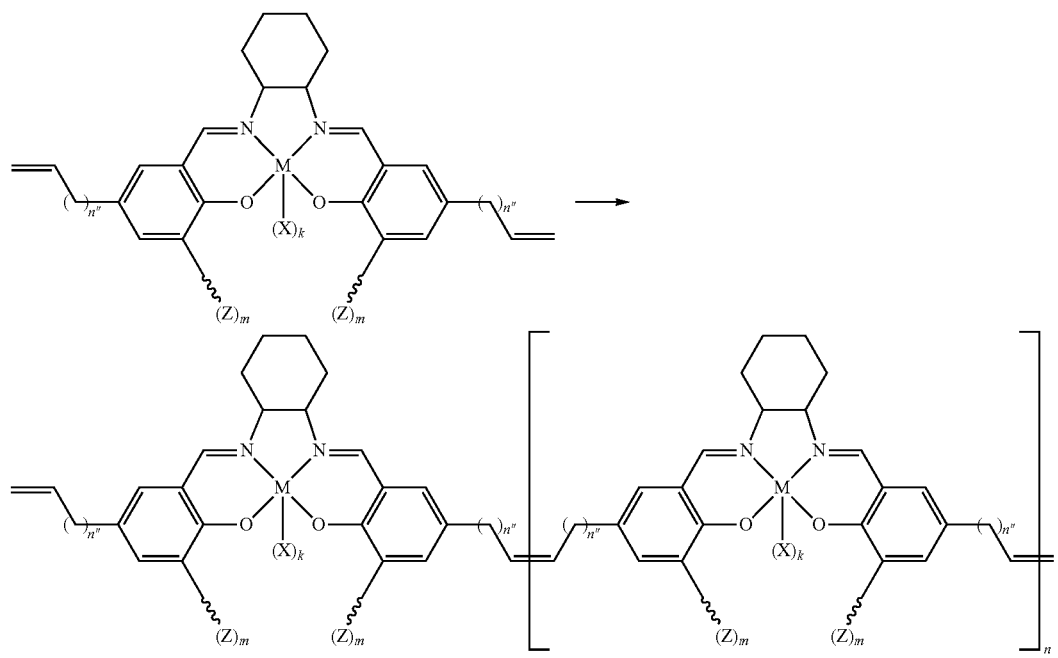

wherein each n″ is independently from 0-30 and each carbon comprising an n″ bracketed group may be optionally substituted, and M, X, k, and —⁓(Z)$_m$ are defined below and in the classes and subclasses herein. In alternative approaches, the bracketed groups —(CH$_2$)$_{n''}$ in the schemes above may be substituted for an optionally substituted aryl ring, a heterocycle, a heteroaliphatic group, a polymer, etc.

If a metal complex bearing an azide on one ring and an alkyne on the other, the linker will comprise a triazole as well as other carbon atoms from the linker. Alternatively, a diazide, or diyne may be reacted with metal complexes bearing two alkyne groups or two azide groups respectively. This chemistry may be catalyzed by copper (I) salts or using other methods known in the art, including copper-free methods. For example, here is one embodiment of the first approach:

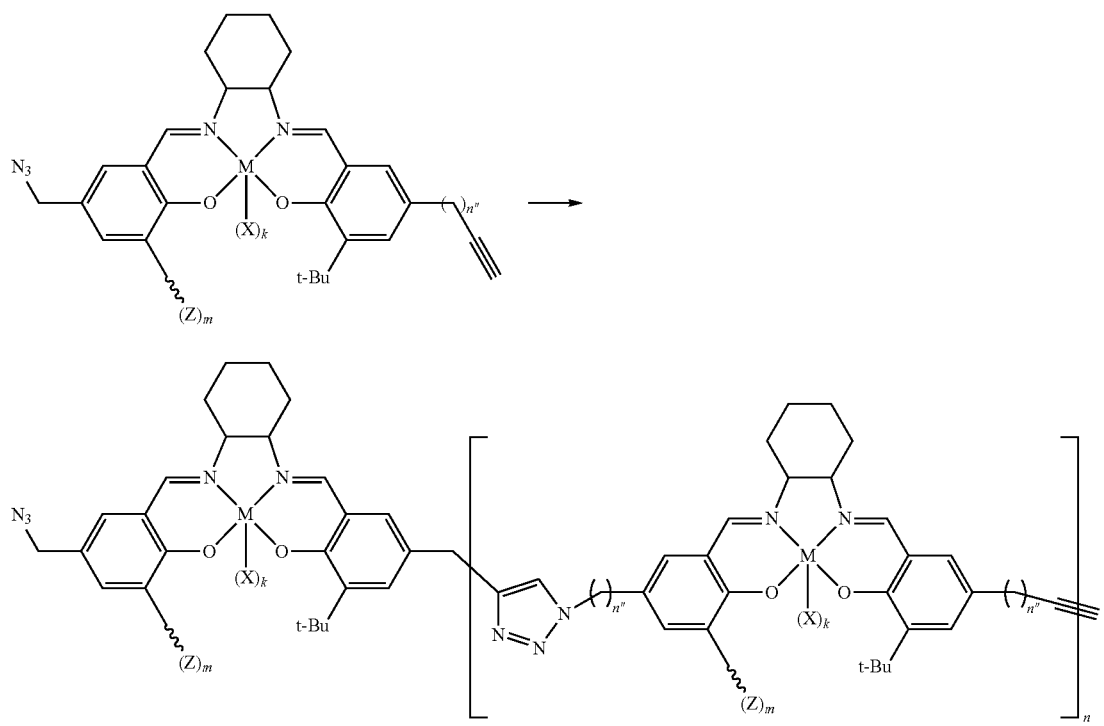

wherein each n" is independently from 0-30 and each carbon comprising an n" bracketed group may be optionally substituted, and M, X, k, and —〰(Z)$_m$ are defined below and in the classes and subclasses herein. In alternative approaches, the bracketed groups —(CH$_2$)$_{n''}$ in the schemes above may be substituted for an optionally substituted aryl ring, a heterocycle, a heteroaliphatic group, a polymer, etc.

In some embodiments, a linker is or comprises an activating group as described in classes and subclasses herein. In some embodiments, -Cy- is or comprises a cyclic activating group as described in classes and subclasses herein. For example, in certain embodiments, -Cy- is a bivalent 8-12 membered saturated or partially unsaturated bicyclic ring having 0-5 heteroatoms independently selected from nitrogen, oxygen, or sulfur. In some embodiments, -Cy- is selected from:

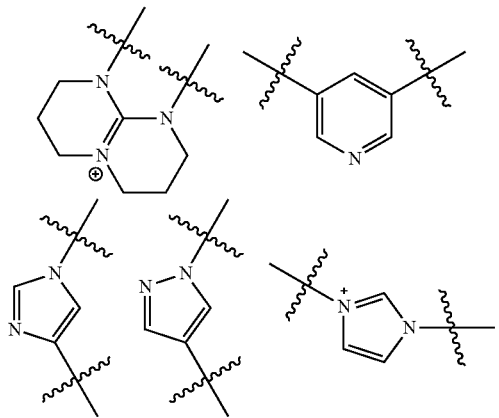

In some embodiments, n is from 1 to 40. In some embodiments, n is from 2 to 50. In some embodiments, n is from 10 to 40. In some embodiments, n is from 1 to 30. In some embodiments, n is from 1 to 20. In some embodiments, n is from 1 to 10. In some embodiments, n is from 2 to 10. In some embodiments, n is from 2 to 6. In some embodiments, n is from 1 to 8. In some embodiments, n is from 1 to 7. In some embodiments, n is from 1 to 6. In some embodiments, n is from 1 to 5. In some embodiments, n is from 1 to 4. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, for provided metal complexes each

comprises:

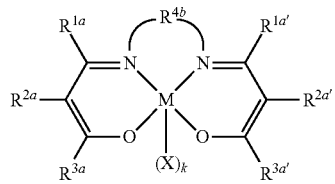

wherein M is as defined above and described in classes and subclasses herein, $R^{1a}$ and $R^{1a'}$, are independently a —〰(Z)$_m$ group, a linker, hydrogen, or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle; a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

$R^{2a}$, $R^{2a'}$, $R^{3a}$, and $R^{3a'}$ are independently a —〰(Z)$_m$ group, a linker, hydrogen, —OR, —NR$_2$, —SR, —CN, —NO$_2$, —OC(O)R, —CO$_2$R, —NRC(O)R, —C(O)NR$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where any of [$R^{2a'}$ and $R^{3a'}$], [$R^{2a}$ and $R^{3a}$], [$R^{1a}$ and $R^{2a}$], and [$R^{1a'}$ and $R^{2a'}$] may optionally be taken together with intervening atoms to form one or more rings which may in turn be substituted with one or more $R^d$ groups;

$R^{4b}$ is selected from the group consisting of:

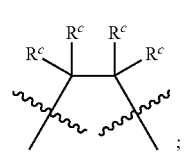
a)

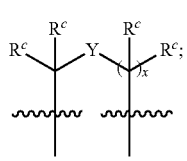
b)

-continued

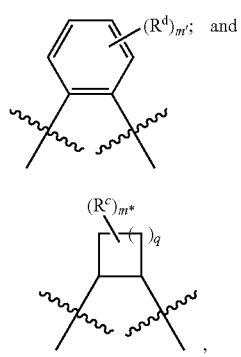

where
R$^c$ at each occurrence is independently a —ᴧᴧ(Z)$_m$ in group, a linker, hydrogen, halogen, —OR, —NR$_2$, —SR, —CN, —NO$_2$, —OC(O)R, —CO$_2$R, —NRC(O)R, —C(O)NR$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more R$^c$ groups may be taken together with the carbon atoms to which they are attached and any intervening atoms to form one or more optionally substituted rings; when two R$^c$ groups are attached to the same carbon atom, they may optionally be taken together along with the carbon atom to which they are attached to form an optionally substituted moiety selected from the group consisting of: an alkene, a 3- to 8-membered spirocyclic ring, a carbonyl, an oxime, a hydrazone, and an imine;

R$^d$ at each occurrence is independently a —ᴧᴧ(Z)$_m$ group, a linker, a portion of a linker that is connected to another oligomeric unit, a moiety capable of forming a linker, hydrogen, halogen, —OR, —NR$_2$, —SR, —CN, —NO$_2$, —OC(O)R, —CO$_2$R, —NRC(O)R, —C(O)NR$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more R$^d$ groups may be taken together with intervening atoms to form one or more optionally substituted rings optionally containing one or more heteroatoms, R at each occurrence is independently hydrogen, an optionally substituted radical selected the group consisting of acyl; C$_{1-6}$ aliphatic; C$_{1-6}$ heteroaliphatic; carbamoyl; arylalkyl; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring, each X is an independently an anion;

Y is a divalent linker selected from the group consisting of: —NR—, —N(R)C(O)—, —C(O)NR—, —O—, —C(O)—, —OC(O)—, —C(O)O—, —OC(O)O—, —S—, —SO—, —SO$_2$—, —SiR$_2$—, —C(=S)—, —C(=NR)—, or —(R$^c$)C=C(R$^c$)—; —N=N—; a polyether; a C$_3$ to C$_8$ substituted or unsubstituted carbocycle; and a C$_1$ to C$_8$ substituted or unsubstituted heterocycle;

k is 0, 1, or 2;

m* is 0 or an integer from 1 to 6, inclusive;

m' is 0 or an integer from 1 to 4, inclusive;

q is 0 or an integer from 1 to 4, inclusive; and x is 0, 1, or 2.

In certain embodiments of provided metal complexes,

comprises:

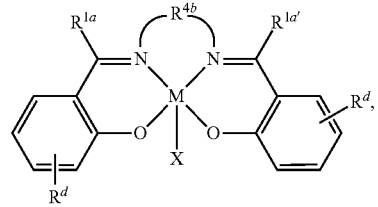

wherein each of M, R$^{1a}$, R$^{1a'}$, R$^{4b}$, R$^d$, and X is as defined above and in classes and subclasses herein, both singly and in combination.

It will be appreciated that where a ring is depicted herein with a single R$^d$ group at an unspecified position, such as:

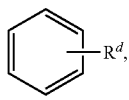

more than a single $R^d$ group may be present, up to the maximum number allowed by valency rules.

In certain embodiments of provided metal complexes,

comprises:

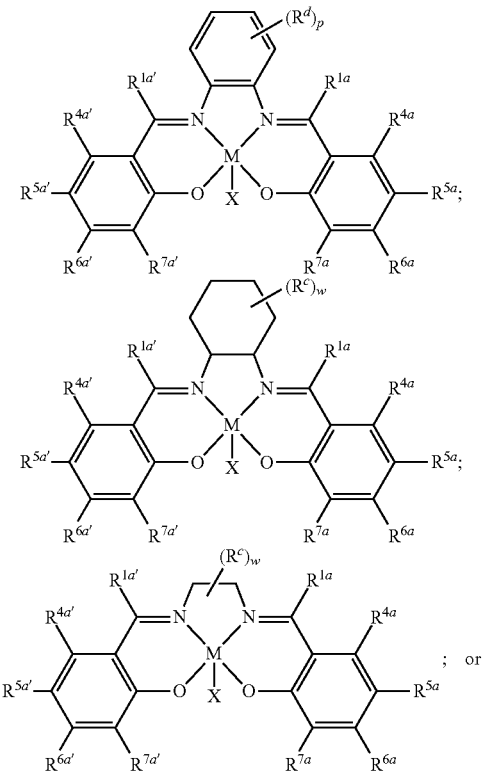

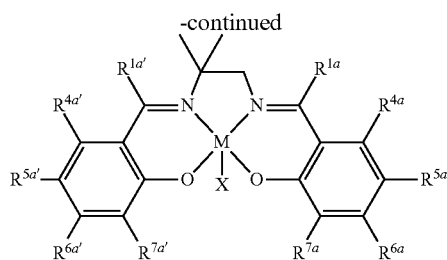

wherein each of $R^{1a}$, $R^{1a'}$, $R^c$, $R^d$, M, m and X is as defined above and described in classes and subclasses herein;

$R^{4a}$, $R^{4a'}$, $R^{5a}$, $R^{5a'}$, $R^{6a}$, $R^{6a'}$, $R^{7a}$, and $R^{7a'}$ are each independently a —⁓$(Z)_m$ group, a linker, hydrogen, halogen, —OR, —NR$_2$, —SR, —CN, —NO$_2$, —OC(O)R, —CO$_2$R, —NRC(O)R, —C(O)NR$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where [$R^1$ and $R^4$], [$R^{1'}$ and $R^{4a'}$] and any two or more adjacent $R^{4a}$, $R^{4a'}$, $R^{5a}$, $R^{5a'}$, $R^{6a}$, $R^{6a'}$, $R^{7a}$, and $R^{7a'}$ groups can optionally be taken together with intervening atoms to form one or more optionally substituted rings;

w is 0 or an integer from 1 to 8, inclusive; and p is 0 or an integer from 1 to 4, inclusive.

In certain embodiments, provided metal complexes are selected from the group consisting of:

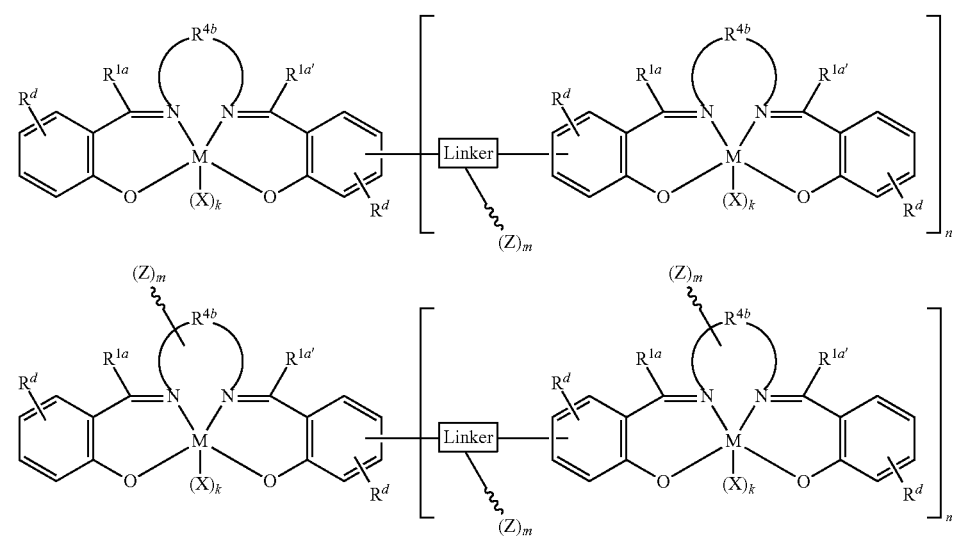

-continued
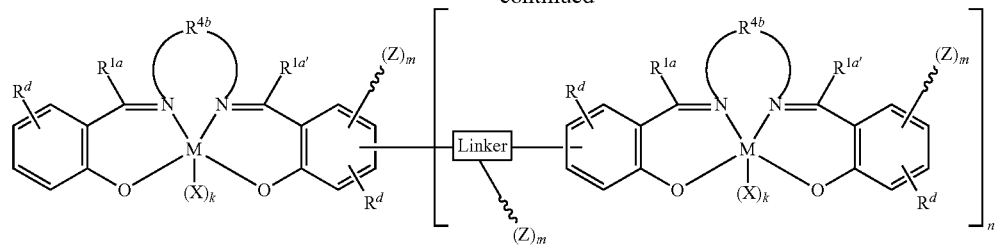
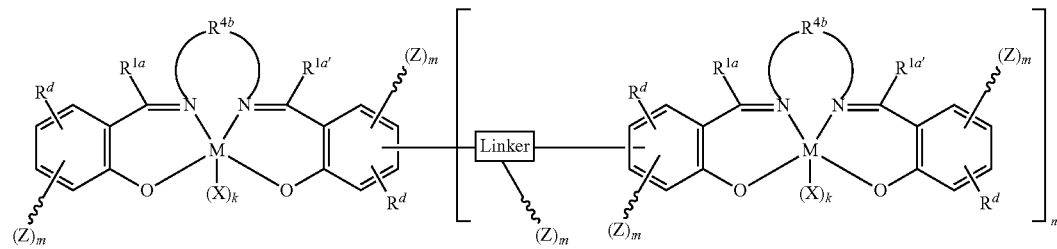
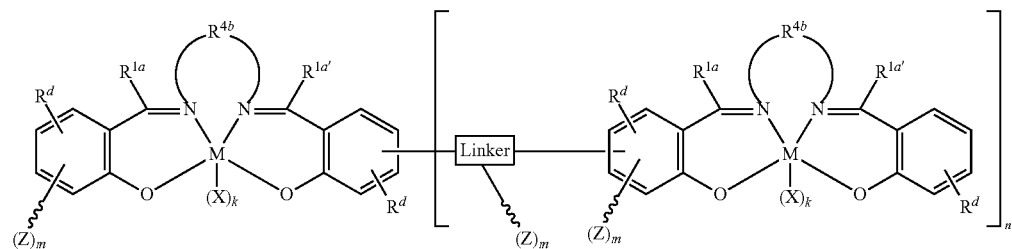
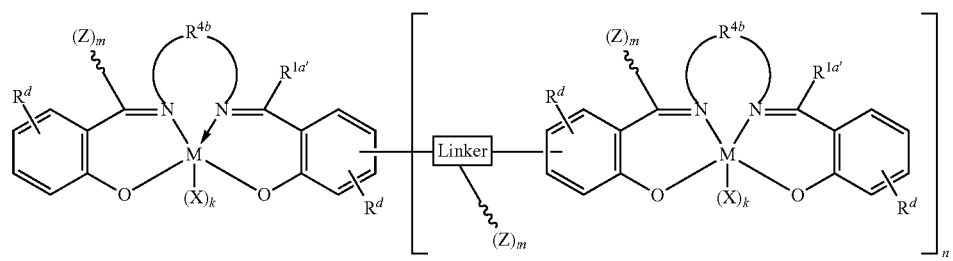
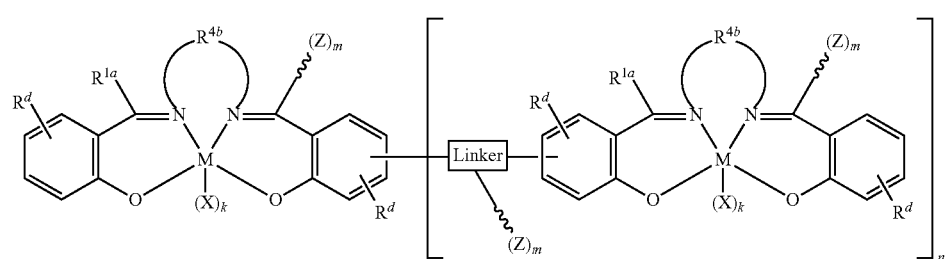
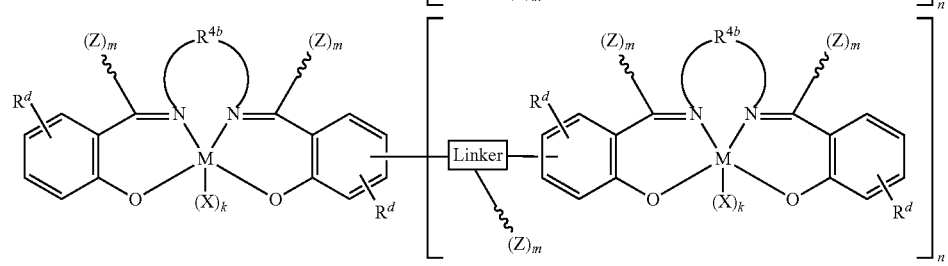

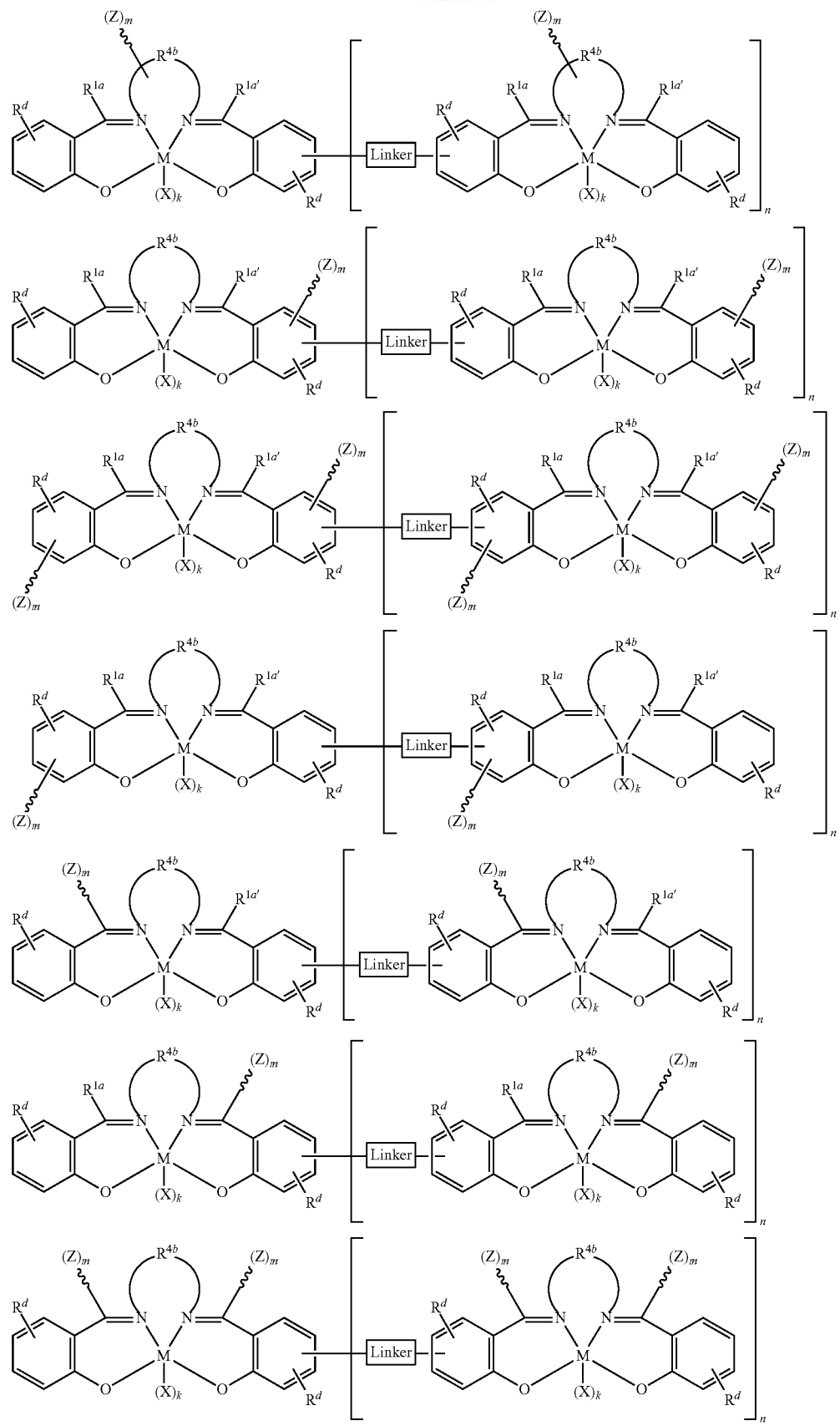

wherein each of $R^{1a}$, $R^{1a'}$, $R^{4b}$, $R^d$, M, X, k, n, —⟶$(Z)_m$, and the linker is as defined above and described in classes and subclasses herein, both singly and in combination.
In some embodiments, the linker is or comprises one or more activating moieties. In some embodiments, provided metals complexes are selected from the group consisting of:
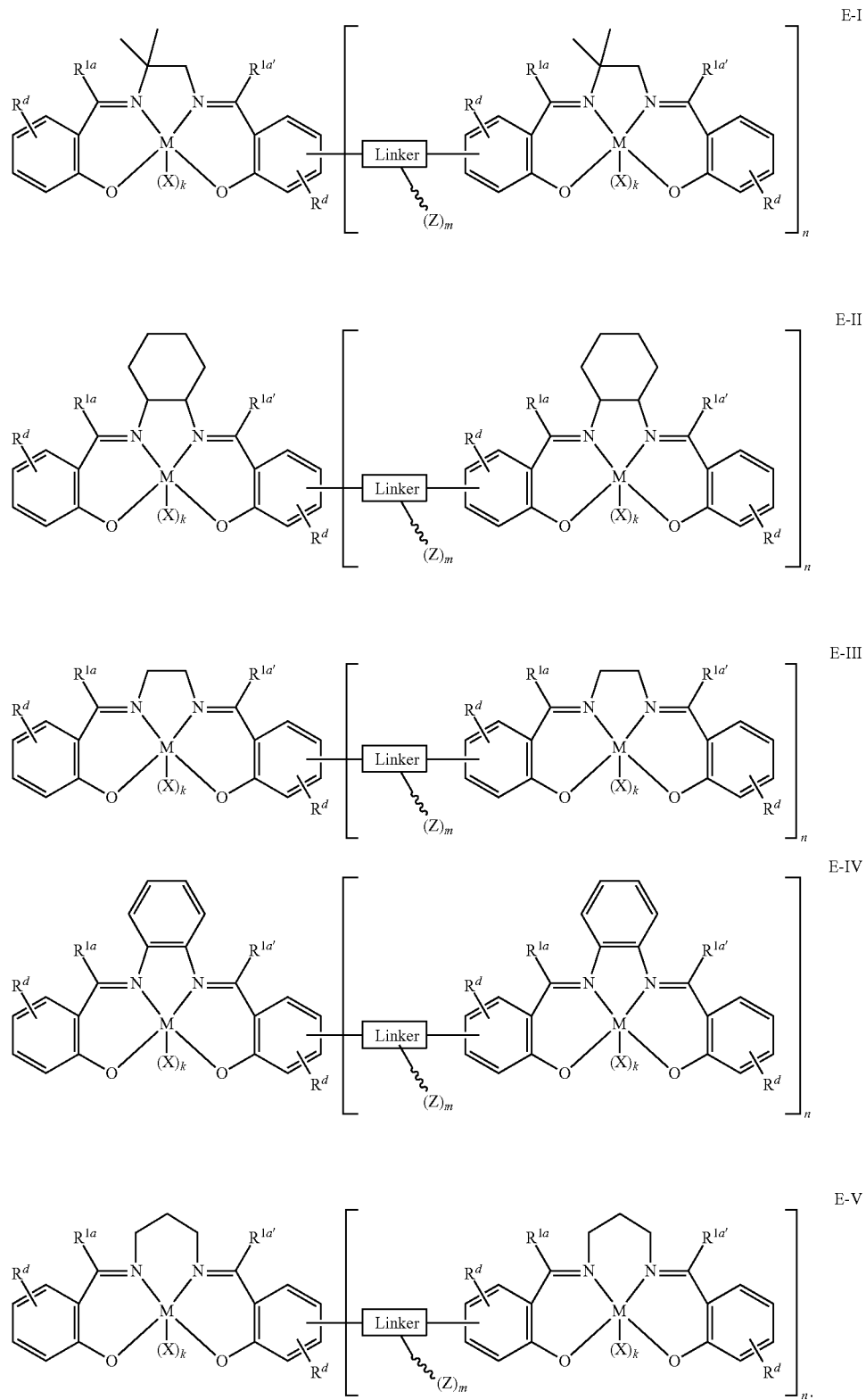

wherein each of $R^{1a}$, $R^{1a'}$, $R^d$, M, X, k, n, —$\sim\sim(Z)_m$, and the linker is as defined above and described in classes and subclasses herein, both singly and in combination.

In certain embodiments, the repeating units of n are joined to form a cyclic oligomeric complex. In certain embodiments, such cyclic oligomeric complexes are selected from the group consisting of:

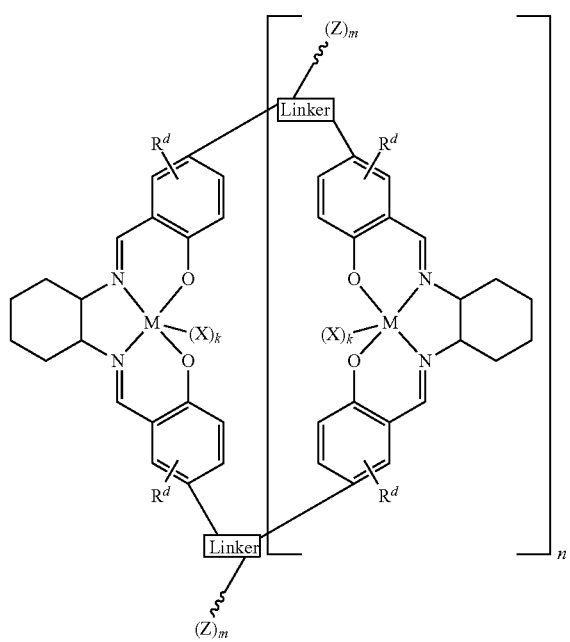

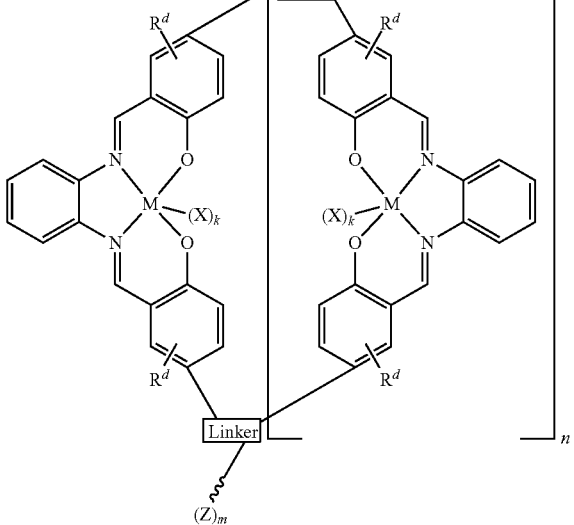

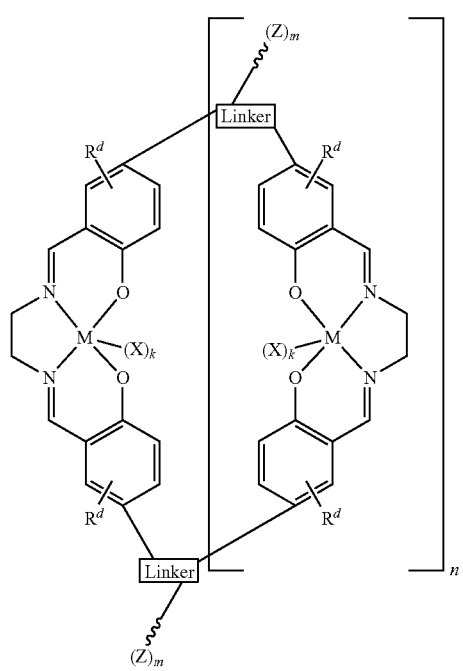

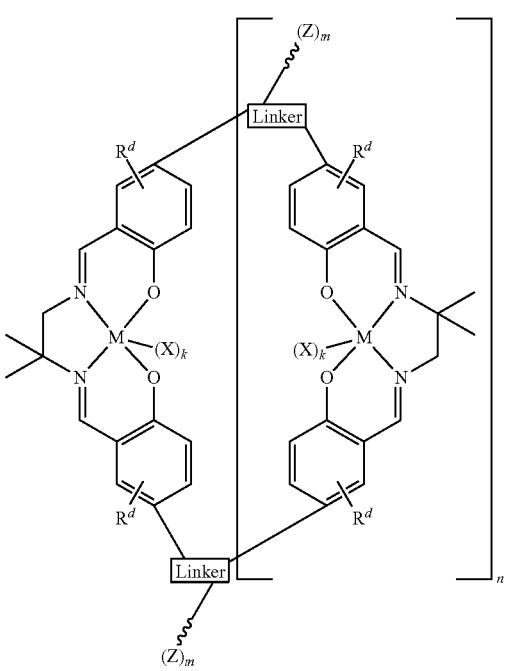

-continued
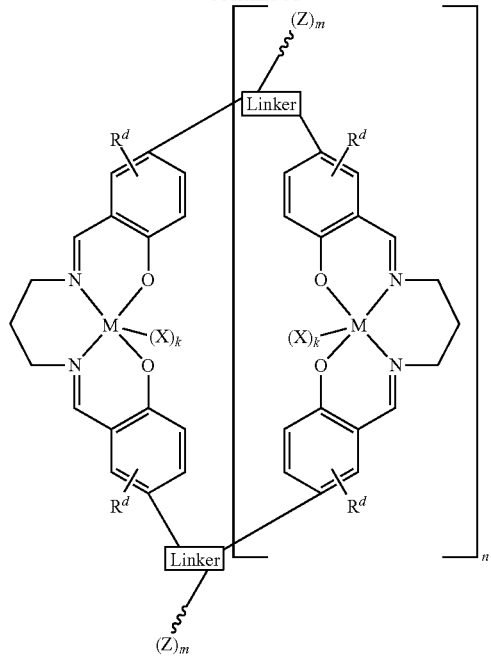
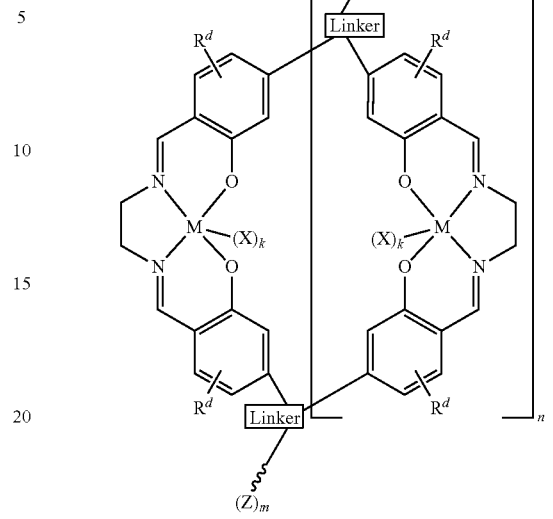
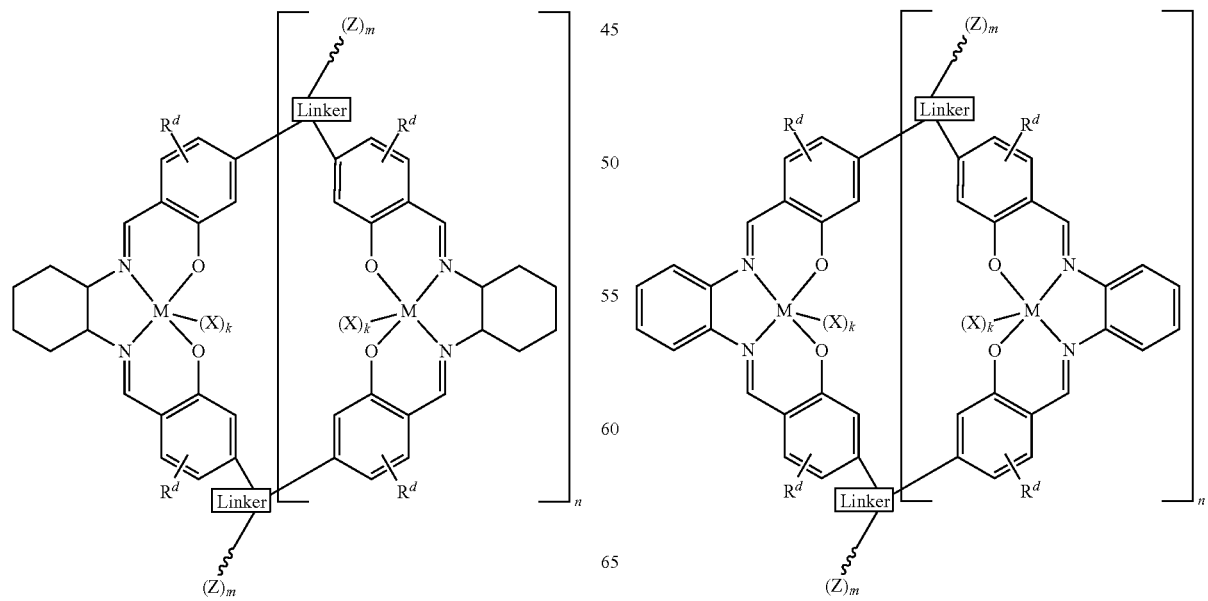

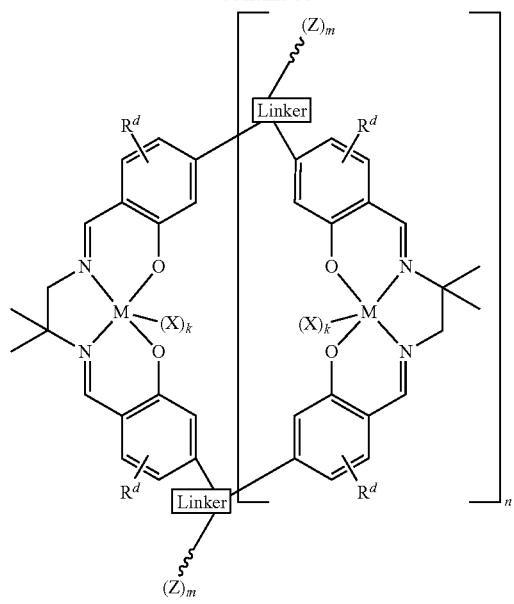
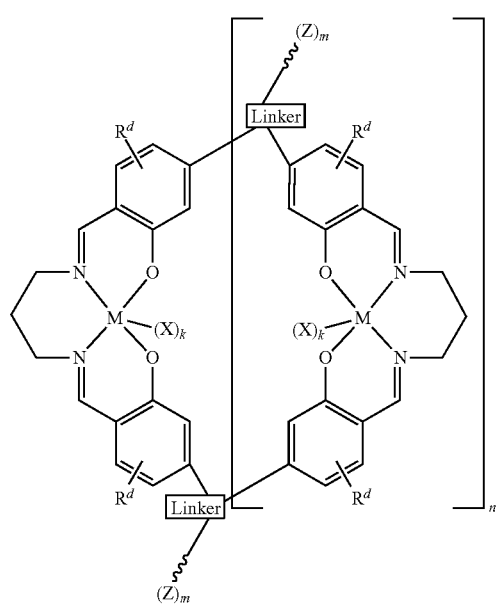
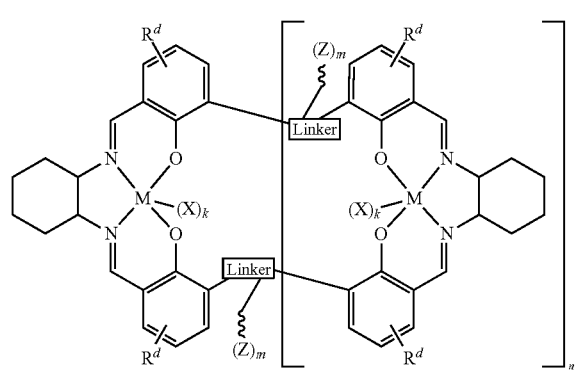
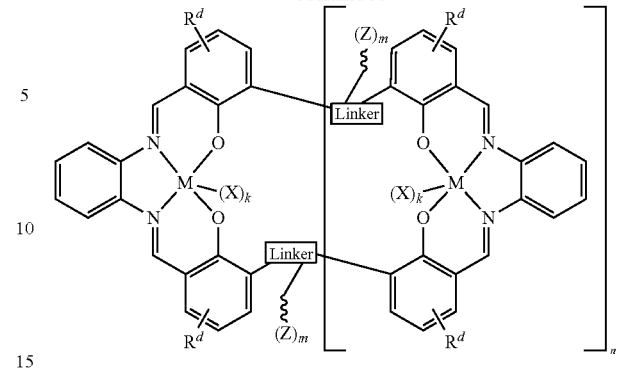
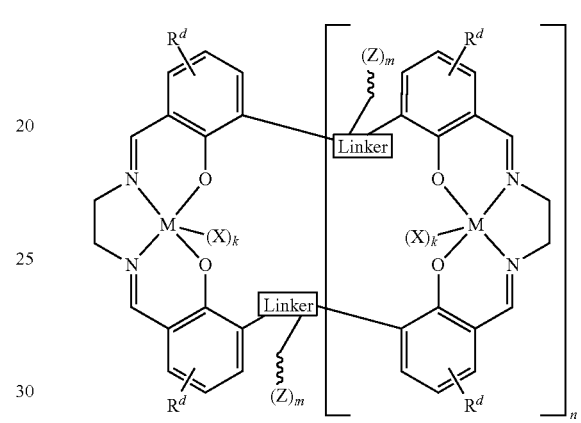
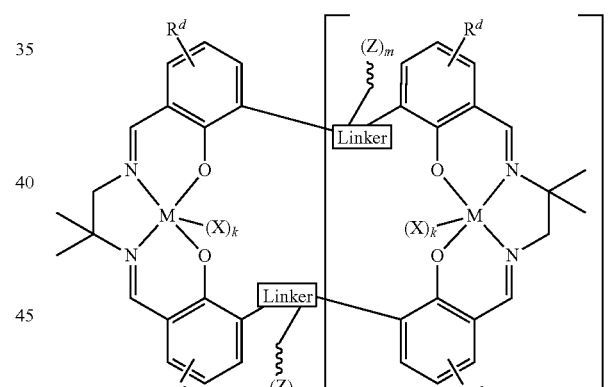
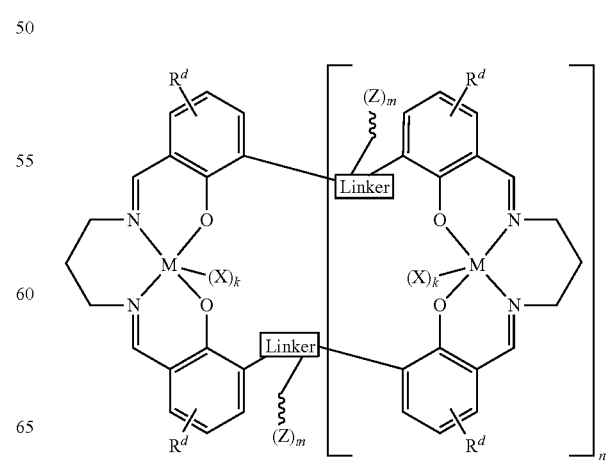

-continued
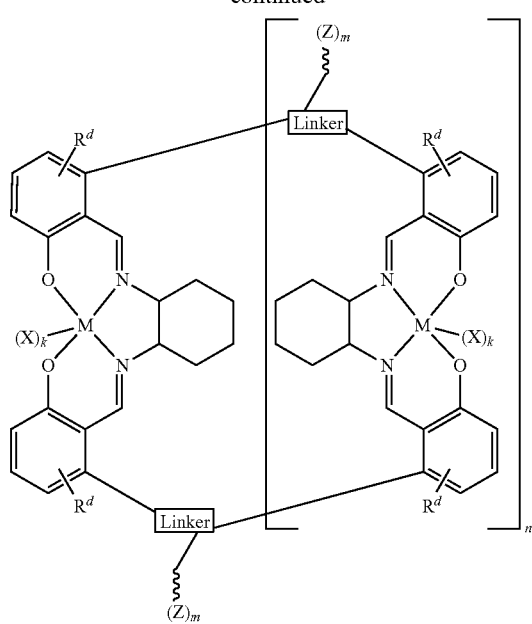 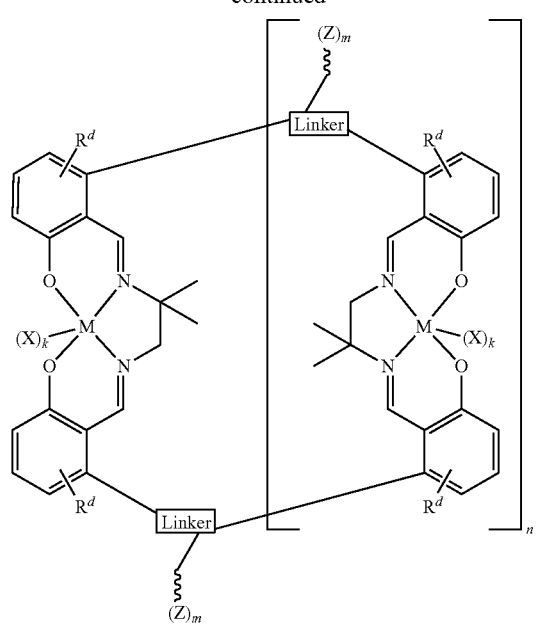
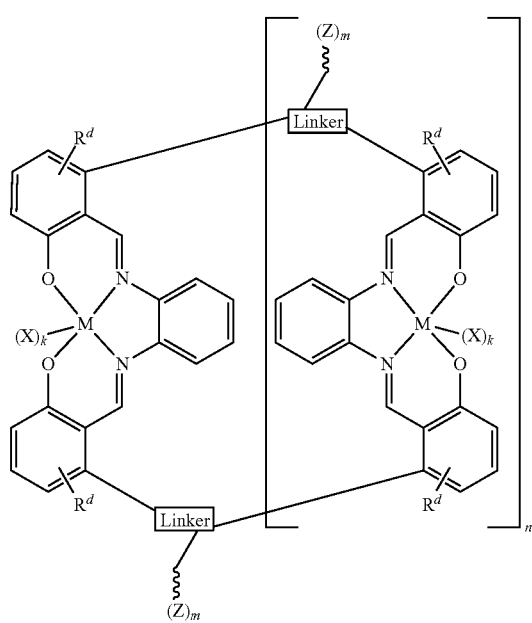 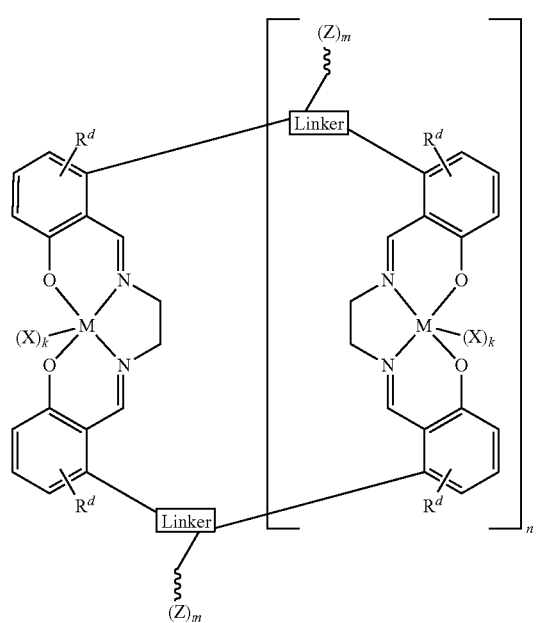

-continued
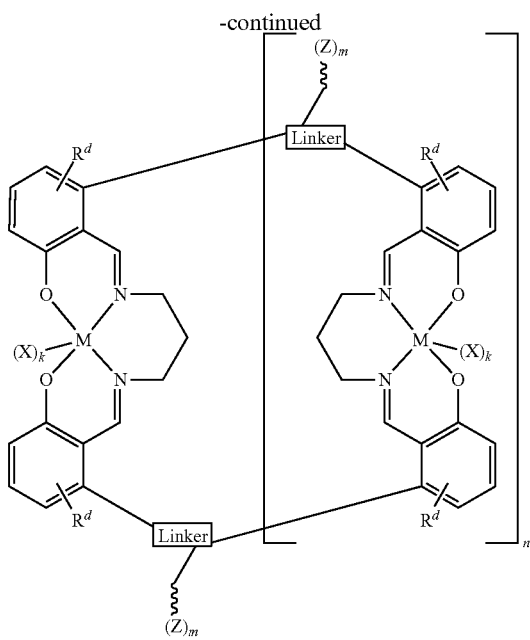
wherein each of $R^d$, M, X, k, n, —$(Z)_m$, and the linker is as defined above and described in classes and subclasses herein, both singly and in combination.
In some embodiments, provided metals complexes are selected from the group consisting of:
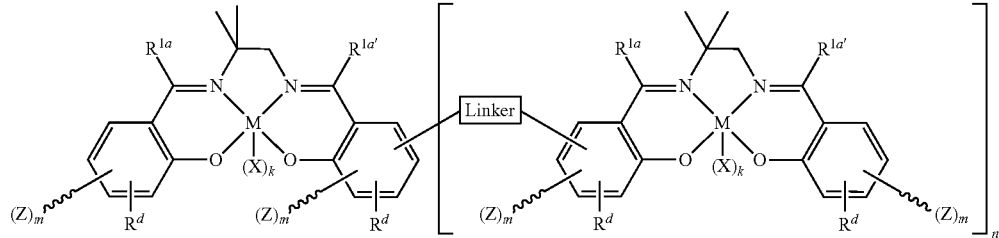
F-I
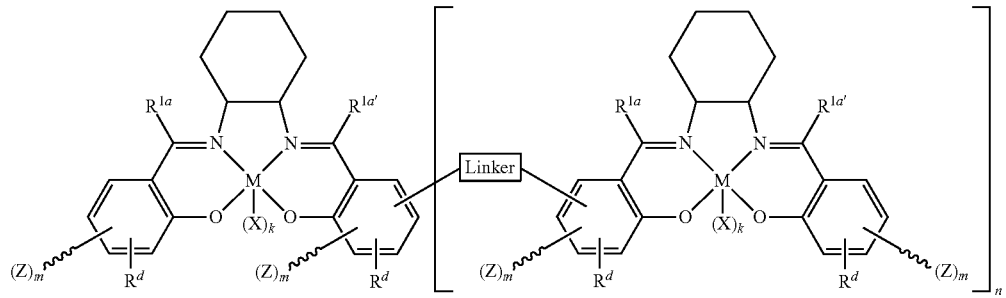
F-II
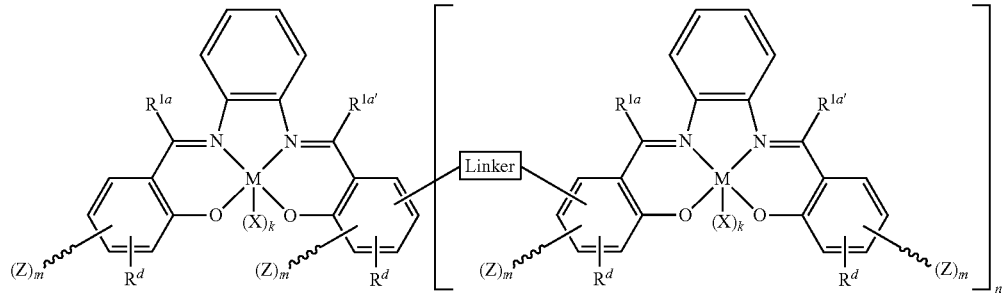
F-III

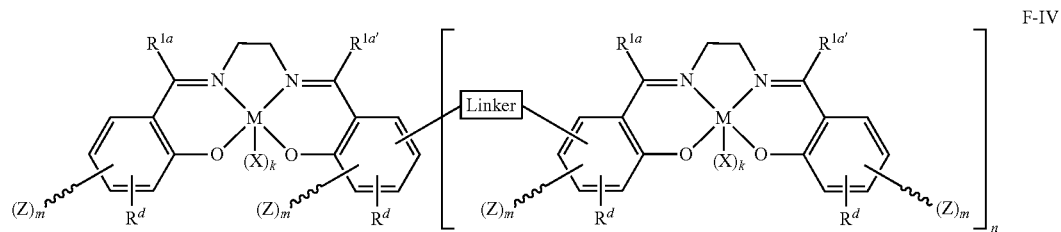
F-IV
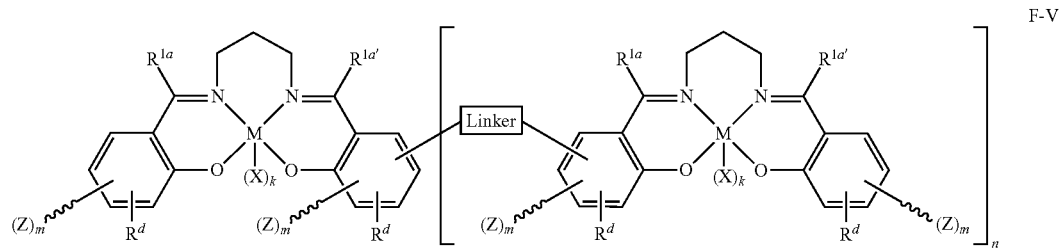
F-V
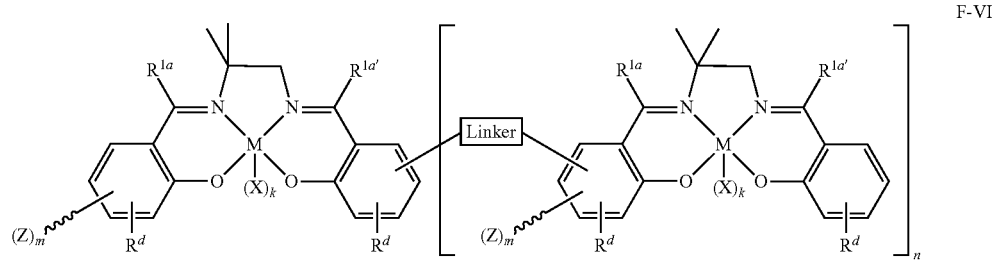
F-VI
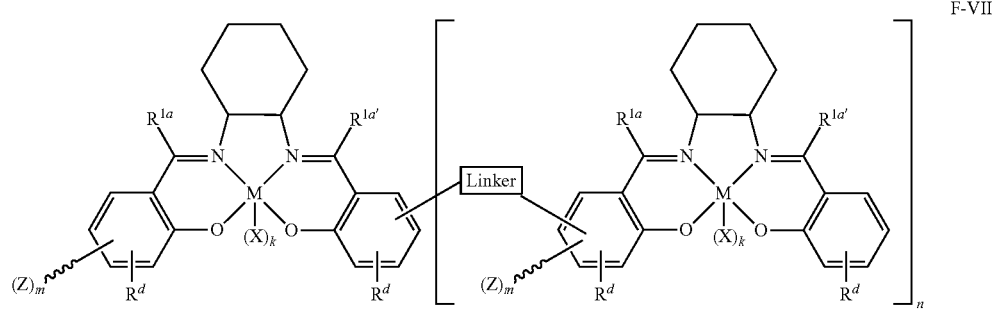
F-VII
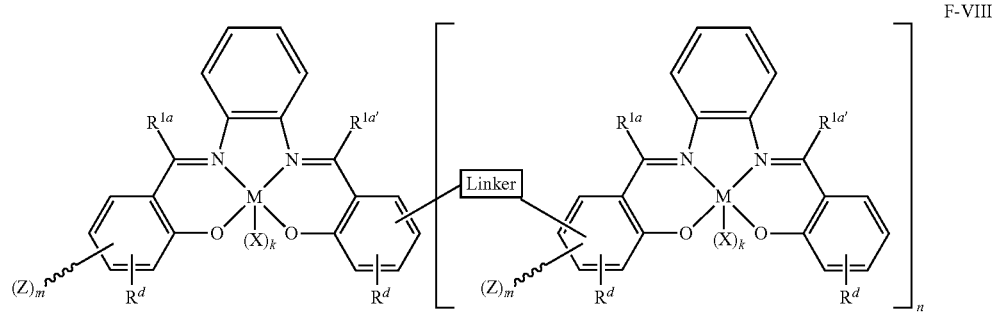
F-VIII
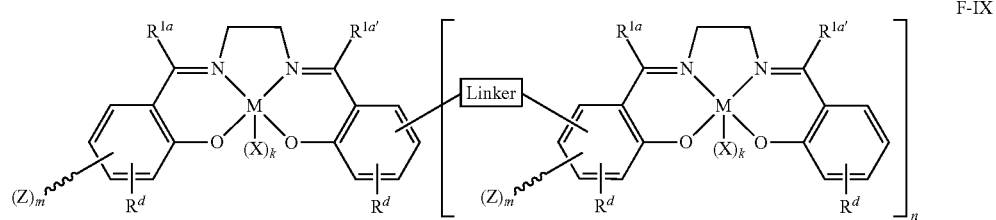
F-IX

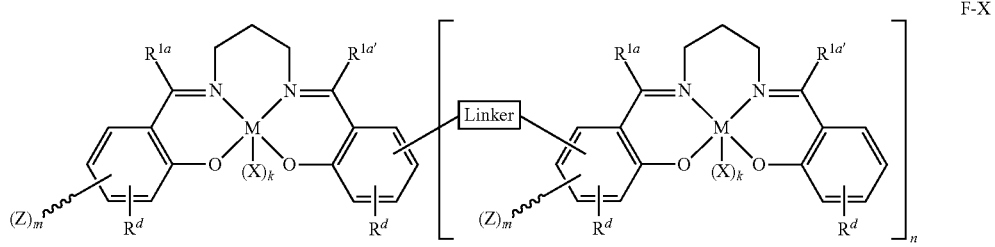

F-X wherein each of $R^{1a}$, $R^{1a'}$, $R^d$, M, X, k, n, —$\sim\sim(Z)_m$, and the linker is as defined above and described in classes and subclasses herein, both singly and in combination.

It will be appreciated that where the salen ligands in an oligomer of the present invention are asymmetric (e.g. each aryl ring has different substitution patterns, or the diamine linker is not C2 symmetric) and the chemistry used to link the metal complexes is not directional, the enchainment of the individual metal complexes in the oligomers may occur in more than one regiochemical orientation. While oligomers herein may be depicted with a fixed regiochemical arrangement of complexes, this is not meant to limit the present invention to those regiochemical arrangements. Indeed, in certain embodiments, oligomers of the present invention comprise materials with random regiochemical arrangements of asymmetric metal complexes. In other embodiments, oligomers of the present invention comprise materials with regiochemically defined arrangements of asymmetric metal complexes. As such, the generic structures depicted herein are not meant to impose any particular limitations on the regiochemistry of the claimed complexes and all possible regiochemical arrangements are encompassed unless specifically described otherwise. For example, for oligomers of formula E-IX above, though the structure shows the aryl rings of adjacent complexes to be regioregular, this structure should be understood to encompass regiorandom oligomers as well. For example, where n is 3, formula E-IX is meant to include all of these structures as well as others:

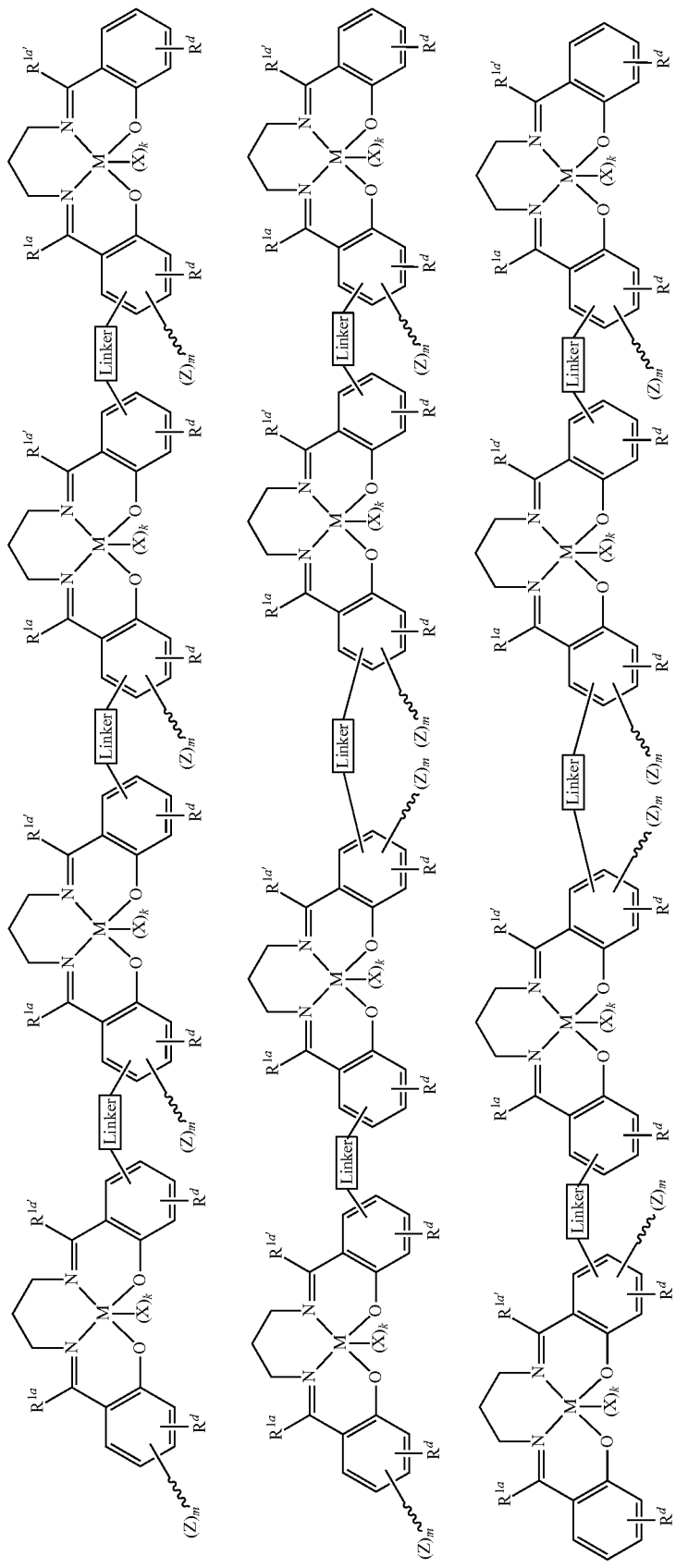

If the linkers are also asymmetric additional levels of regio-complexity may be present.
In certain embodiments, oligomers of the present invention comprise materials selected from the group consisting of:
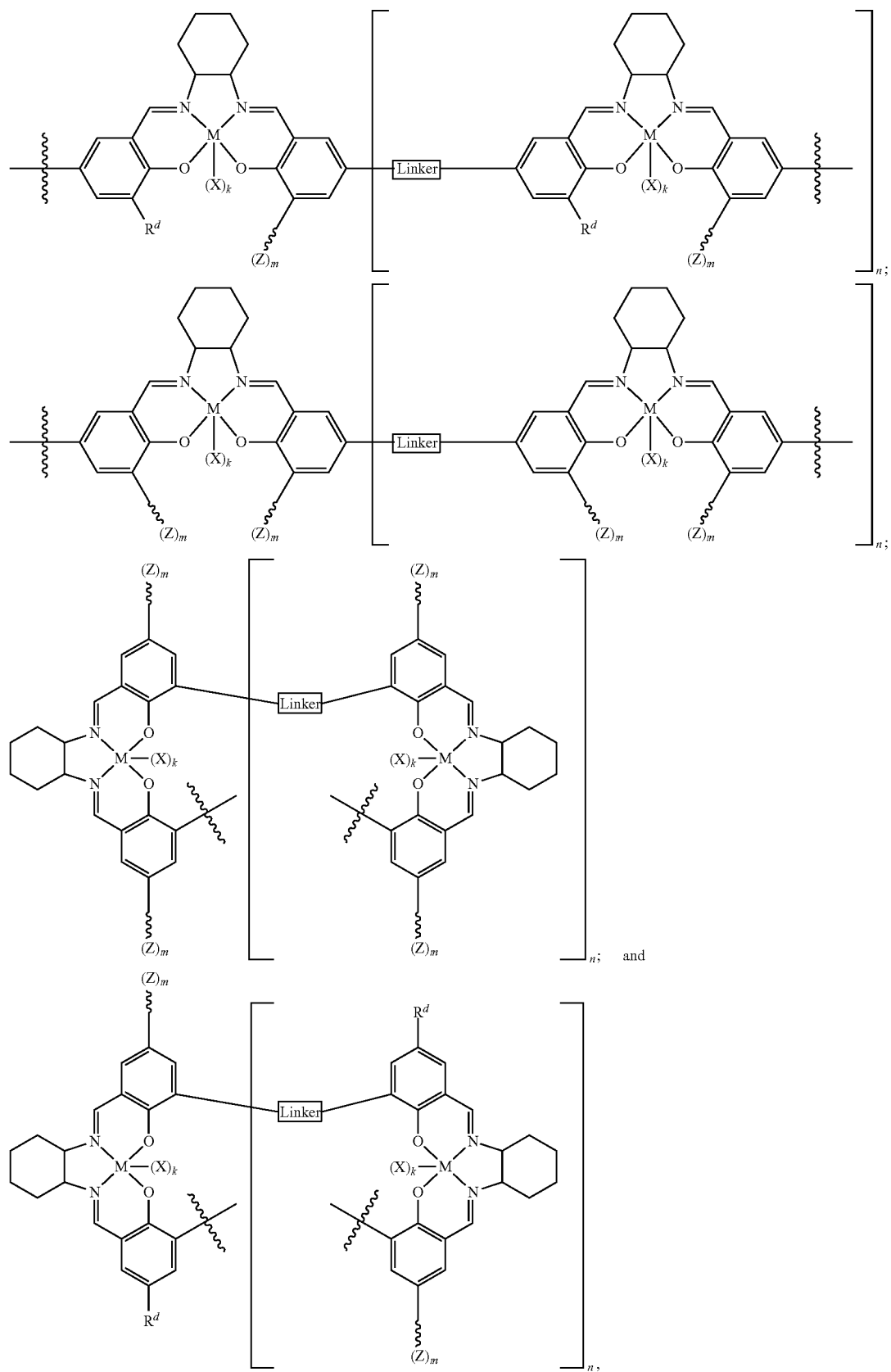

wherein each of $R^d$, M, X, k, n, —$\sim$$(Z)_m$, and the linker is as defined above and described in classes and subclasses herein, both singly and in combination. In these structures, the group $-\xi$, is used to represent the site of attachment of a partial linker moiety, or a functional group that is a precursor to a linker attachment. For example, in a complex where esterification chemistry is used to link the complexes in the oligomer, each $-\xi$ might represent a carboxyl group or a hydroxyl group, or the site of attachment of a functional group comprising a carboxyl group or a hydroxyl group.

In certain embodiments, the repeating units of n are joined to form a cyclic oligomeric complex. In certain embodiments, such cyclic oligomeric complexes are selected from the group consisting of:

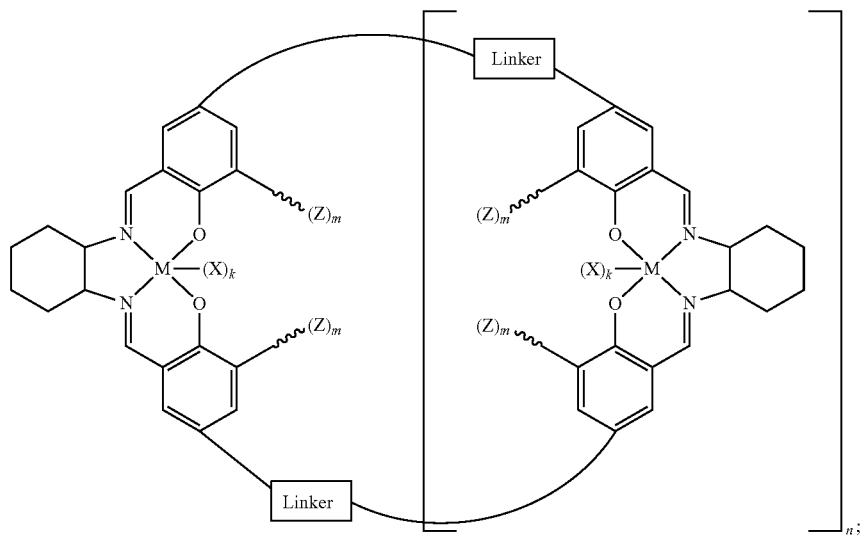

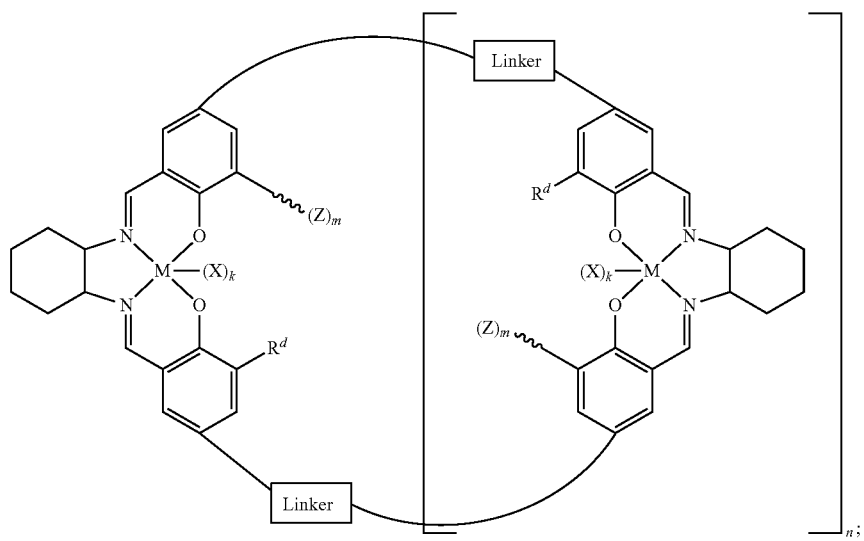

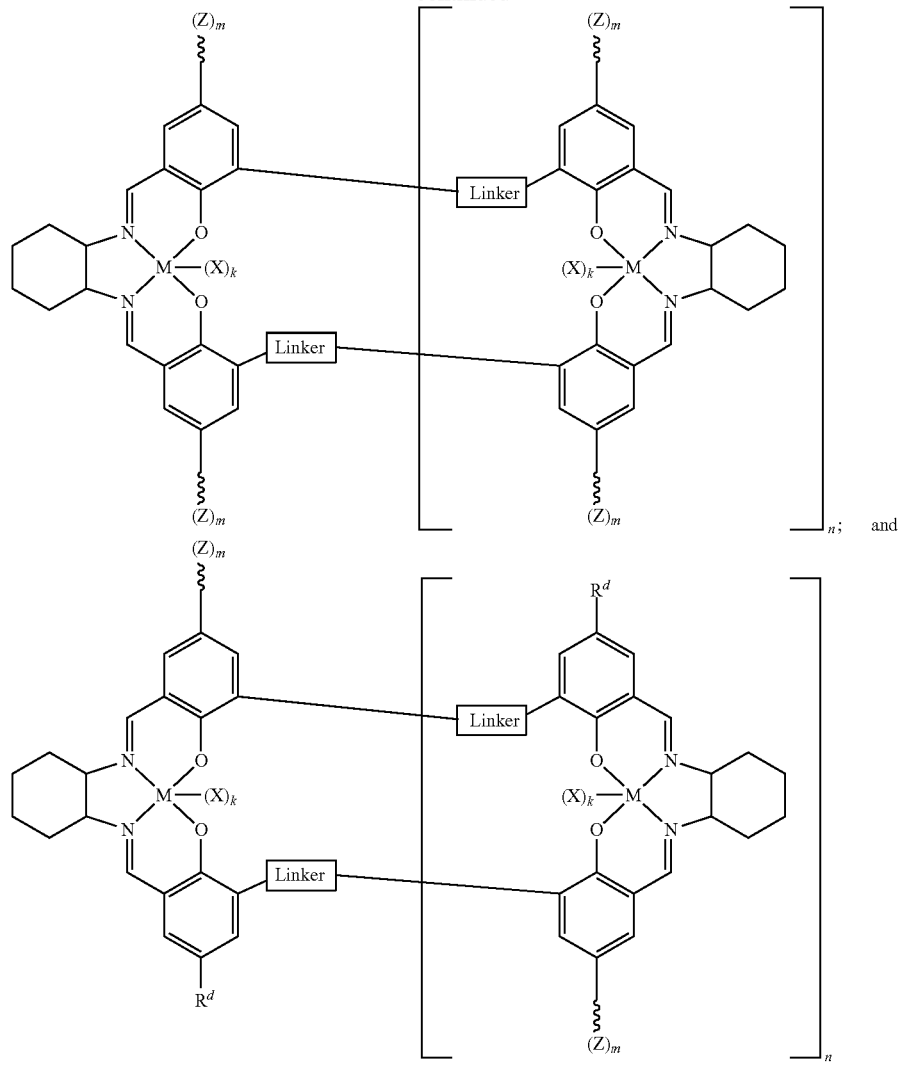

wherein each of $R^d$, M, X, k, n, ⁓$(Z)_m$, and the linker is as defined above and described in classes and subclasses herein, both singly and in combination.

II. Z-Linker Moieties

In certain embodiments, each activating moiety ⁓$(Z)_m$ comprises a tether "———⁓" coupled to at least one activating functional group Z as described above, with m denoting the number of activating functional groups present on a single Z-linker moiety.

In some embodiments, ⁓$(Z)_m$ is a bivalent group contained within a linker, as described above.

In some embodiments, there may be one or more activating moieties ⁓$(Z)_m$ tethered to a given metal complex; similarly, each activating moiety itself may contain more than one activating functional group Z. In certain embodiments, each activating moiety contains only one activating functional group (i.e. m=1). In some embodiments, each activating moiety contains more than one activating functional groups (i.e. m>1). In certain embodiments, an activating moiety contains two activating functional groups (i.e. m=2). In certain embodiments, an activating moiety contains three activating functional groups (i.e. m=3). In certain embodiments, an activating moiety contains four activating functional groups (i.e. m=4). In certain embodiments where more than one activating functional group is present on an activating moiety, the activating functional groups are the same. In some embodiments where more than one activating functional group is present on an activating moiety, two or more of the activating functional groups are different.

In certain embodiments, each tether (or "Z-linker") moiety ———⁓ contains 1-30 atoms including at least one carbon atom, and optionally one or more atoms selected from the group consisting of N, O, S, Si, B, and P.

In certain embodiments, a Z-linker is an optionally substituted $C_{2-30}$ aliphatic group wherein one or more carbons are optionally and independently replaced by -Cy-, —$NR^y$—, —N($R^y$)C(O)—, —C(O)N($R^y$)—, —O—, —C(O)—, —OC(O)—, —C(O)O—, —S—, —SO—, —$SO_2$—, —C(=S)—, —C(=$NR^y$)—, or —N=N—, wherein:

each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and each $R^y$ is independently —H, or an optionally substituted radical selected from the group consisting of $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, a 5-6 membered heteroaryl ring having 1-3 heteroatoms independently selected from nitrogen, oxygen, or sulfur, and 8- to 10-membered aryl.

In certain embodiments, a Z-linker moiety is a $C_4$-$C_{12}$ aliphatic group substituted with one or more moieties selected from the group consisting of halogen, —$NO_2$, —CN, —$SR^y$, —$S(O)R^y$, —$S(O)_2R^y$, —$NR^yC(O)R^y$, —$OC(O)R^y$, —$CO_2R^y$, —NCO, —$N_3$, —$OR^4$, —$OC(O)N(R^y)_2$, —$N(R^y)_2$, —$NR^yC(O)R^y$, and —$NR^yC(O)OR^y$, where each $R^y$ and $R^4$ is independently as defined above and described in classes and subclasses herein.

In certain embodiments, a Z-linker moiety is an optionally substituted $C_3$-$C_{30}$ aliphatic group. In certain embodiments, a Z-linker is an optionally substituted $C_{4-24}$ aliphatic group. In certain embodiments, a Z-linker moiety is an optionally substituted $C_4$-$C_{20}$ aliphatic group. In certain embodiments, a Z-linker moiety is an optionally substituted $C_4$-$C_{12}$ aliphatic group. In certain embodiments, a Z-linker is an optionally substituted $C_{4-10}$ aliphatic group. In certain embodiments, a Z-linker is an optionally substituted $C_{4-8}$ aliphatic group. In certain embodiments, a Z-linker moiety is an optionally substituted $C_4$-$C_6$ aliphatic group. In certain embodiments, a Z-linker moiety is an optionally substituted $C_6$-$C_{12}$ aliphatic group. In certain embodiments, a Z-linker moiety is an optionally substituted $C_8$ aliphatic group. In certain embodiments, a Z-linker moiety is an optionally substituted $C_7$ aliphatic group. In certain embodiments, a Z-linker moiety is an optionally substituted $C_6$ aliphatic group. In certain embodiments, a Z-linker moiety is an optionally substituted $C_5$ aliphatic group. In certain embodiments, a Z-linker moiety is an optionally substituted $C_4$ aliphatic group. In certain embodiments, a Z-linker moiety is an optionally substituted $C_3$ aliphatic group. In certain embodiments, a aliphatic group in the Z-linker moiety is an optionally substituted straight alkyl chain. In certain embodiments, the aliphatic group is an optionally substituted branched alkyl chain. In some embodiments, a Z-linker moiety is a $C_4$ to $C_{20}$ alkyl group having one or more methylene groups replaced by —$C(R°)_2$— wherein $R°$ is as defined above. In certain embodiments, a Z-linker moiety consists of a bivalent aliphatic group having 4 to 30 carbons including one or more $C_{1-4}$ alkyl substituted carbon atoms. In certain embodiments, a Z-linker moiety consists of a bivalent aliphatic group having 4 to 30 carbons including one or more gem-dimethyl substituted carbon atoms.

In certain embodiments, a Z-linker moiety includes one or more optionally substituted cyclic elements selected from the group consisting of saturated or partially unsaturated carbocyclic, aryl, heterocyclic, or heteroaryl. In certain embodiments, a Z-linker moiety consists of the substituted cyclic element, in some embodiments the cyclic element is part of a Z-linker with one or more non-ring heteroatoms or optionally substituted aliphatic groups comprising other parts of the Z-linker moiety.

In some embodiments, a Z-linker moiety is of sufficient length to allow one or more activating functional groups to be positioned near a metal atom of a metal complex. In certain embodiments, structural constraints are built into a Z-linker moiety to control the disposition and orientation of one or more activating functional groups near a metal center of a metal complex. In certain embodiments, such structural constraints are selected from the group consisting of cyclic moieties, bicyclic moieties, bridged cyclic moieties and tricyclic moieties. In some embodiments, such structural constraints are the result of acyclic steric interactions. In certain embodiments, steric interactions due to syn-pentane, gauche-butane, and/or allylic strain in a Z-linker moiety, bring about structural constraints that affect the orientation of a Z-linker and one or more activating groups. In certain embodiments, structural constraints are selected from the group consisting of cis double bonds, trans double bonds, cis allenes, trans allenes, and triple bonds. In some embodiments, structural constraints are selected from the group consisting of substituted carbons including geminally disubstituted groups such as sprirocyclic rings, gem dimethyl groups, gem diethyl groups and gem diphenyl groups. In certain embodiments, structural constraints are selected from the group consisting of heteroatom-containing functional groups such as sulfoxides, amides, and oximes.

In certain embodiments, Z-linker moieties are selected from the group consisting of:

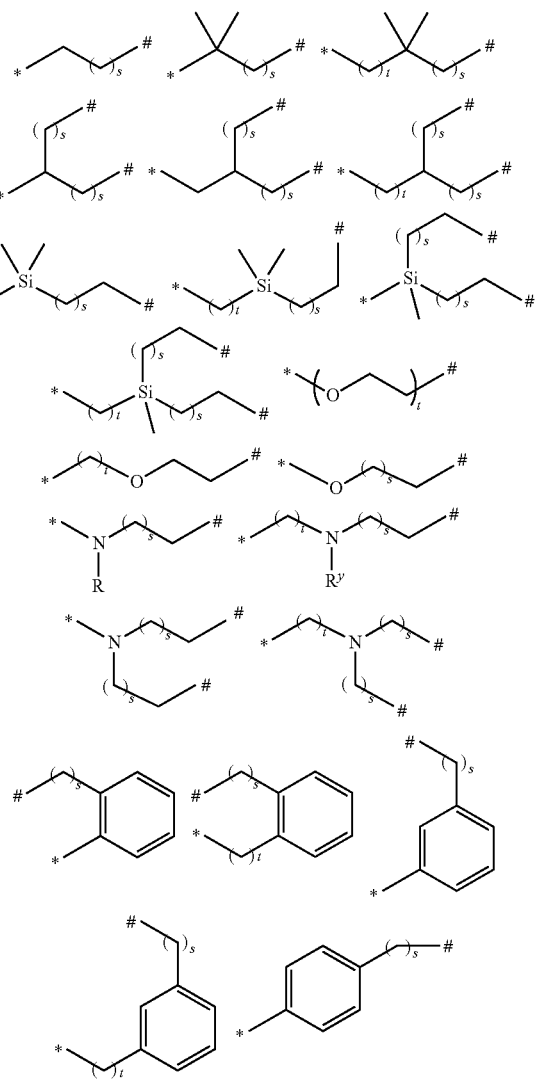

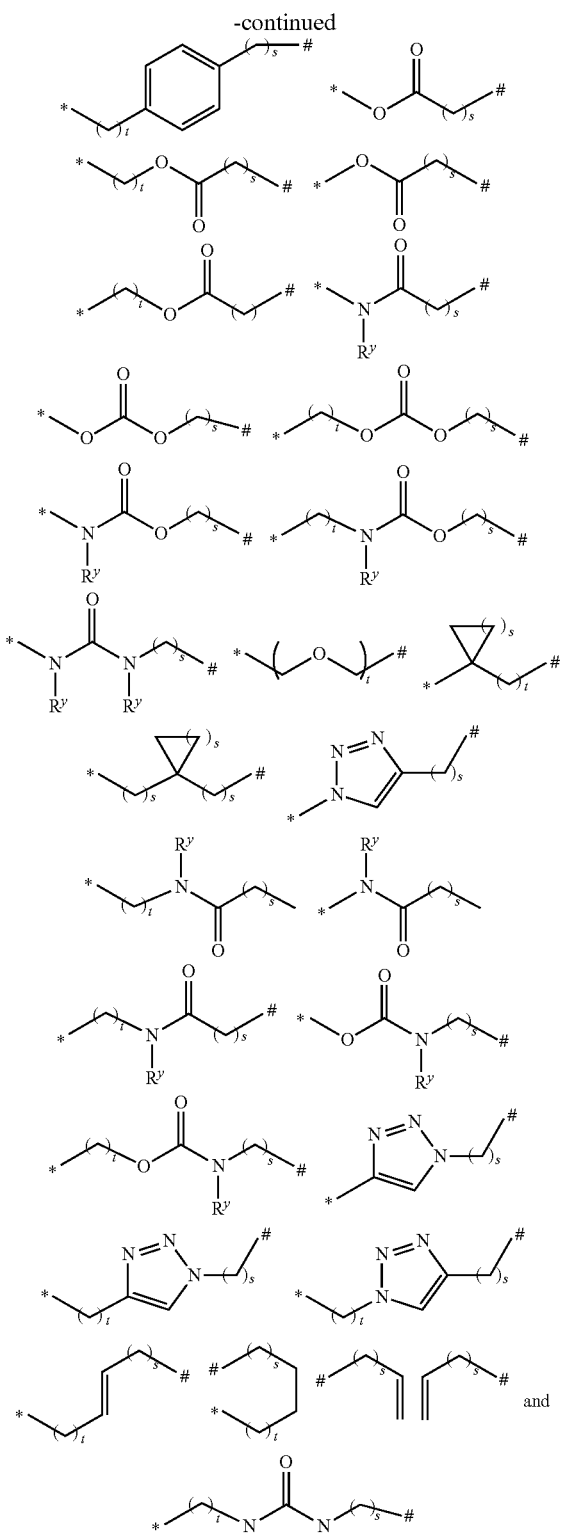

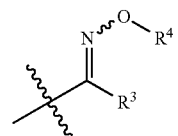

wherein each s is independently 0-6, t is 0-4, $R^y$ as defined above and described in classes and subclasses herein, * represents the site of attachment to a ligand, and each # represents a site of attachment of an activating functional group.

In some embodiments, s is 0. In some embodiments, s is 1. In some embodiments, s is 2. In some embodiments, s is 3. In some embodiments, s is 4. In some embodiments, s is 5. In some embodiments, s is 6.

In some embodiments, t is 1. In some embodiments, t is 2. In some embodiments, t is 3. In some embodiments, t is 4.

II. Activating Functional Groups

In some embodiments, an activating functional group is selected from the group consisting of neutral nitrogen-containing functional groups, cationic moieties, phosphorous-containing functional groups, and combinations of two or more of these. In some embodiments, one or more Z group is independently a neutral functional group selected from the group consisting of amines, phosphines, guanidines, bis-guanidines, amidines, and nitrogen-containing heterocycles.

II.a. Neutral Nitrogen-Containing Activating Groups

In some embodiments, one or more tethered activating functional groups on provided metal complexes are neutral nitrogen-containing moieties. In some embodiments, such moieties include one or more of the structures in Table Z-1:

TABLE Z-1

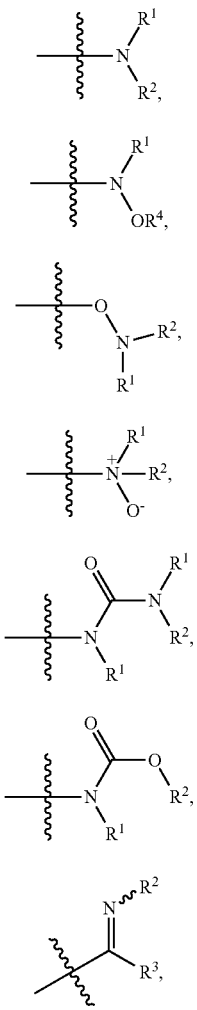

TABLE Z-1-continued

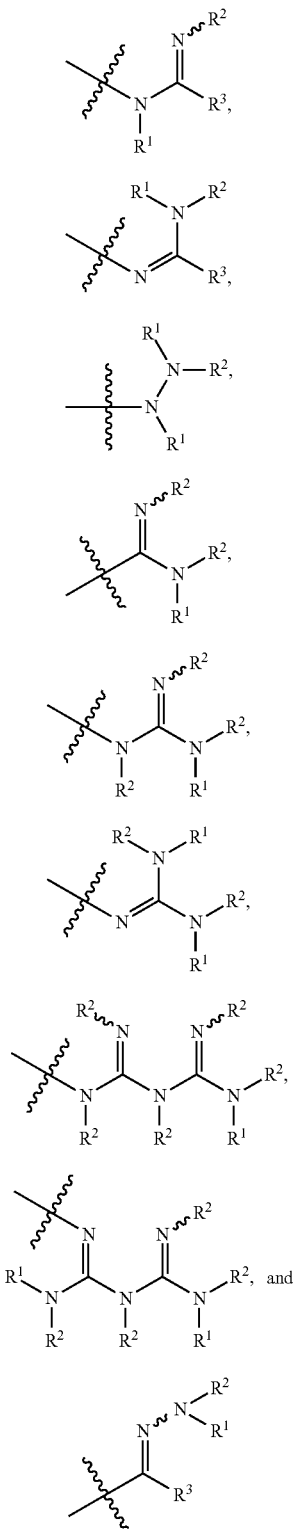

or a combination of two or more of these,
wherein:
each $R^1$ and $R^2$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic car-
bocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^1$ and $R^2$ can be taken together with intervening atoms to form one or more optionally substituted rings optionally containing one or more additional heteroatoms;

each $R^3$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^3$ group can be taken with an $R^1$ or $R^2$ group to form one or more optionally substituted rings; and each $R^4$ is independently hydrogen, a hydroxyl protecting group, or an optionally substituted radical selected from the group consisting of $C_{1-20}$ acyl; $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring.

In certain embodiments, each $R^1$ group is the same. In other embodiments, $R^1$ groups are different. In certain embodiments, $R^1$ is hydrogen. In some embodiments, $R^1$ is an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In some embodiments, $R^1$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring.

In certain embodiments, $R^1$ is an optionally substituted radical selected from the group consisting of $C_{1-12}$ aliphatic and $C_{1-12}$ heteroaliphatic. In some embodiments, $R^1$ is optionally substituted $C_{1-20}$ aliphatic. In some embodiments, $R^1$ is optionally substituted $C_{1-12}$ aliphatic. In some embodiments, $R^1$ is optionally substituted $C_{1-6}$ aliphatic. In some embodiments, $R^1$ is optionally substituted $C_{1-20}$ heteroaliphatic. In some embodiments, $R^1$ is optionally substituted $C_{1-12}$ heteroaliphatic. In some embodiments, $R^1$ is optionally substituted phenyl. In some embodiments, $R^1$ is optionally substituted 8- to 10-membered aryl. In some embodiments, $R^1$ is an optionally substituted 5- to 6-membered heteroaryl group. In some embodiments, $R^1$ is an optionally substituted 8- to 14-membered polycyclic heteroaryl group. In some embodiments, $R^1$ is optionally substituted 3- to 8-membered heterocyclic.

In certain embodiments, each $R^1$ is independently hydrogen, methyl, ethyl, propyl, butyl, pentyl, hexyl, heptyl, octyl, optionally substituted phenyl, or optionally substituted benzyl. In certain embodiments, $R^1$ is methyl, ethyl, propyl, butyl, pentyl, hexyl, heptyl, octyl, phenyl or benzyl. In some embodiments, $R^1$ is butyl. In some embodiments, $R^1$ is isopropyl. In some embodiments, $R^1$ is neopentyl. In some embodiments, $R^1$ is perfluoro. In some embodiments, $R^1$ is —$CF_2CF_3$. In some embodiments, $R^1$ is phenyl. In some embodiments, $R^1$ is benzyl.

In certain embodiments, each $R^2$ group is the same. In other embodiments, $R^2$ groups are different. In certain embodiments, $R^2$ is hydrogen. In some embodiments, $R^2$ is an optionally substituted radical selected from the group consisting of $C_{1-20}$ aliphatic; $C_{1-20}$ heteroaliphatic, 5- to 14-membered heteroaryl, phenyl, 8- to 10-membered aryl and 3- to 7-membered heterocyclic. In some embodiments, $R^2$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring.

In certain embodiments, $R^2$ is an optionally substituted radical selected from the group consisting of $C_{1-12}$ aliphatic and $C_{1-12}$ heteroaliphatic. In some embodiments, $R^2$ is optionally substituted $C_{1-20}$ aliphatic. In some embodiments, $R^2$ is optionally substituted $C_{1-12}$ aliphatic. In some embodiments, $R^2$ is optionally substituted $C_{1-6}$ aliphatic. In some embodiments, $R^2$ is optionally substituted $C_{1-20}$ heteroaliphatic. In some embodiments, $R^2$ is optionally substituted $C_{1-12}$ heteroaliphatic. In some embodiments, $R^2$ is optionally substituted phenyl. In some embodiments, $R^2$ is optionally substituted 8- to 10-membered aryl. In some embodiments, $R^2$ is an optionally substituted 5- to 6-membered heteroaryl group. In some embodiments, $R^2$ is an optionally substituted 8- to 14-membered polycyclic heteroaryl group. In some embodiments, $R^2$ is optionally substituted 3- to 8-membered heterocyclic.

In certain embodiments, each $R^2$ is independently hydrogen, methyl, ethyl, propyl, butyl, pentyl, hexyl, heptyl, octyl, optionally substituted phenyl, or optionally substituted benzyl. In certain embodiments, $R^2$ is methyl, ethyl, propyl, butyl, pentyl, hexyl, heptyl, octyl, phenyl or benzyl. In some embodiments, $R^2$ is butyl. In some embodiments, $R^2$ is isopropyl. In some embodiments, $R^2$ is neopentyl. In some embodiments, $R^2$ is perfluoro. In some embodiments, $R^2$ is —$CF_2CF_3$. In some embodiments, $R^2$ is phenyl. In some embodiments, $R^2$ is benzyl.

In certain embodiments, each $R^1$ and $R^2$ are hydrogen. In some embodiments, each $R^1$ is hydrogen each and each $R^2$ is other than hydrogen. In some embodiments, each $R^2$ is hydrogen each and each $R^1$ is other than hydrogen.

In certain embodiments, $R^1$ and $R^2$ are both methyl, ethyl, propyl, butyl, pentyl, hexyl, heptyl, octyl, phenyl or benzyl. In some embodiments, $R^1$ and $R^2$ are each butyl. In some embodiments, $R^1$ and $R^2$ are each isopropyl. In some embodiments, $R^1$ and $R^2$ are each perfluoro. In some embodiments, $R^1$ and $R^2$ are —$CF_2CF_3$. In some embodiments, $R^1$ and $R^2$ are each phenyl. In some embodiments, $R^1$ and $R^2$ are each benzyl.

In some embodiments, $R^1$ and $R^2$ are taken together with intervening atoms to form one or more optionally substituted carbocyclic, heterocyclic, aryl, or heteroaryl rings. In certain embodiments, $R^1$ and $R^2$ are taken together to form a ring fragment selected from the group consisting of: —$C(R^y)_2$—, —$C(R^y)_2C(R^y)_2$—, —$C(R^y)_2C(R^y)_2C(R^y)_2$—, —$C(R^y)_2OC(R^y)_2$—, and —$C(R^y)_2NR^yC(R^y)_2$—, wherein $R^y$ is as defined above. In certain embodiments, $R^1$ and $R^2$ are taken together to form a ring fragment selected from the group consisting of: —$CH_2$—, —$CH_2CH_2$—, —$CH_2CH_2CH_2$—, —$CH_2OCH_2$—, and —$CH_2NR^yCH_2$—. In some embodiments, $R^1$ and $R^2$ are taken together to form an unsaturated linker moiety optionally containing one or more additional heteroatoms. In some embodiments, the resulting nitrogen-containing ring is partially unsaturated. In certain embodiments, the resulting nitrogen-containing ring comprises a fused polycyclic heterocycle.

In certain embodiments, $R^3$ is H. In certain embodiments, $R^3$ is optionally $C_{1-20}$ aliphatic; $C_{1-20}$ heteroaliphatic, 5- to 14-membered heteroaryl, phenyl, 8- to 10-membered aryl or 3- to 7-membered heterocyclic. In some embodiments, $R^3$ is an optionally substituted radical selected from the group consisting of a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring. In certain embodiments, $R^3$ is optionally substituted $C_{1-12}$ aliphatic. In some embodiments, R³ is optionally substituted C₁₋₆ aliphatic. In certain embodiments, R³ is optionally substituted phenyl.

In certain embodiments, R³ is methyl, ethyl, propyl, butyl, pentyl, hexyl, heptyl, octyl, phenyl or benzyl. In some embodiments, R³ is butyl. In some embodiments, R³ is isopropyl. In some embodiments, R³ is perfluoro. In some embodiments, R³ is —CF₂CF₃.

In some embodiments, one or more R¹ or R² groups are taken together with R³ and intervening atoms to form an optionally substituted heterocyclic or heteroaryl ring. In certain embodiments, R¹ and R³ are taken together to form an optionally substituted 5- or 6-membered ring. In some embodiments, R² and R³ are taken together to form an optionally substituted 5- or 6-membered ring optionally containing one or more additional heteroatoms. In some embodiments, R¹, R² and R³ are taken together to form an optionally substituted fused ring system. In some embodiments, such rings formed by combinations of any of R¹, R² and R³ are partially unsaturated or aromatic.

In certain embodiments, R⁴ is hydrogen. In some embodiments, R⁴ is an optionally substituted radical selected from the group consisting of C₁₋₁₂ aliphatic, phenyl, 8- to 10-membered aryl, and 3- to 8-membered heterocyclic. In certain embodiments, R⁴ is a C₁₋₁₂ aliphatic. In certain embodiments, R⁴ is a C₁₋₆ aliphatic. In some embodiments, R⁴ is an optionally substituted 8- to 10-membered aryl group. In certain embodiments, R⁴ is optionally substituted C₁₋₁₂ acyl or in some embodiments, optionally substituted C₁₋₆ acyl. In certain embodiments, R⁴ is optionally substituted phenyl. In some embodiments, R⁴ is a hydroxyl protecting group. In some embodiments, R⁴ is a silyl protecting group. In some embodiments, R⁴ is methyl, ethyl, propyl, butyl, pentyl, hexyl, heptyl, octyl, allyl, phenyl or benzyl.

In certain embodiments, R¹ and R⁴ are taken together with intervening atoms to form one or more optionally substituted heterocyclic or heteroaryl rings optionally containing one or more additional heteroatoms.

In some embodiments, an activating functional group is an N-linked amino group:

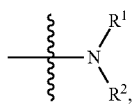

wherein R¹ and R² are as defined above and described in classes and subclasses herein.

In some embodiments, an N-linked amino activating functional group is selected from the group consisting of:

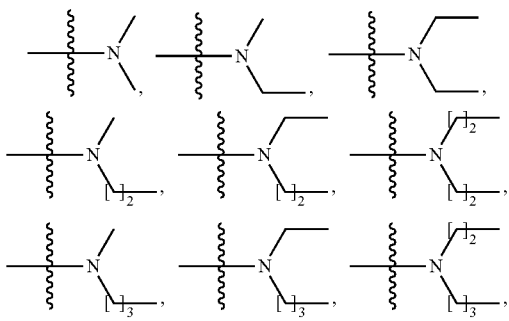

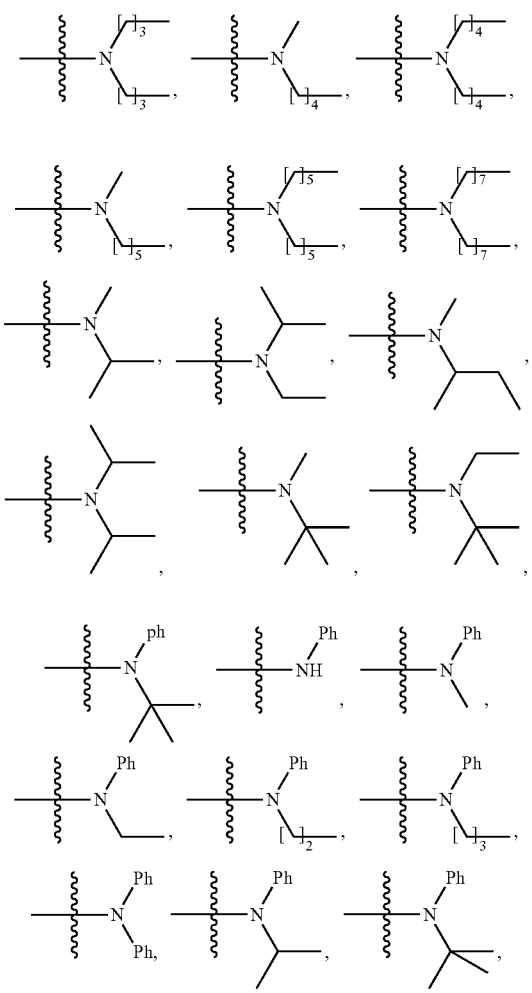

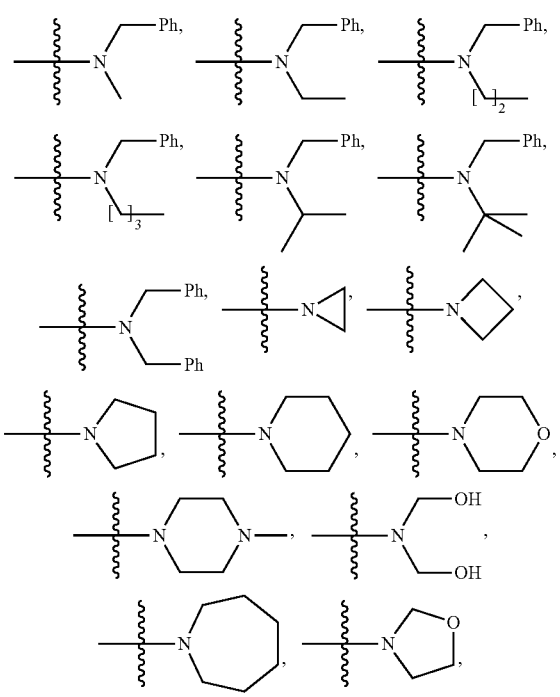

-continued

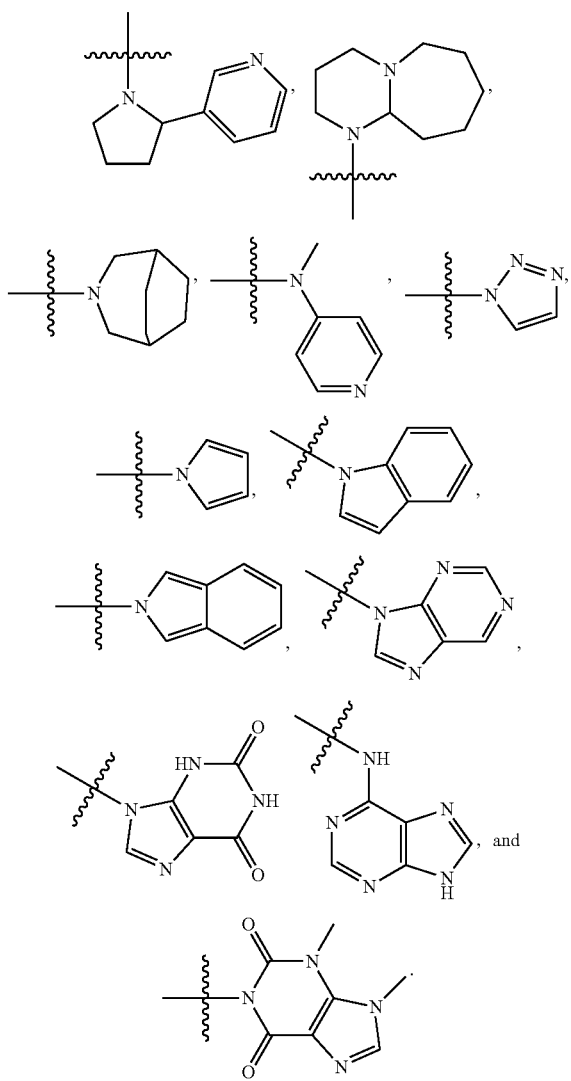

In some embodiments, one or more activating functional groups is an N-linked hydroxyl amine derivative:

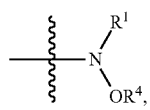

wherein $R^1$ and $R^4$ are as defined above and described in classes and subclasses herein.

In certain embodiments, one or more N-linked hydroxyl amine activating functional groups are selected from the group consisting of:

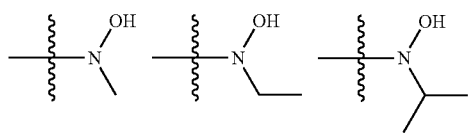

-continued

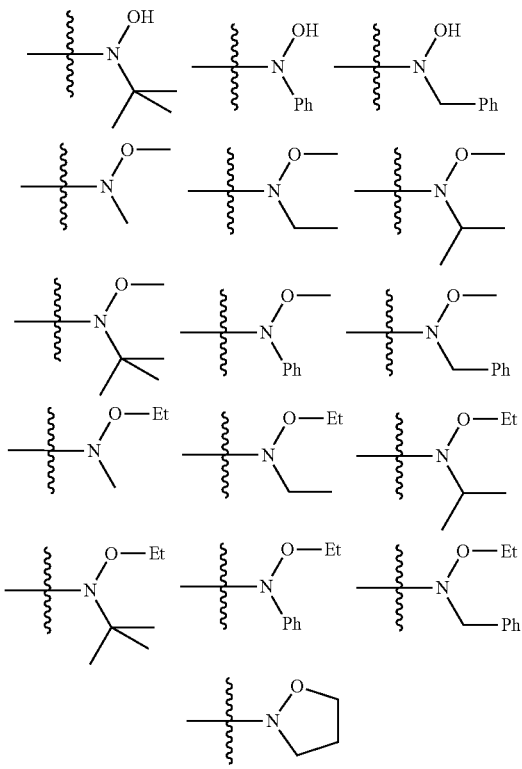

In some embodiments, an activating functional group in a provided metal complex is an amidine. In certain embodiments, such amidine activating functional groups are selected from:

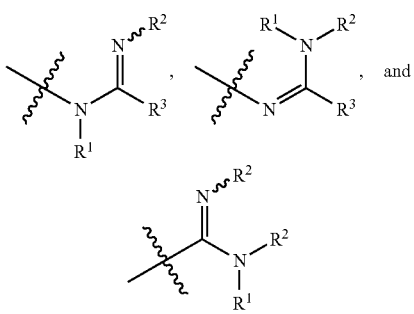

wherein each of $R^1$, $R^2$, and $R^3$ is as defined above and described in classes and subclasses herein.

In certain embodiments, an activating functional group is an N-linked amidine:

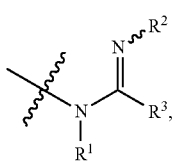

wherein each of $R^1$, $R^2$, and $R^3$ is as defined above and described in classes and subclasses herein. In certain embodiments, such N-linked amidine groups are selected from the group consisting of:

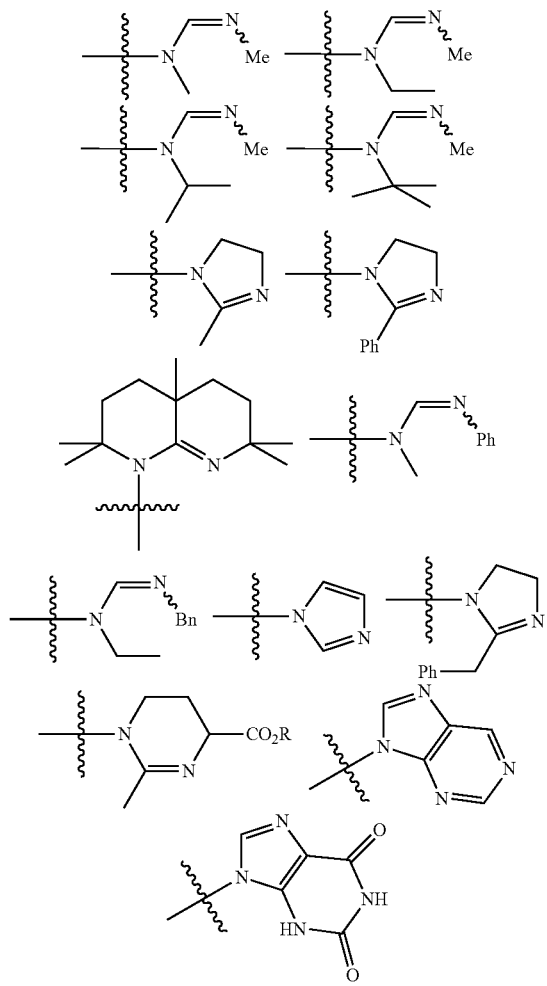

In certain embodiments, activating functional groups are amidine moieties linked through the imine nitrogen:

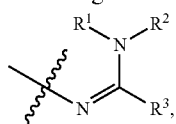

wherein each of $R^1$, $R^2$, and $R^3$ is as defined above and described in classes and subclasses herein. In certain embodiments, such imine-linked amidine activating functional groups are selected from the group consisting of:

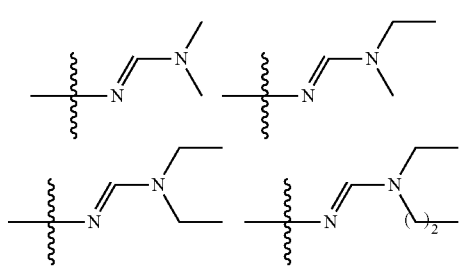

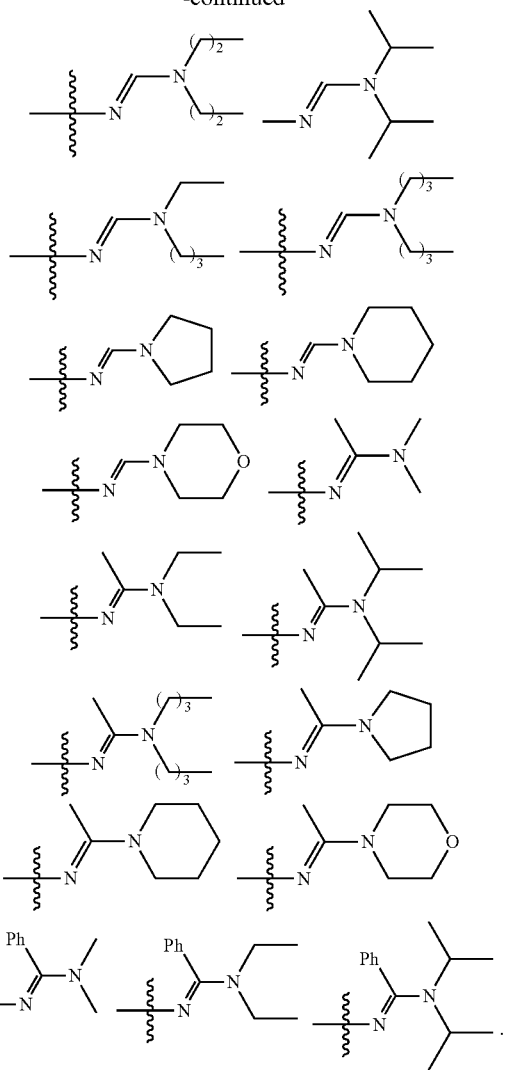

In certain embodiments, activating functional groups are amidine moieties linked through a carbon atom:

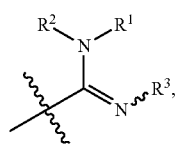

wherein each of $R^1$, $R^2$, and $R^3$ is as defined above and described in classes and subclasses herein. In certain embodiments, such carbon-linked amidine activating groups are selected from the group consisting of:

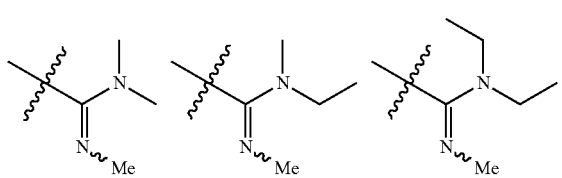

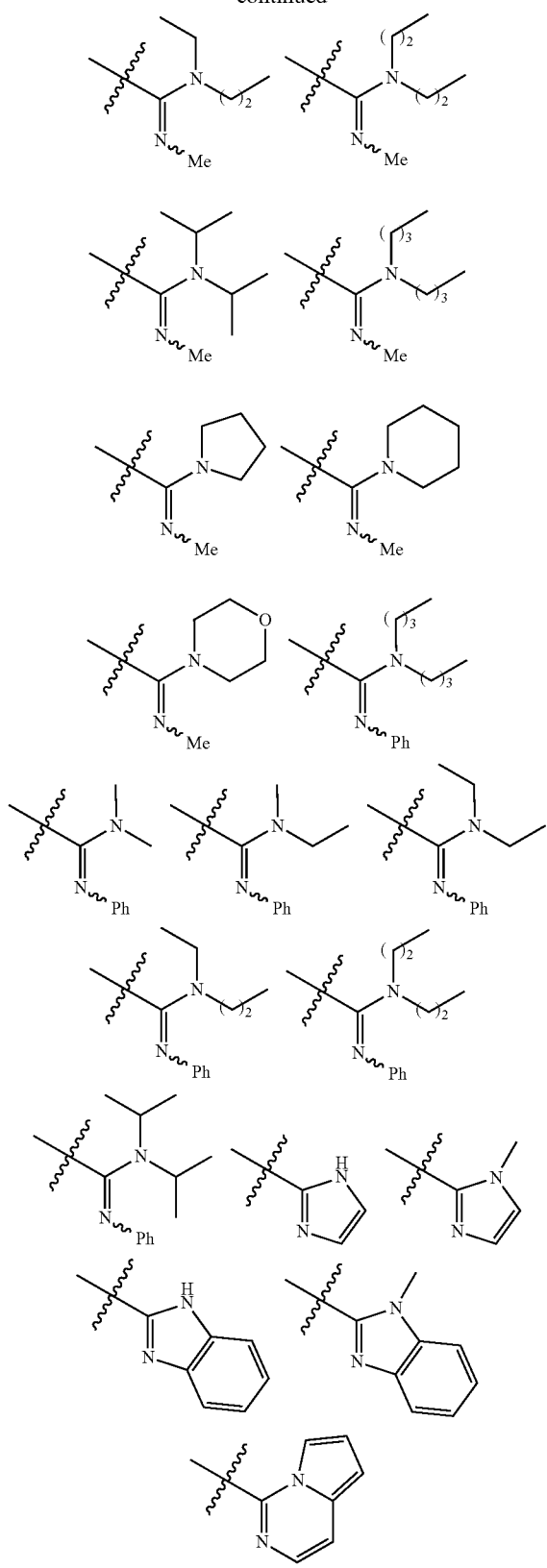

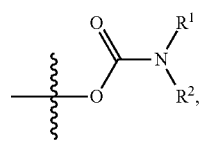

wherein each of $R^1$ and $R^2$ is as defined above and described in classes and subclasses herein. In some embodiments, a carbamate is O-linked:

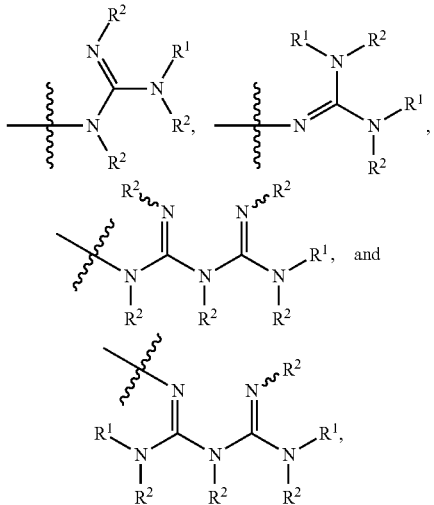

wherein each of $R^1$ and $R^2$ is as defined above and described in classes and subclasses herein.

In some embodiments, $R^2$ is selected from the group consisting of: methyl, t-butyl, t-amyl, benzyl, adamantyl, allyl, 4-methoxycarbonylphenyl, 2-(methylsulfonyl)ethyl, 2-(4-biphenylyl)-prop-2-yl, 2-(trimethylsilyl)ethyl, 2-bromoethyl, and 9-fluorenylmethyl.

In some embodiments, at least one activating functional group is a guanidine or bis-guanidine group:

wherein each $R^1$ and $R^2$ is as defined above and described in classes and subclasses herein.

In some embodiments, each $R^1$ and $R^2$ is independently hydrogen or optionally substituted $C_{1-20}$ aliphatic. In some embodiments, each $R^1$ and $R^2$ is independently hydrogen or optionally substituted $C_{1-10}$ aliphatic. In some embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In some embodiments, three or more $R^1$ and/or $R^2$ groups are taken together to form an optionally substituted fused ring system.

In some embodiments, one or more activating functional groups is a carbamate. In certain embodiments, a carbamate is N-linked:

In certain embodiments, where an activating functional group is a guanidine or bis guanidine moiety, it is selected from the group consisting of:

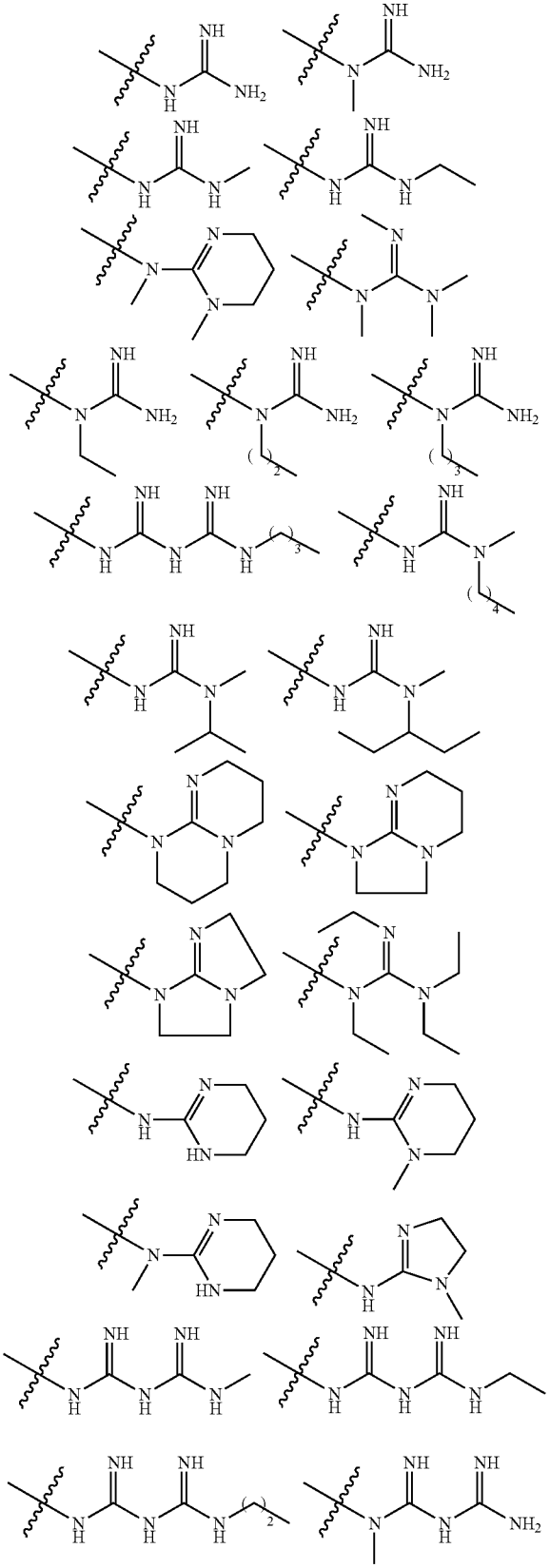

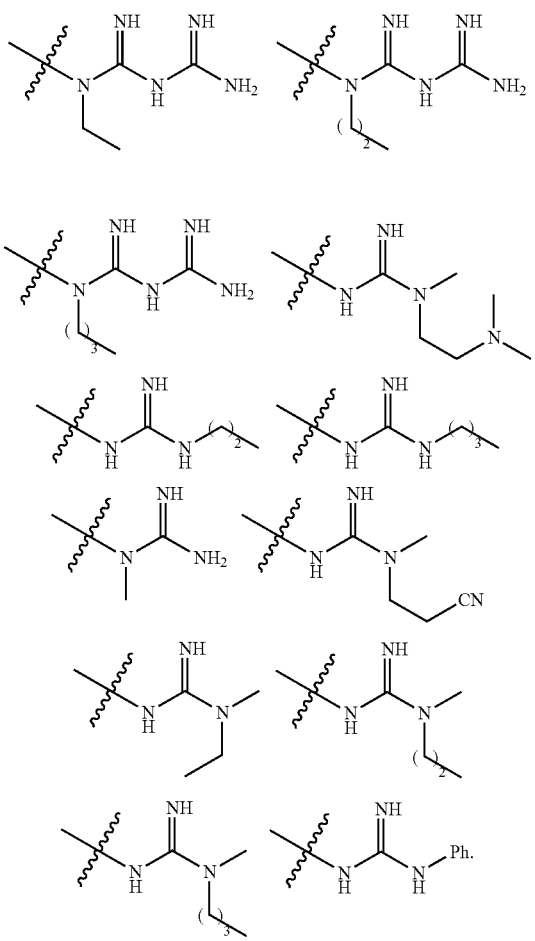

In some embodiments, an activating functional group is a urea:

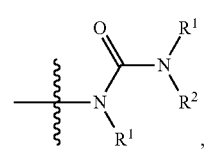

wherein each $R^1$ and $R^2$ is independently as defined above and described in classes and subclasses herein.

In certain embodiments, activating functional groups are oxime or hydrazone groups:

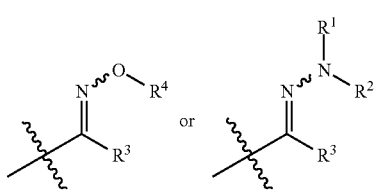

wherein each of $R^1$, $R^2$, $R^3$, and $R^4$ is as defined above and described in classes and subclasses herein.

In some embodiments, an activating functional group is an N-oxide derivative:

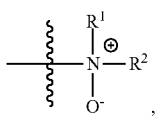

wherein each of $R^1$ and $R^2$ is as defined above and described in classes and subclasses herein.

In certain embodiments, an N-oxide activating functional group is selected from the group consisting of:

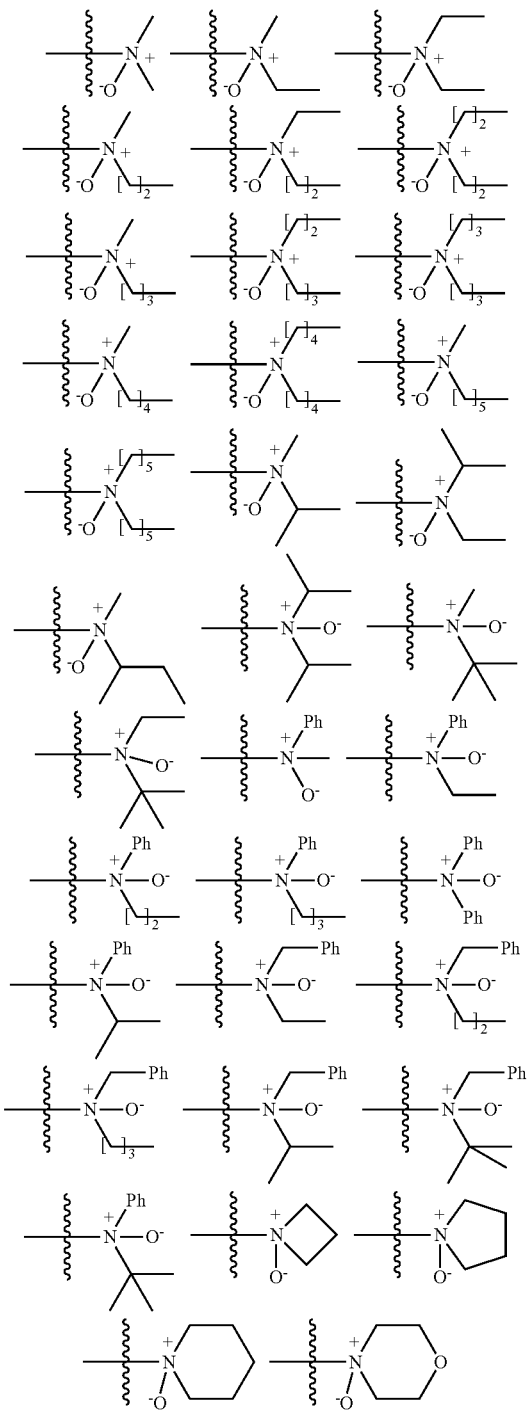

-continued

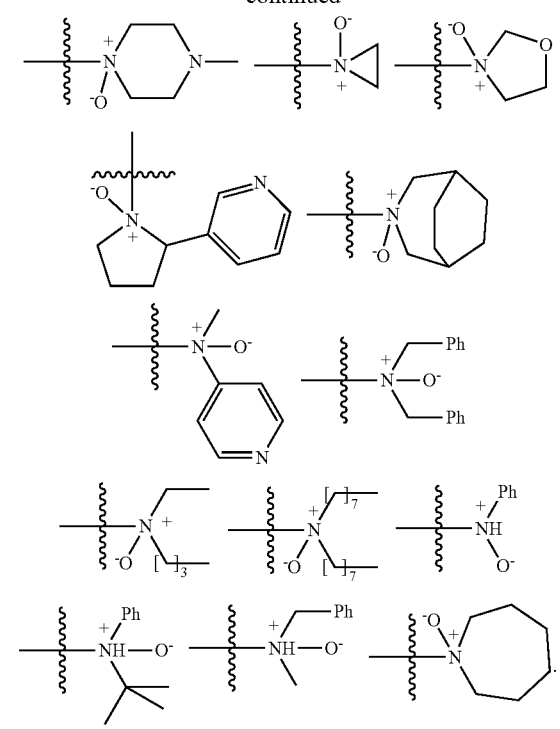

II.b. Cationic Activating Groups

In some embodiments, one or more tethered activating functional groups on provided metal complexes comprise a cationic moiety. In some embodiments, a cationic moiety is selected from a structure in Table Z-2:

TABLE Z-2

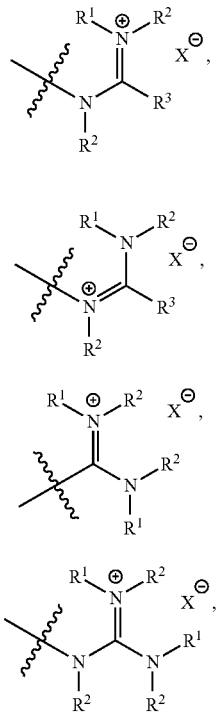

TABLE Z-2-continued

TABLE Z-2-continued

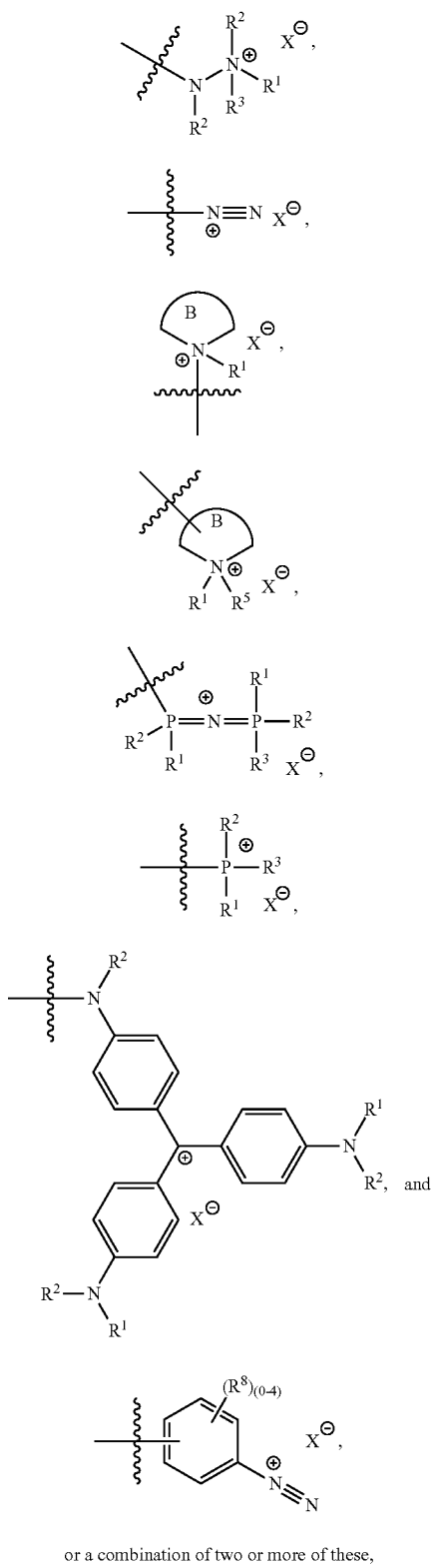

or a combination of two or more of these, wherein:
  each of $R^1$, $R^2$, and $R^3$ is independently as defined above and described in classes and subclasses herein, both singly and in combination;

$R^5$ is $R^2$ or hydroxyl; wherein $R^1$ and $R^5$ can be taken together with intervening atoms to form one or more optionally substituted carbocyclic, heterocyclic, aryl, or heteroaryl rings;

each $R^6$ and $R^7$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^6$ and $R^7$ can be taken together with intervening atoms to form one or more optionally substituted rings optionally containing one or more heteroatoms, and an $R^6$ and $R^7$ group can be taken with an $R^1$ or $R^2$ group to form one or more optionally substituted rings;

each occurrence of $R^8$ is independently selected from the group consisting of: halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-N_3$, $-OR^7$, $-OC(O)N(R^y)_2$, $-N(R^y)_2$, $-NR^yC(O)R^y$, $-NR^yC(O)OR^y$; or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein each $R^y$ is independently as defined above and described in classes and subclasses herein, and where two or more adjacent $R^8$ groups can be taken together to form an optionally substituted saturated, partially unsaturated, or aromatic 5- to 12-membered ring containing 0 to 4 heteroatoms;

$X^-$ is any anion;

Ring A is an optionally substituted, 5- to 10-membered heteroaryl group; and

Ring B is an optionally substituted, 3- to 8-membered saturated or partially unsaturated monocyclic heterocyclic ring having 0-2 heteroatoms in addition to the depicted ring nitrogen atom independently selected from nitrogen, oxygen, or sulfur.

In certain embodiments, a cationic activating functional group is a protonated amine:

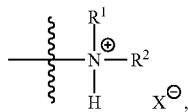

where each of R¹ and R² is as defined above and described in classes and subclasses herein.

In specific embodiments, a protonated amine activating functional group is selected from the group consisting of:

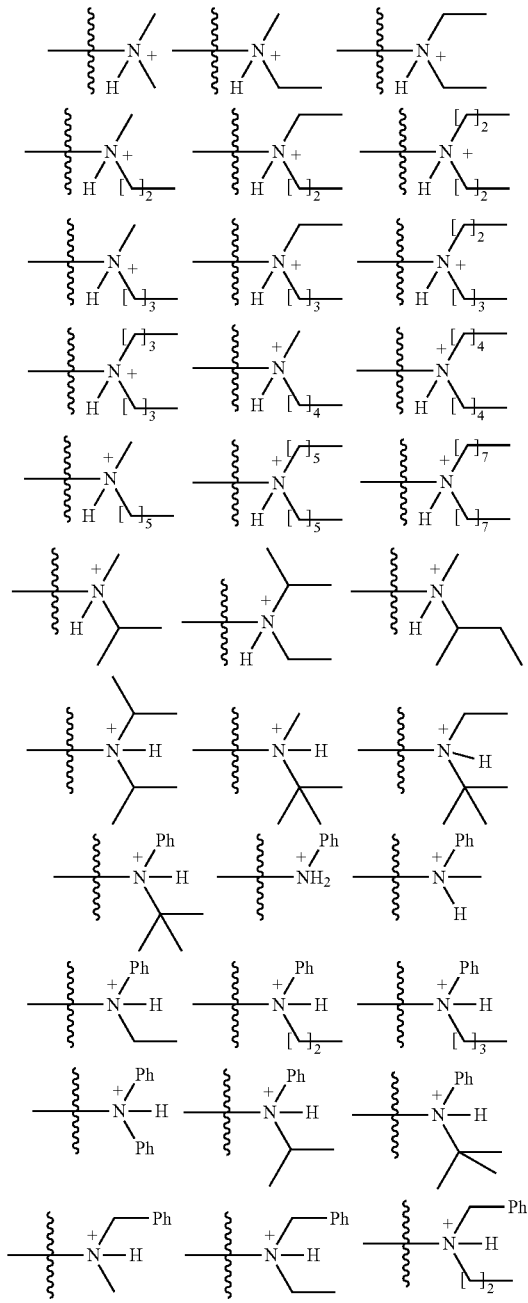

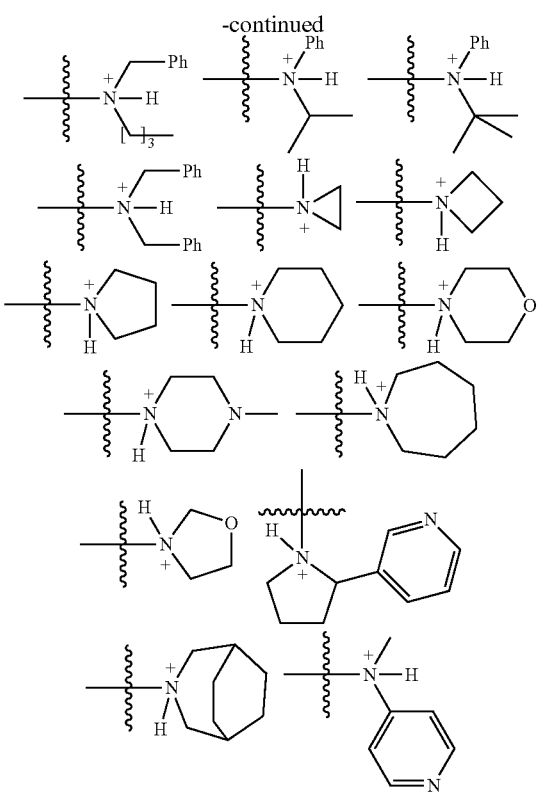

In certain embodiments, an activating functional group is a guanidinium group:

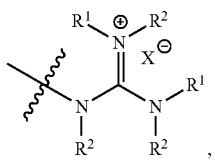

wherein each R¹ and R² is independently as defined above and described in classes and subclasses herein. In some embodiments, each R¹ and R² is independently hydrogen or optionally substituted $C_{1-20}$ aliphatic. In some embodiments, each R¹ and R² is independently hydrogen or optionally substituted $C_{1-10}$ aliphatic. In some embodiments, each R¹ and R² is independently hydrogen or $C_{1-12}$ aliphatic. In some embodiments, each R¹ and R² is independently hydrogen or $C_{1-20}$ heteroaliphatic. In some embodiments, each R¹ and R² is independently hydrogen or phenyl. In some embodiments, each R¹ and R² is independently hydrogen or 8- to 10-membered aryl. In some embodiments, each R¹ and R² is independently hydrogen or 5- to 10-membered heteroaryl. In some embodiments, each R¹ and R² is independently hydrogen or 3- to 7-membered heterocyclic. In some embodiments, one or more of R¹ and R² is optionally substituted $C_{1-12}$ aliphatic.

In some embodiments, any two or more R¹ or R² groups are taken together with intervening atoms to form one or more optionally substituted carbocyclic, heterocyclic, aryl, or heteroaryl rings. In certain embodiments, R¹ and R² groups are taken together to form an optionally substituted 5- or 6-membered ring. In some embodiments, three or more R¹ and/or R² groups are taken together to form an optionally substituted fused ring system.

In certain embodiments, a $R^1$ and $R^2$ group are taken together with intervening atoms to form a compound selected from:

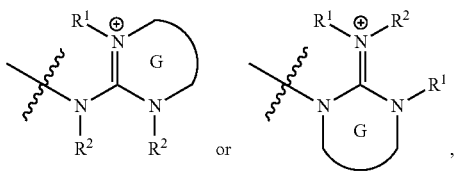

wherein each $R^1$ and $R^2$ is independently as defined above and described in classes and subclasses herein, and Ring G is an optionally substituted 5- to 7-membered saturated or partially unsaturated heterocyclic ring.

It will be appreciated that when a guanidinium cation is depicted as

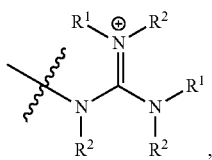

all such resonance forms are contemplated and encompassed by the present disclosure. For example, such groups can also be depicted as

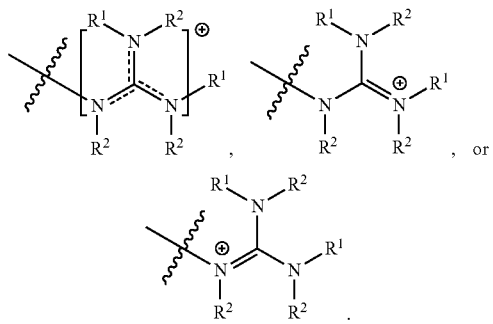

In specific embodiments, a guanidinium activating functional group is selected from the group consisting of:

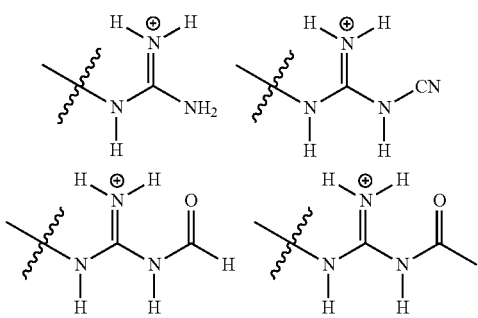

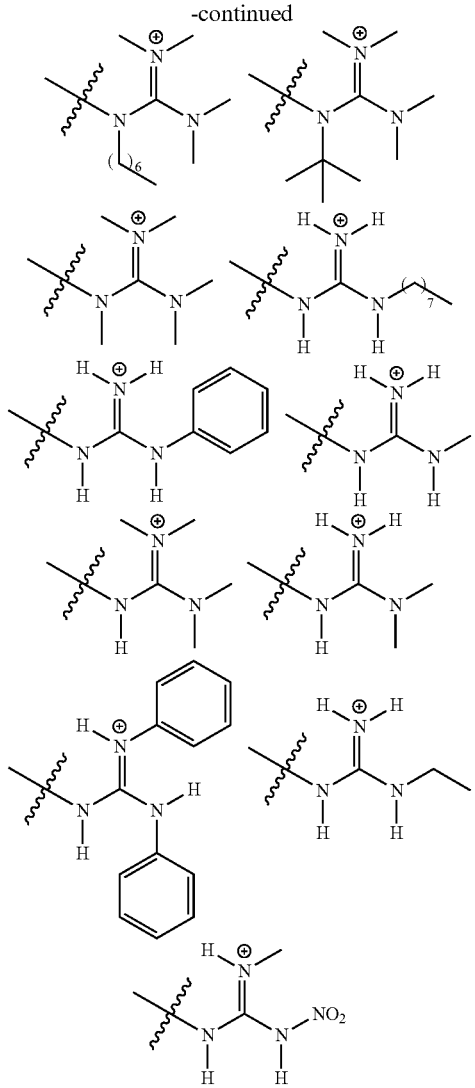

In some embodiments, an activating functional group is a sulfonium group or an arsonium group:

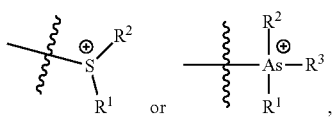

wherein each of $R^1$, $R^2$, and $R^3$ are as defined above and described in classes and subclasses herein.

In specific embodiments, an arsonium activating functional group is selected from the group consisting of:

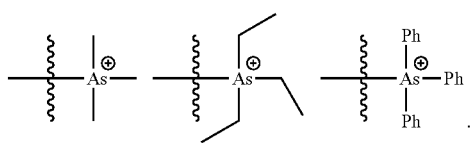

In some embodiments, an activating functional group is an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In some embodiments, a nitrogen-containing heterocycle includes a quaternarized nitrogen atom. In certain embodiments, a nitrogen-containing heterocycle includes an iminium moiety such as

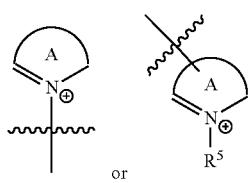

or

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In some embodiments, a ring nitrogen to which the attachment is made is thereby quaternized, and in some embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In some embodiments, an activating functional group is

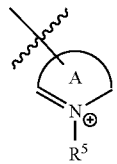

In certain embodiments, ring A is an optionally substituted, 5- to 10-membered heteroaryl group. In some embodiments, Ring A is an optionally substituted, 6-membered heteroaryl group. In some embodiments, Ring A is a ring of a fused heterocycle. In some embodiments, Ring A is an optionally substituted pyridyl group.

In some embodiments, when Z is

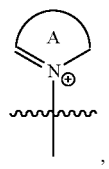

ring A is other than an imidazole, an oxazole, or a thiazole.

In specific embodiments, a nitrogen-containing heterocycle activating functional group is selected from the group consisting of:

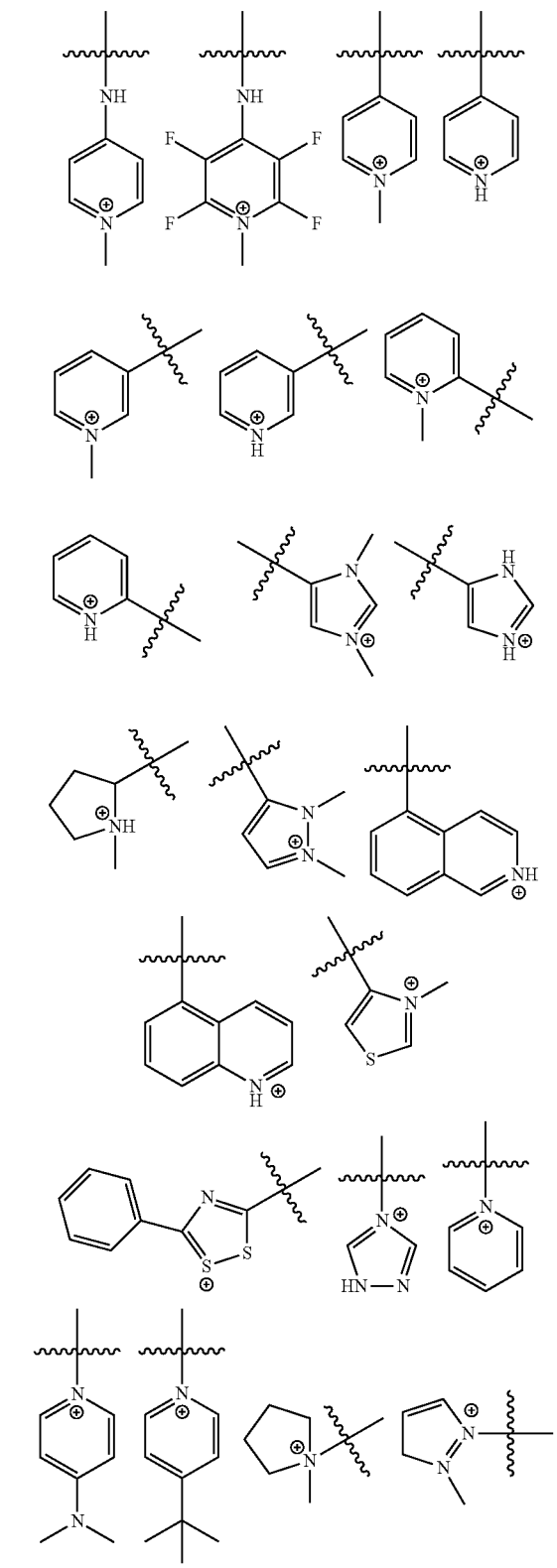

-continued

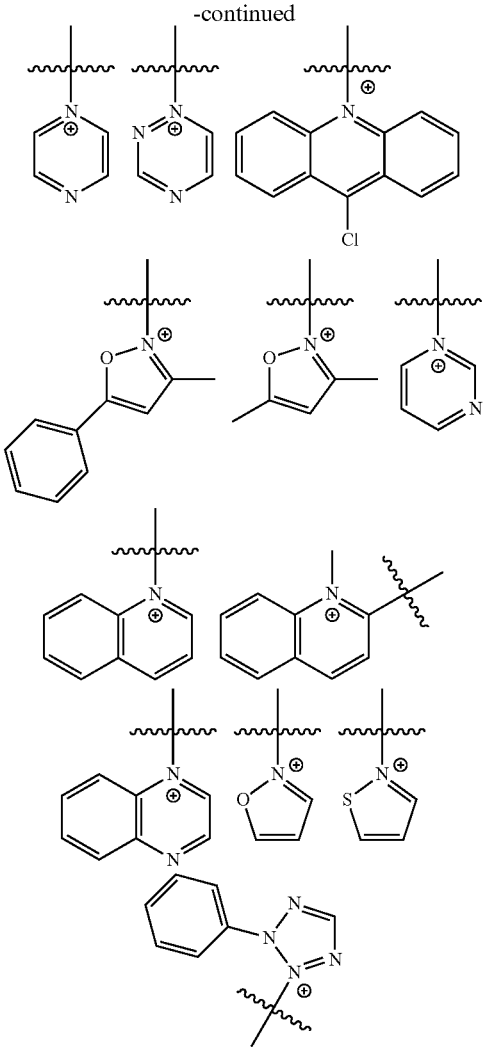

In certain embodiments, Ring B is a 5-membered saturated or partially unsaturated monocyclic heterocyclic ring. In certain embodiments, Ring B is a 6-membered saturated or partially unsaturated heterocycle. In certain embodiments, Ring B is a 7-membered saturated or partially unsaturated heterocycle. In certain embodiments, Ring B is tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. In some embodiments, Ring B is piperidinyl.

In some embodiments, an activating functional group is

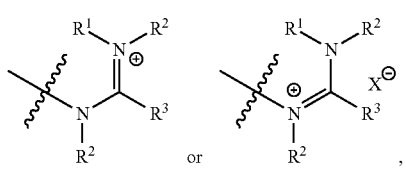

where each $R^1$, $R^2$, and $R^3$ is independently as defined above and described in classes and subclasses herein.

In some embodiments, an activating functional group is

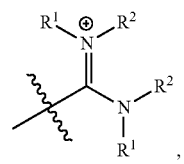

wherein each $R^1$ and $R^2$ is independently as defined above and described in classes and subclasses herein.

In some embodiments, an activating functional group is

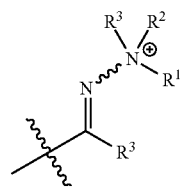

wherein each $R^1$, $R^2$, and $R^3$ is independently as defined above and described in classes and subclasses herein.

In some embodiments, an activating functional group is

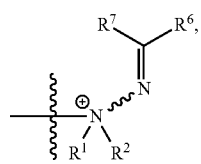

wherein each of $R^1$, $R^2$, $R^6$, and $R^7$ is as defined above and described in classes and subclasses herein.

In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In some embodiments, $R^6$ and $R^7$ are each independently an optionally substituted $C_{1-20}$ aliphatic. In some embodiments, $R^6$ and $R^7$ are each independently an optionally substituted $C_{1-20}$ heteroaliphatic having. In some embodiments, $R^6$ and $R^7$ are each independently an optionally substituted phenyl or 8-10-membered aryl. In some embodiments, $R^6$ and $R^7$ are each independently an optionally substituted 5- to 10-membered heteroaryl. In some embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In some embodiments, $R^6$ and $R^7$ are each independently an optionally substituted $C_{1-6}$ aliphatic. In some embodiments, each occurrence of $R^6$ and $R^7$ is independently methyl, ethyl, propyl, butyl, pentyl, hexyl, heptyl, octyl, or benzyl. In some embodiments, each occurrence of $R^6$ and $R^7$ is independently perfluoro. In some embodiments, each occurrence of $R^6$ and $R^7$ is independently —$CF_2CF_3$.

In some embodiments, an activating functional group is

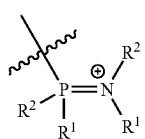

wherein each R¹ and R² is independently as defined above and described in classes and subclasses herein, both singly and in combination.

In some embodiments, an activating functional group is

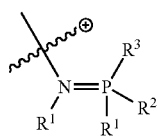

wherein each $R^1$, $R^2$, and $R^3$ is independently as defined above and described in classes and subclasses herein.

In some embodiments, an activating functional group is

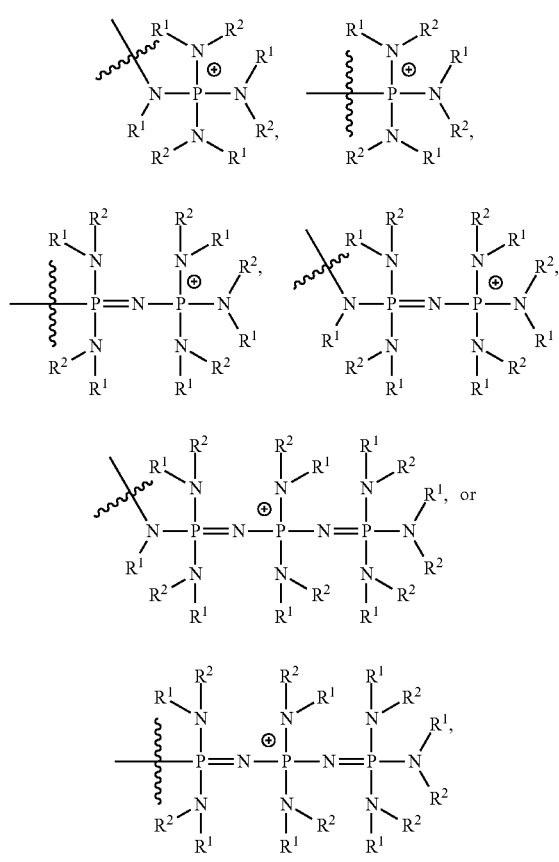

wherein each R¹ and R² is independently as defined above and described in classes and subclasses herein.

In some embodiments, an activating functional group is

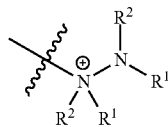

wherein each R¹ and R² is independently as defined above and described in classes and subclasses herein.

In some embodiments, an activating functional group is

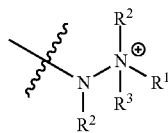

wherein each $R^1$, $R^2$, and $R^3$ is independently as defined above and described in classes and subclasses herein.

In some embodiments, an activating functional group is

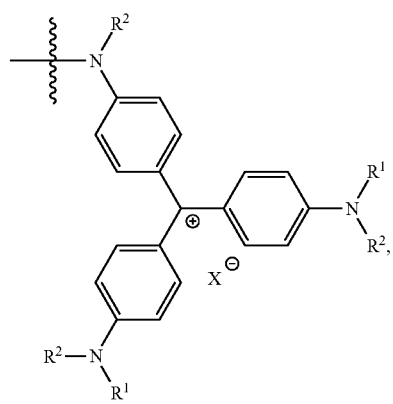

wherein each R¹ and R² is independently as defined above and described in classes and subclasses herein.

II.c. Phosphorous-Containing Activating Groups

In some embodiments, activating functional groups Z are phosphorous containing groups.

In certain embodiments, a phosphorous-containing functional group is chosen from the group consisting of: phosphines ($-PR^y_2$); Phosphine oxides $-P(O)R^y_2$; phosphinites $P(OR^4)R^y_2$; phosphonites $P(OR^4)_2R^y$; phosphites $P(OR^4)_3$; phosphinates $OP(OR^4)R^y_2$; phosphonates; $OP(OR^4)_2R^y$; phosphates $-OP(OR^4)_3$; phosphonium salts $([-PR^y_3]^+)$ where a phosphorous-containing functional group may be linked to a metal complex through any available position (e.g. direct linkage via the phosphorous atom, or in some cases via an oxygen atom).

In certain embodiments, a phosphorous-containing functional group is chosen from the group consisting of:

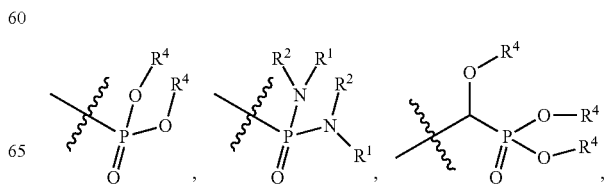

-continued

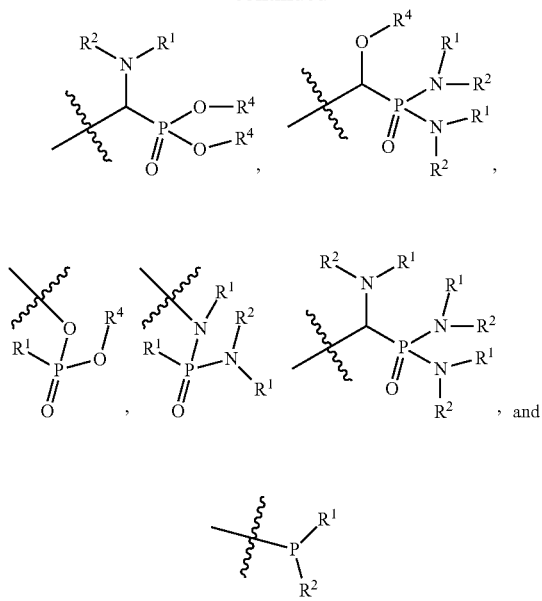

or a combination of two or more of these
wherein each $R^1$, $R^2$, and $R^4$ is as defined above and described in classes and subclasses herein, both singly and in combination; and where two $R^4$ groups can be taken together with intervening atoms to form an optionally substituted ring optionally containing one or more heteroatoms, or an $R^4$ group can be taken with an $R^1$ or $R^2$ group to an optionally substituted carbocyclic, heterocyclic, heteroaryl, or aryl ring.

In some embodiments, phosphorous containing functional groups include those disclosed in *The Chemistry of Organophosphorus Compounds. Volume 4. Ter- and Quinquevalent Phosphorus Acids and their Derivatives. The Chemistry of Functional Group Series* Edited by Frank R. Hartley (Cranfield University, Cranfield, U.K.). Wiley: New York. 1996. ISBN 0-471-95706-2, the entirety of which is hereby incorporated herein by reference.

In certain embodiments, phosphorous containing functional groups have the formula:

$$-(V)_b-[(R^9R^{10}R^{11}P)^+]_{n'}W^{n'-}, \text{ wherein:}$$

V is —O—, —N=, or —$NR^z$—, b is 1 or 0, each of $R^9$, $R^{10}$ and $R^{11}$ are independently present or absent and, if present, are independently selected from the group consisting of optionally substituted $C_1$-$C_{20}$ aliphatic, optionally substituted phenyl, optionally substituted $C_8$-$C_{14}$ aryl, optionally substituted 3- to 14-membered heterocyclic, optionally substituted 5- to 14-membered heteroaryl, halogen, =O, —$OR^z$, =$NR^z$, and $N(R^z)_2$ where $R^z$ is hydrogen, or an optionally substituted $C_1$-$C_{20}$ aliphatic, optionally substituted phenyl, optionally substituted 8- to 14-membered aryl, optionally substituted 3- to 14-membered heterocyclic, or optionally substituted 5- to 14-membered heteroaryl, W is any anion, and n' is an integer between 1 and 4.

In some embodiments, an activating functional group is a phosphonate group:

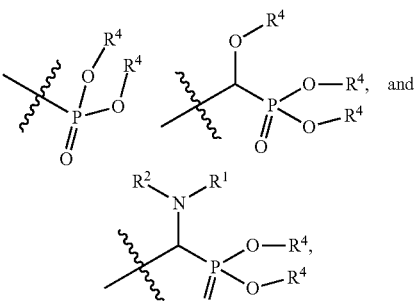

wherein each $R^1$, $R^2$, and $R^4$ is independently as defined above and described in classes and subclasses herein, both singly and in combination.

In specific embodiments, a phosphonate activating functional group is selected from the group consisting of:

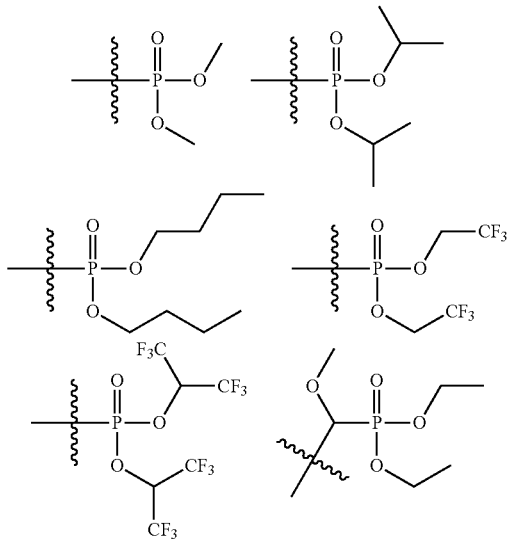

In some embodiments, an activating functional group is a phosphonic diamide group:

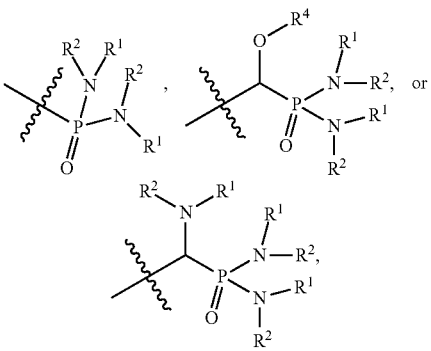

wherein each $R^1$, $R^2$, and $R^4$ is independently as defined above and described in classes and subclasses herein. In certain embodiments, each $R^1$ and $R^2$ group in a phosphonic diamide is methyl.

In some embodiments, an activating functional group is a phosphine group:

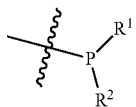

wherein $R^1$, and $R^2$ are as defined above and described in classes and subclasses herein, both singly and in combination.

In specific embodiments, a phosphine activating functional group is selected from the group consisting of:

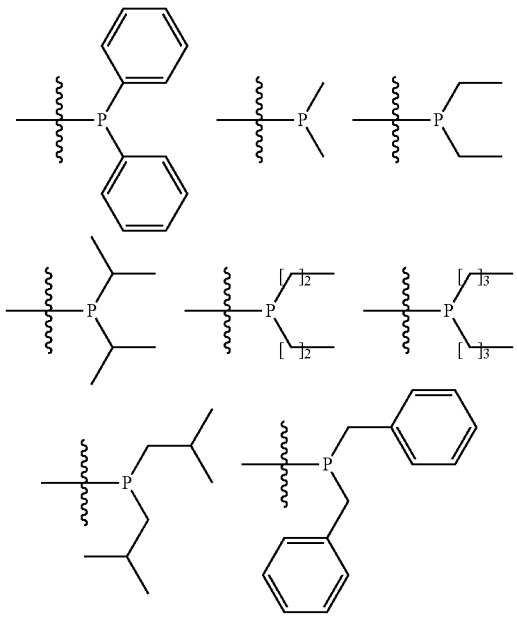

IId. Counterions

In certain embodiments, X is any anion. In certain embodiments, X is a nucleophile. In some embodiments, X is a nucleophile capable of ring opening an epoxide. In certain embodiments, X is absent. In certain embodiments, X is a nucleophilic ligand. Exemplary nucleophilic ligands include, but are not limited to, —$OR^x$, —$SR^x$, —$O(C=O)R^x$, —$O(C=O)OR^x$, —$O(C=O)N(R^x)_2$, —$N(R^x)(C=O)R^x$, —NC, —CN, halo (e.g., —Br, —I, —Cl), —$N_3$, —$O(SO_2)R^x$ and —$OPR^x_3$, wherein each $R^x$ is, independently, selected from hydrogen, optionally substituted aliphatic, optionally substituted heteroaliphatic, optionally substituted aryl and optionally substituted heteroaryl.

In certain embodiments, X is —$O(C=O)R^x$, wherein $R^x$ is selected from optionally substituted aliphatic, fluorinated aliphatic, optionally substituted heteroaliphatic, optionally substituted aryl, fluorinated aryl, and optionally substituted heteroaryl.

For example, in certain embodiments, X is —$O(C=O)R^x$, wherein $R^x$ is optionally substituted aliphatic. In certain embodiments, X is —$O(C=O)R^x$, wherein $R^x$ is optionally substituted alkyl and fluoroalkyl. In certain embodiments, X is —$O(C=O)CH_3$ or —$O(C=O)CF_3$.

Furthermore, in certain embodiments, X is —$O(C=O)R^x$, wherein $R^x$ is optionally substituted aryl, fluoroaryl, or heteroaryl. In certain embodiments, X is —$O(C=O)R^x$, wherein $R^x$ is optionally substituted aryl. In certain embodiments, X is —$O(C=O)R^x$, wherein $R^x$ is optionally substituted phenyl. In certain embodiments, X is —$O(C=O)C_6H_5$ or —$O(C=O)C_6F_5$.

In certain embodiments, X is —$OR^x$, wherein $R^x$ is selected from optionally substituted aliphatic, optionally substituted heteroaliphatic, optionally substituted aryl, and optionally substituted heteroaryl.

For example, in certain embodiments, X is —$OR^x$, wherein $R^x$ is optionally substituted aryl. In certain embodiments, X is —$OR^x$, wherein $R^x$ is optionally substituted phenyl. In certain embodiments, X is —$OC_6H_5$ or —$OC_6H_2(2,4-NO_2)$.

In certain embodiments, X is halo. In certain embodiments, X is —Br. In certain embodiments, X is —Cl. In certain embodiments, X is —I.

In certain embodiments, X is —$O(SO_2)R^x$. In certain embodiments X is —OTs. In certain embodiments X is —$OSO_2Me$. In certain embodiments X is —$OSO_2CF_3$. In some embodiments, X is a 2,4-dinitrophenolate anion.

In some embodiments, wherein X is selected from the group consisting of chlorine, bromine, an optionally substituted $C_{1-12}$ carboxylate, azide, an optionally substituted phenoxide, a sulfonate salt, and a combination of any two or more of these.

In some embodiments, X is carbonate. In some embodiments, X is bicarbonate.

In some embodiments, X is selected from the group consisting of chloride, acetate, trifluoroacetate, azide, pentafluorobenzoate, and a nitrophenolate.

In some embodiments, the present invention provides metal complexes and methods of using the same, wherein:

i) at least one activating group is

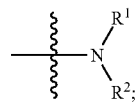

ii) at least one activating group is

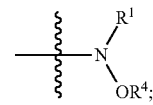

iii) at least one activating group is

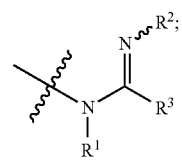

iv) at least one activating group is

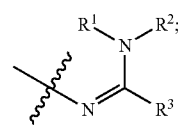

v) at least one activating group is

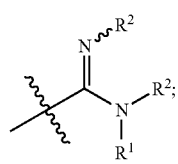

vi) at least one activating group is

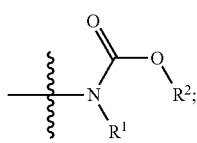

vii) at least one activating group is

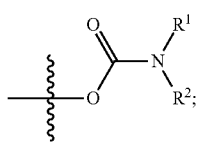

viii) at least one activating group is selected from the group consisting of

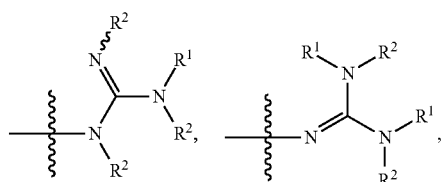

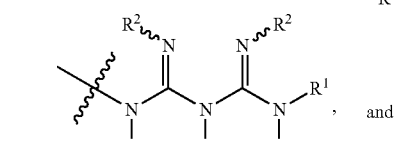

ix) at least one activating group is

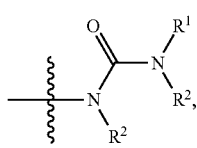

x) at least one activating group is

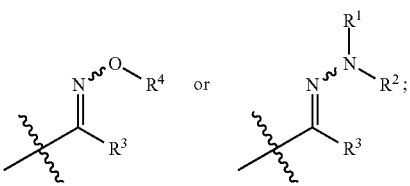

xi) at least one activating group is

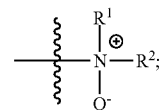

xii) at least one activating group is

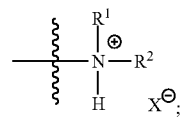

xiii) at least one activating group is

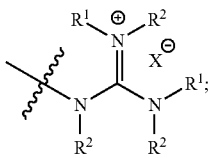

xiv) at least one activating group is

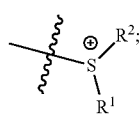

xv) at least one activating group is

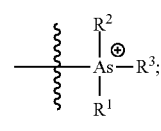

xvi) at least one activating group is

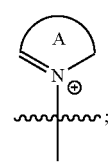

xvii) at least one activating group is

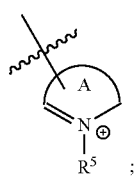

xviii) at least one activating group is

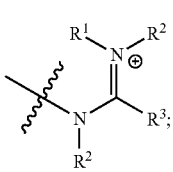

xix) at least one activating group is

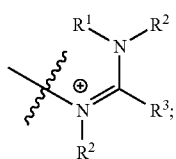

xx) at least one activating group is

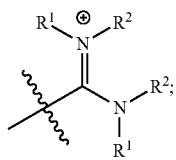

xxi) at least one activating group is

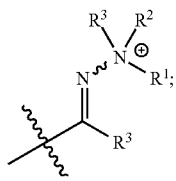

xxii) at least one activating group is

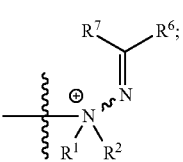

xxiii) at least one activating group is

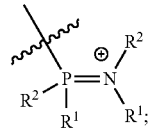

xxiv) at least one activating group is

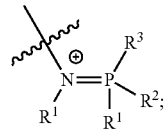

xxv) at least one activating group is

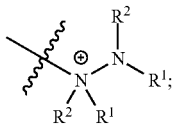

xxvi) at least one activating group is

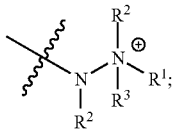

xxvii) at least one activating group is

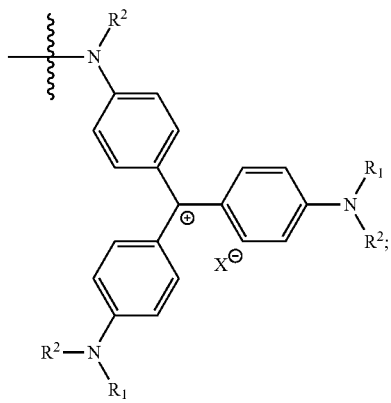

xxviii) at least one activating group is

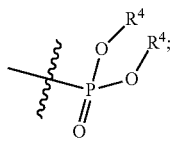

xxix) at least one activating group is

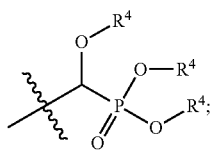

xxx) at least one activating group is

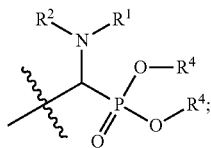

xxxi) at least one activating group is

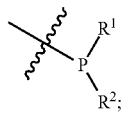

xxxii) for subsets i) through xxxi), each $R^1$ group is the same;

xxxiii) for subsets i) through xxxi), each $R^1$ group is hydrogen;

xxxiv) for subsets i) through xxxi), at least one $R^1$ group is different from other $R^1$ groups;

xxxv) for subsets i) through xxxi), $R^1$ is optionally substituted $C_{1-20}$ aliphatic;

xxxvi) for subsets i) through xxxi), each $R^1$ is independently hydrogen, —$CF_2CF_3$, methyl, ethyl, propyl, butyl, pentyl, hexyl, heptyl, octyl, optionally substituted phenyl, or optionally substituted benzyl;

xxxvii) for subsets i) through xxxvi), each $R^2$ group is the same;

xxxviii) for subsets i) through xxxvi), each $R^2$ group is hydrogen;

xxxix) for subsets i) through xxxvi), at least one $R^2$ group is different from other $R^2$ groups;

xl) for subsets i) through xxxvi), $R^2$ is optionally substituted $C_{1-20}$ aliphatic;

xli) for subsets i) through xxxvi), each $R^2$ is independently hydrogen, —$CF_2CF_3$, methyl, ethyl, propyl, butyl, pentyl, hexyl, heptyl, octyl, optionally substituted phenyl, or optionally substituted benzyl;

xlii) for subsets i) through xli), $R^1$ and $R^2$ are the same;

xliii) for subsets i) through xli) $R^1$ and $R^2$ are taken together with intervening atoms to form one or more optionally substituted carbocyclic, heterocyclic, aryl, or heteroaryl rings;

xliv) for any of subsets i) through xliii) having $R^3$, $R^3$ is hydrogen;

xlv) for any of subsets i) through xliii) having $R^3$, $R^3$ is optionally substituted $C_{1-20}$ aliphatic;

xlvi) for any of subsets i) through xliii) having $R^3$, $R^3$ is independently hydrogen, —$CF_2CF_3$, methyl, ethyl, propyl, butyl, pentyl, hexyl, heptyl, octyl, optionally substituted phenyl, or optionally substituted benzyl;

xlvii) for any of subsets i) through xliii) having $R^3$, one or more $R^1$ or $R^2$ groups are taken together with $R^3$ and intervening atoms to form an optionally substituted heterocyclic or heteroaryl ring;

xlviii) for any of subsets i) through xlviii) having $R^4$, $R^4$ is hydrogen;

xlix) for any of subsets i) through xlviii) having $R^4$, $R^4$ is optionally substituted $C_{1-12}$ aliphatic;

l) for any of subsets i) through xlviii) having $R^4$, $R^1$ and $R^4$ are taken together with intervening atoms to form one or more optionally substituted heterocyclic or heteroaryl rings optionally containing one or more additional heteroatoms;

li) for subsets xvi) and xvii), Ring A is a 5- to 6-membered heteroaryl group;

lii) for subset li), $R^5$ is hydroxyl;

liii) for subset li), $R^5$ is optionally substituted $C_{1-20}$ aliphatic;

liv) for subsets i) through xxxi) where an activating group is cationic, X is acetate;

lv) for subsets i) through xxxi) where an activating group is cationic, X is trifluoroacetate;

lvi) for subsets i) through xxxi) where an activating group is cationic, X is optionally substituted benzoate;

lvii) for subsets i) through xxxi) where an activating group is cationic, X is phenoxide;

lviii) for subsets i) through xxxi) where an activating group is cationic, X is dinitrophenoxide;

lvix) for subsets i) through xxxi) where an activating group is cationic, X is halo.

It will be appreciated that for each of the classes and subclasses described above and herein, all possible combinations of the variables described in subsets i) through lvix) above are contemplated by the present invention. Thus, the invention encompasses any and all compounds of the formula described above and herein, and subclasses thereof, generated by taking any possible combination of variables set forth herein (including, but not limited to subsets i) through lvix)).

III. Metal Complexes

In some embodiments, for provided metal complexes each

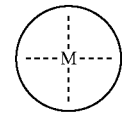

comprises:

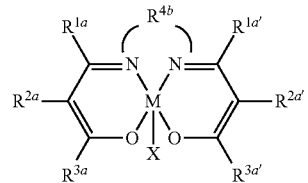

$R^{1a}$, $R^{1a'}$, $R^{2a}$, $R^{2a'}$, $R^{3a}$, and $R^{3a'}$ are independently a —⌇⌇($Z$)$_m$ group, a linker, hydrogen, —OR, —$NR_2$, —SR, —CN, —$NO_2$, —$SO_2R$, —SOR, —$SO_2NR_2$; —CNO, —$NRSO_2R$, —NCO, —$N_3$, —$SiR_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where any of [$R^{2a'}$ and $R^{3a}$], [$R^{2a}$ and $R^{3a}$], [$R^{1a}$ and $R^{2a}$], and [$R^{1a'}$ and $R^{2a'}$] may optionally be taken together with intervening atoms to form one or more rings which may in turn be substituted with one or more $R^d$ groups;

$R^d$ at each occurrence is independently a —$\sim$($Z$)$_m$ group, a linker, a portion of a linker that is connected to another oligomeric unit, a moiety capable of forming a linker, hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more $R^d$ groups may be taken together with intervening atoms to form one or more optionally substituted rings optionally containing one or more heteroatoms, $R^{4b}$ is selected from the group consisting of:

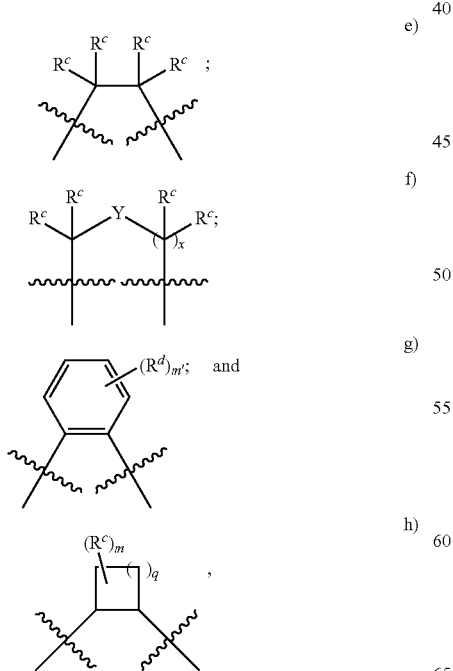

where $R^c$ at each occurrence is independently a —$\sim$($Z$)$_m$ group, a linker, hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more $R^c$ groups may be taken together with the carbon atoms to which they are attached and any intervening atoms to form one or more optionally substituted rings; when two $R^c$ groups are attached to the same carbon atom, they may optionally be taken together along with the carbon atom to which they are attached to form an optionally substituted moiety selected from the group consisting of: a 3- to 8-membered spirocyclic ring, a carbonyl, an oxime, a hydrazone, and an imine;

R at each occurrence is independently hydrogen, an optionally substituted radical selected the group consisting of acyl; $C_{1-6}$ aliphatic; $C_{1-6}$ heteroaliphatic; carbamoyl; arylalkyl; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring, X is an anion;

Y is a divalent linker selected from the group consisting of: —NR—, —N(R)C(O)—, —C(O)NR—, —O—, —C(O)—, —OC(O)—, —C(O)O—, —S—, —SO—, —SO$_2$—, —SiR$_2$—, —C(=S)—, —C(=NR)—, or —N=N—; a polyether; a $C_3$ to $C_8$ substituted or unsubstituted carbocycle; and a $C_1$ to $C_8$ substituted or unsubstituted heterocycle;

m is 0 or an integer from 1 to 6, inclusive;

m' is 0 or an integer from 1 to 4, inclusive;

q is 0 or an integer from 1 to 4, inclusive; and x is 0, 1, or 2.

In certain embodiments, oligomeric catalysts of the present invention comprise metal complexes selected from the group consisting of:
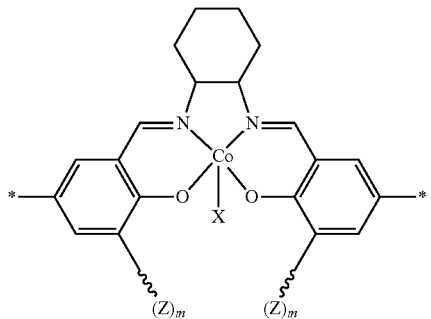
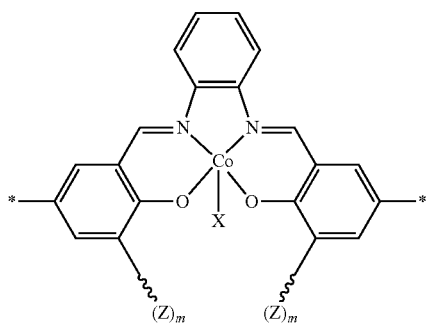
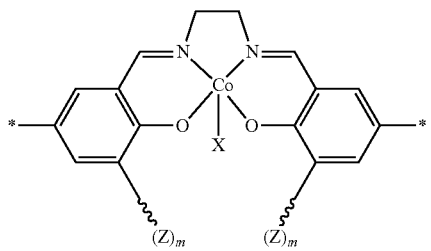
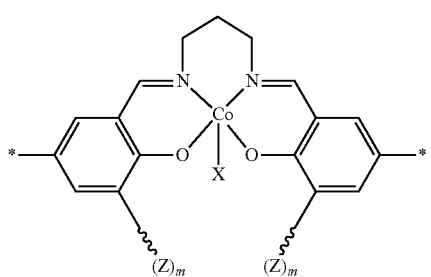
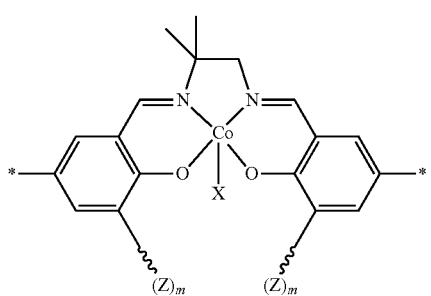
-continued
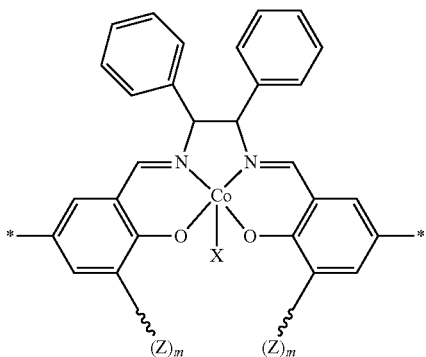
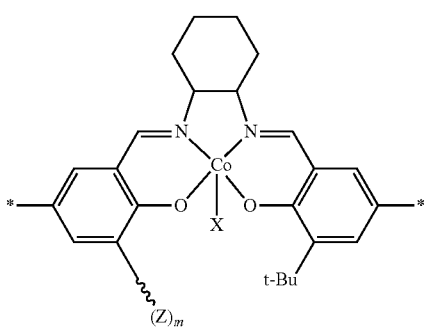
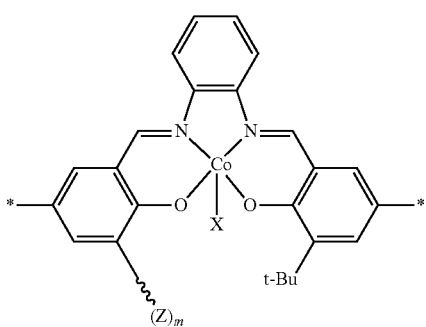
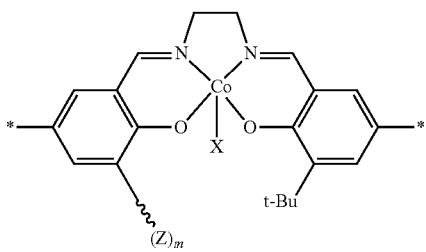
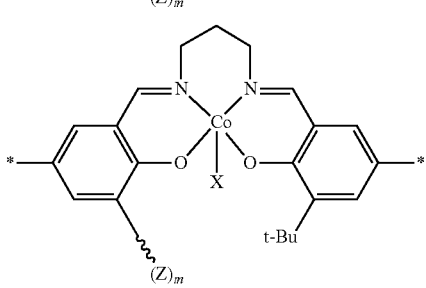

105
-continued
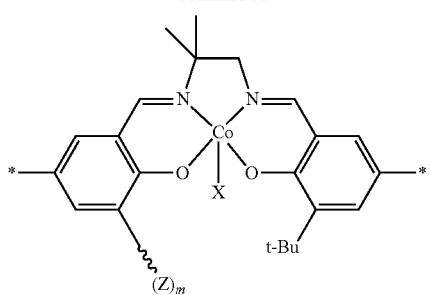
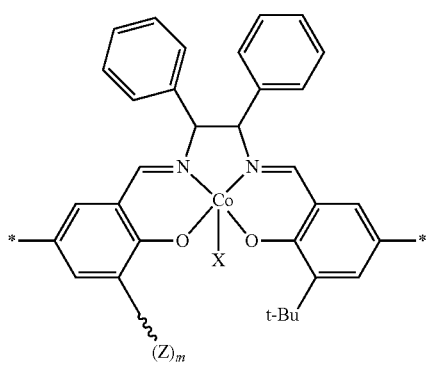
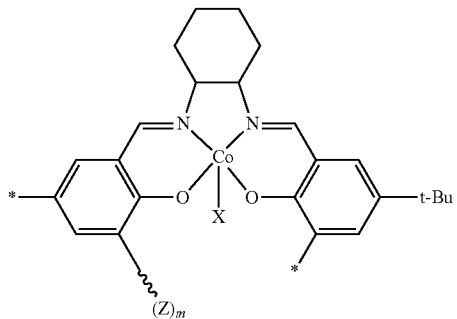
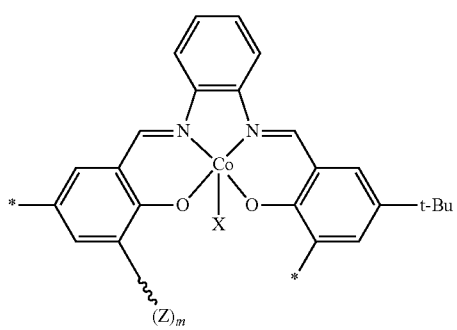
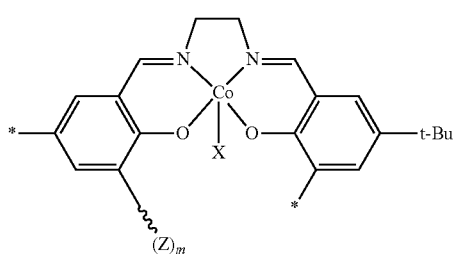
106
-continued
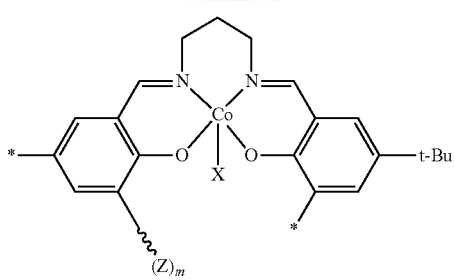
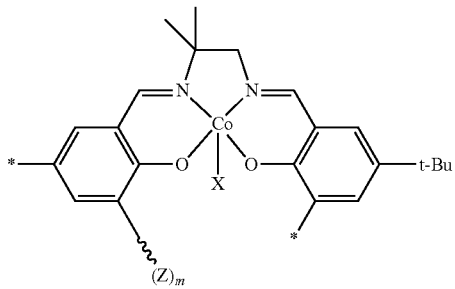
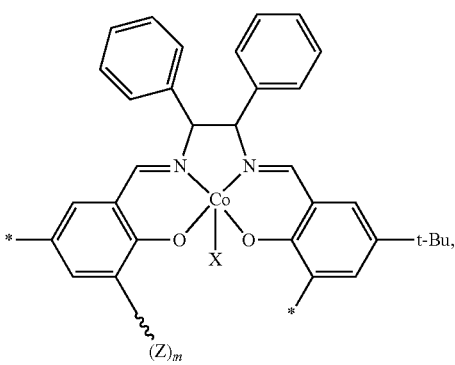
where * represents the site of attachment to a linker moiety joining the metal complexes in the oligomer, and each of X, and —⁓(Z)$_m$ is as defined above and in the classes and subclasses herein.
In certain embodiments, oligomeric catalysts of the present invention comprise metal complexes selected from the group consisting of:
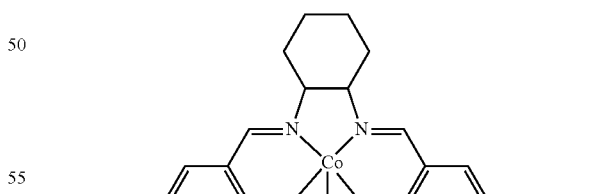
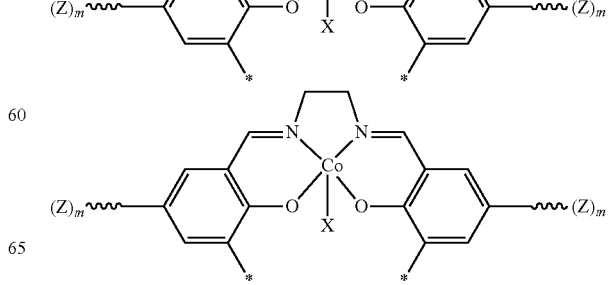

107
-continued
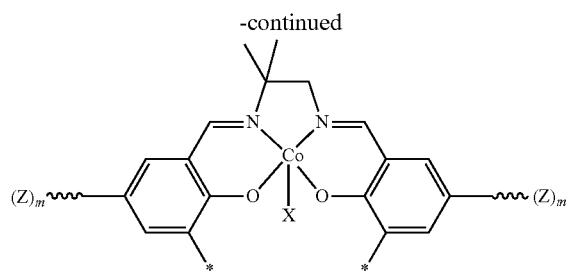
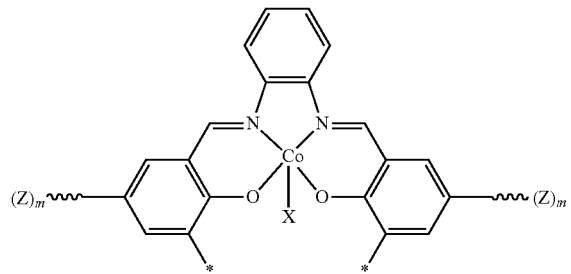
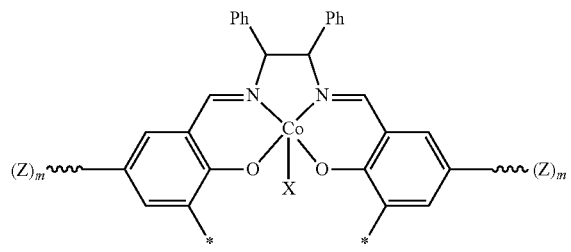
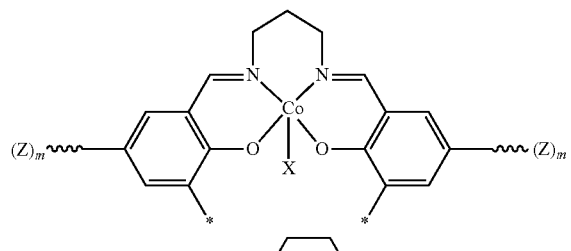
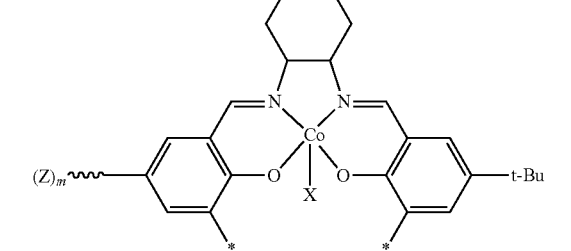
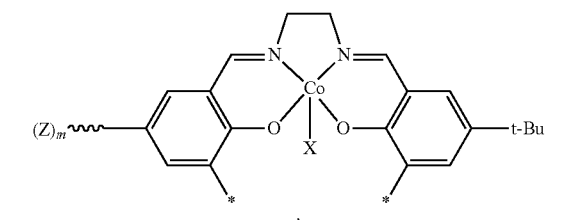
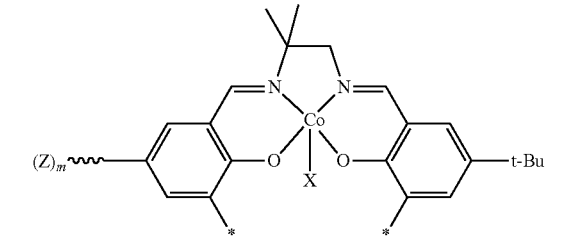
108
-continued
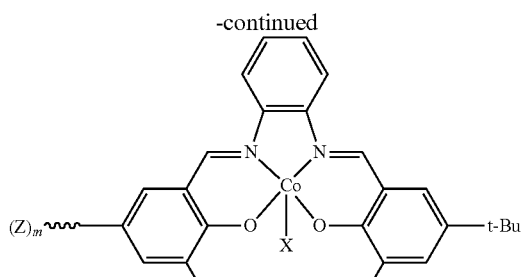
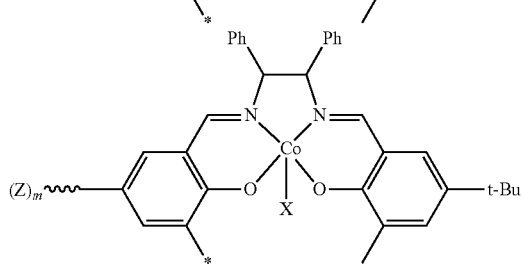
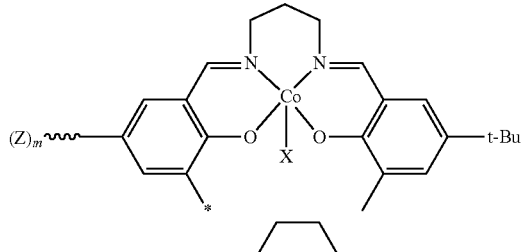
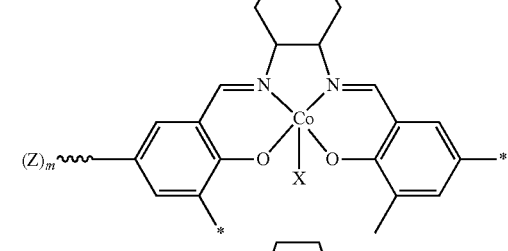
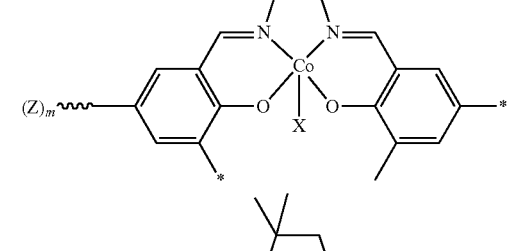
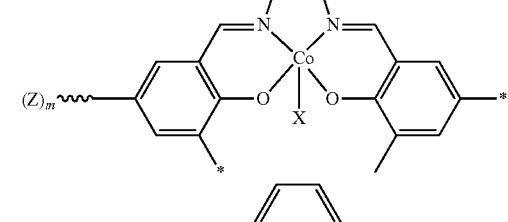
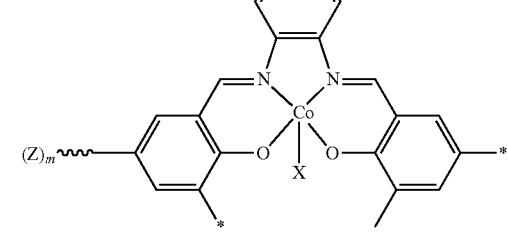

-continued

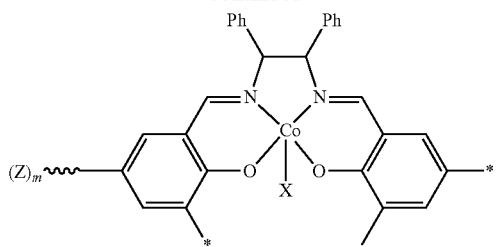

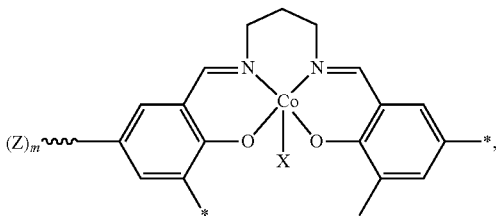

where each of *, X, and ‒∿∿(Z)$_m$ is as defined above and in the classes and subclasses herein.

In certain embodiments, oligomeric catalysts of the present invention comprise metal complexes selected from the group consisting of:

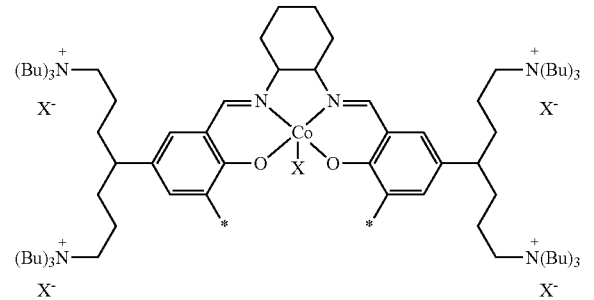

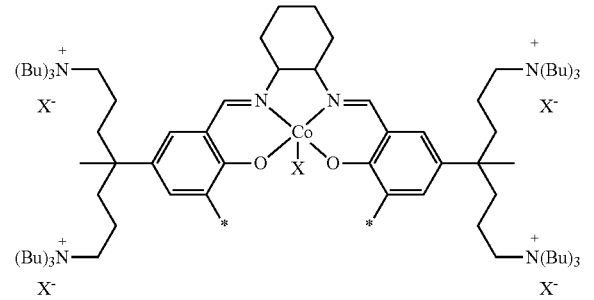

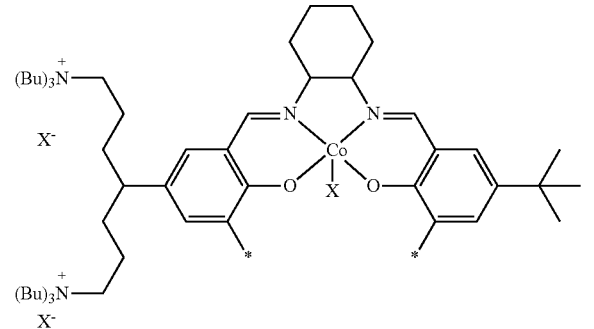

-continued

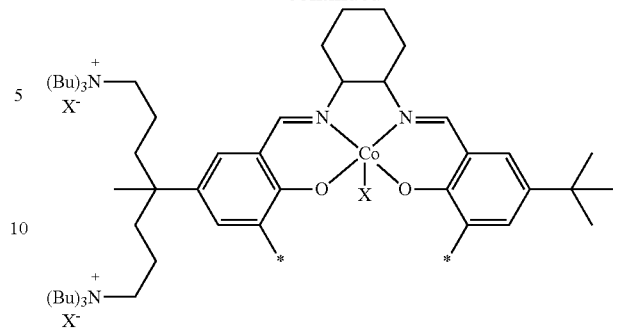

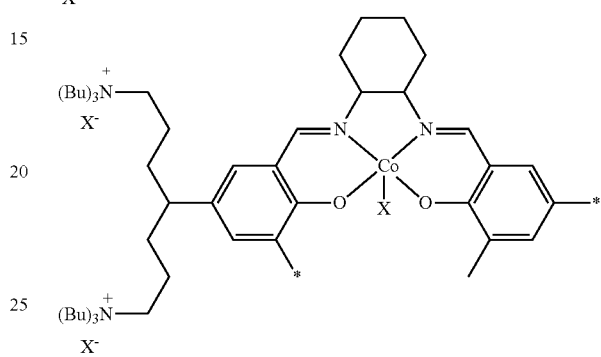

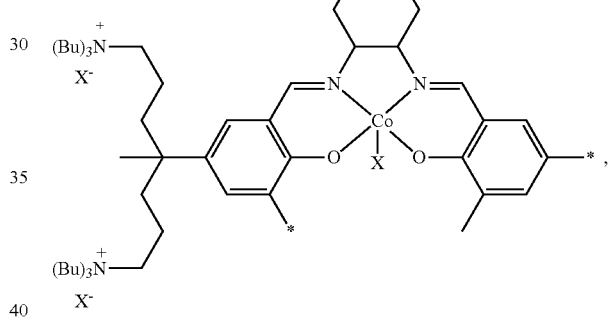

where each of * and X is as defined above and in the classes and subclasses herein.

In certain embodiments, oligomeric catalysts of the present invention comprise metal complexes selected from the group consisting of:

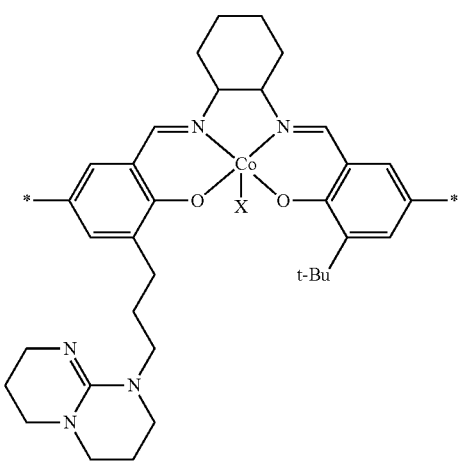

111
-continued
112
-continued
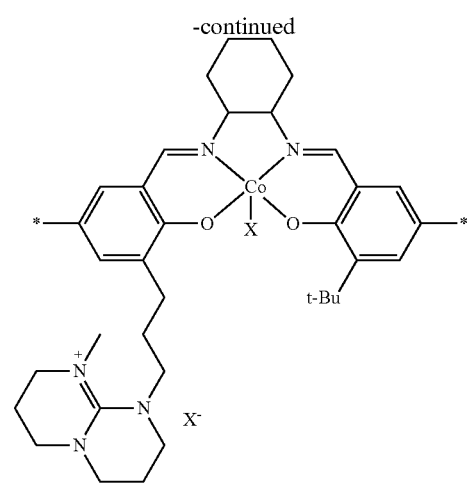
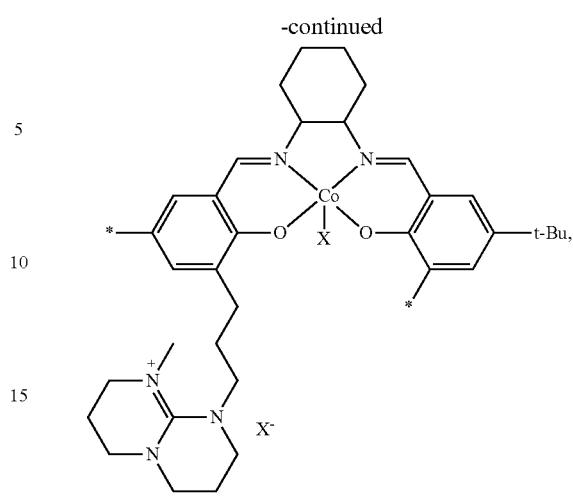
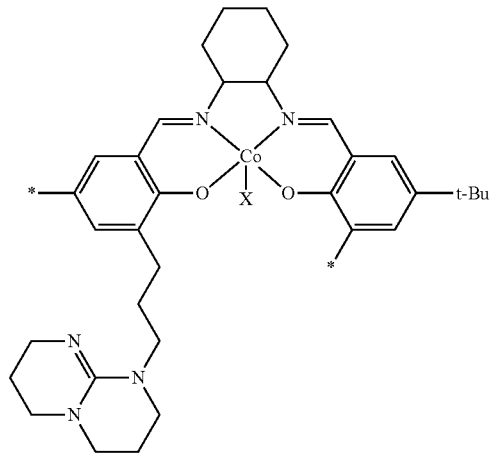
where each of * and X is as defined above and in the classes and subclasses herein.
In certain embodiments, oligomeric catalysts of the present invention conform to structures selected from the group consisting of:
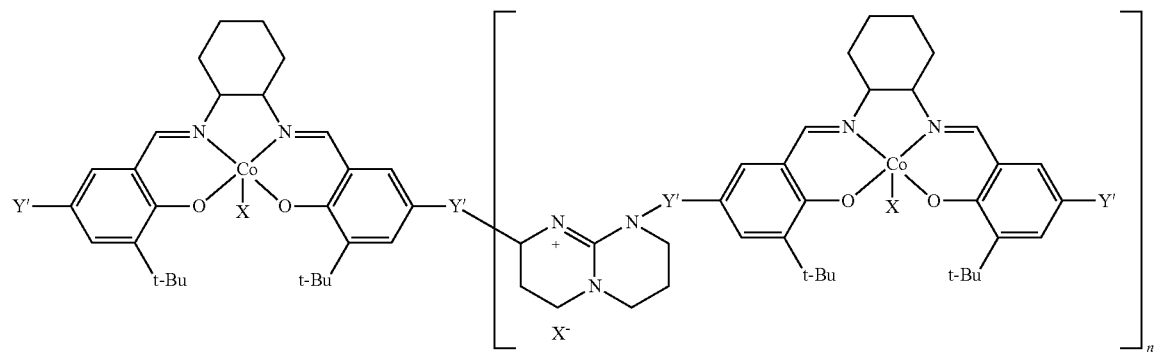
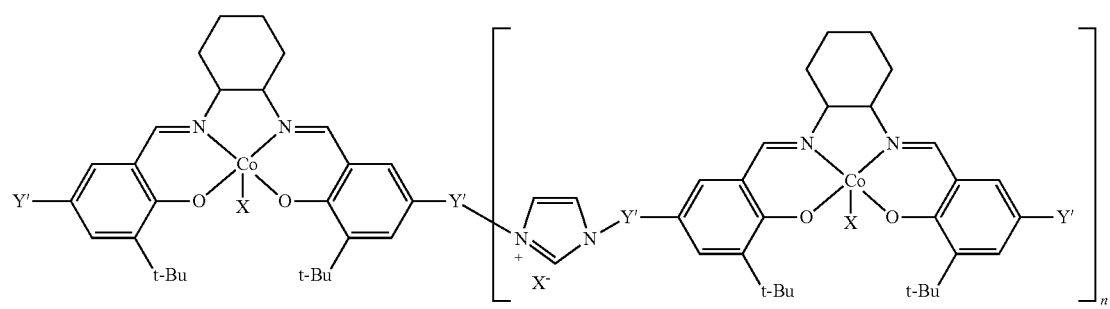

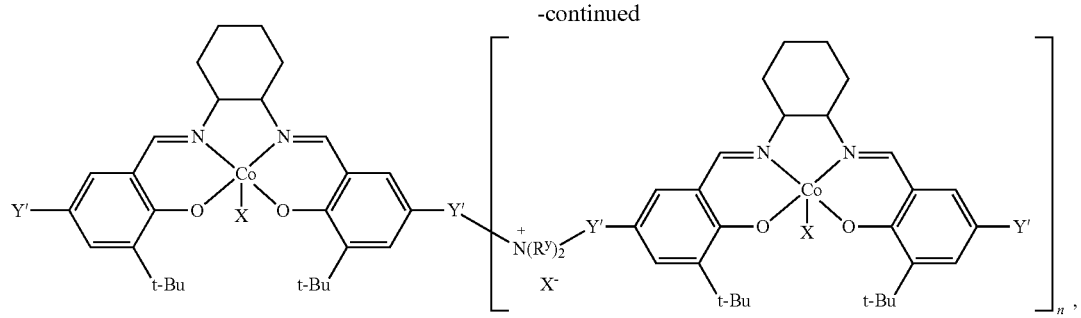

where each Y' is independently an optionally substituted $C_{1-20}$ aliphatic group wherein one or more carbons are optionally and independently replaced by -Cy-, —$NR^y$—, —$N(R^y)$C(O)—, —C(O)$N(R^y)$—, —$N(R^y)$C(O)O—, —OC(O)N$(R^y)$—, —$N(R^y)$C(O) N$(R^y)$—, —OC(O)O—, —O—, —C(O)—, —OC(O)—, —C(O)O—, —S—, —Si$(R^y)_2$—, —SO—, —$SO_2$—, —C(=S)—, —C(=$NR^y$)—, or —N=N—, and each of $R^y$, and X is as defined above and in the classes and subclasses herein.

In certain embodiments, oligomeric catalysts of the present invention conform to structures selected from the group consisting of:

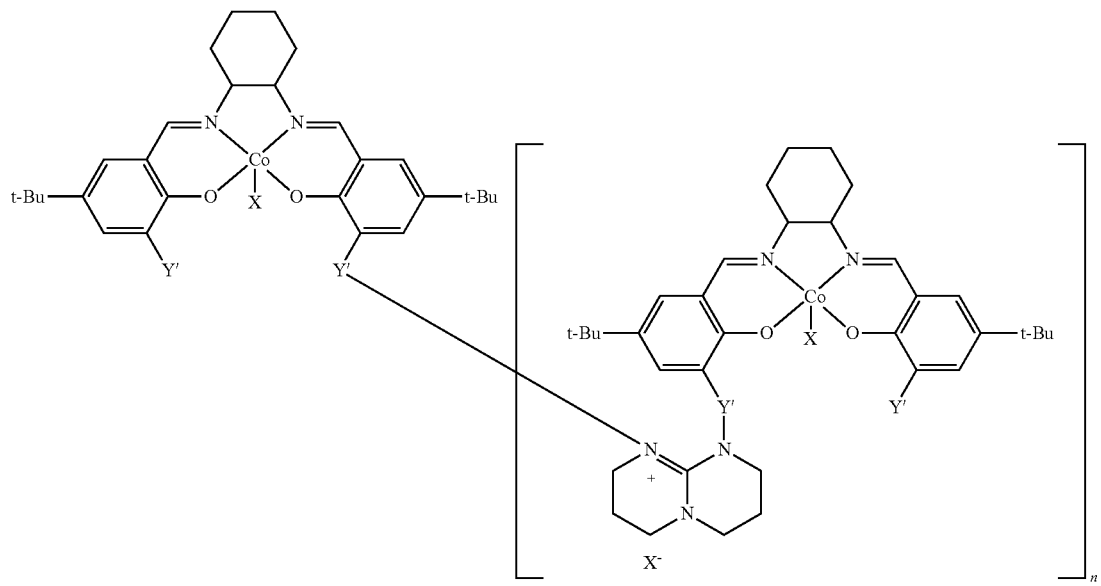

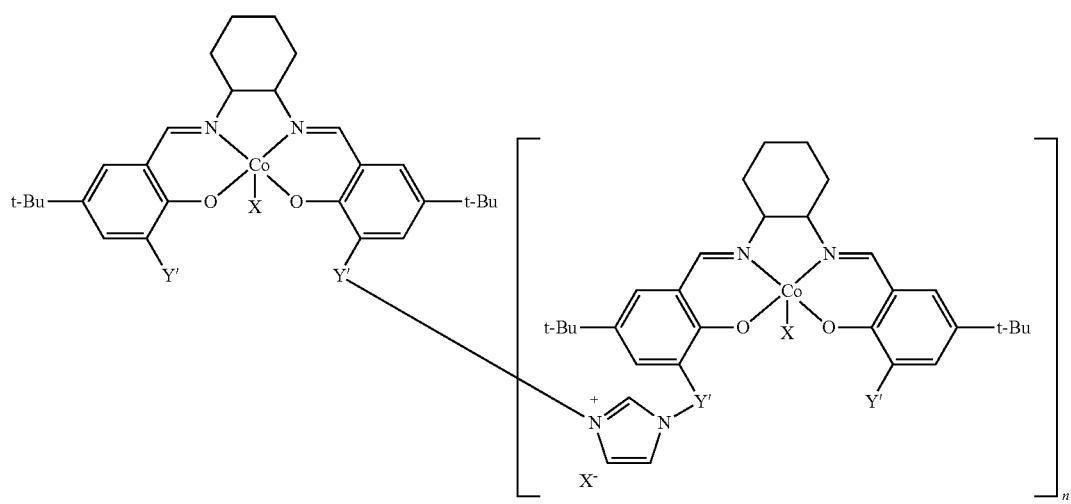

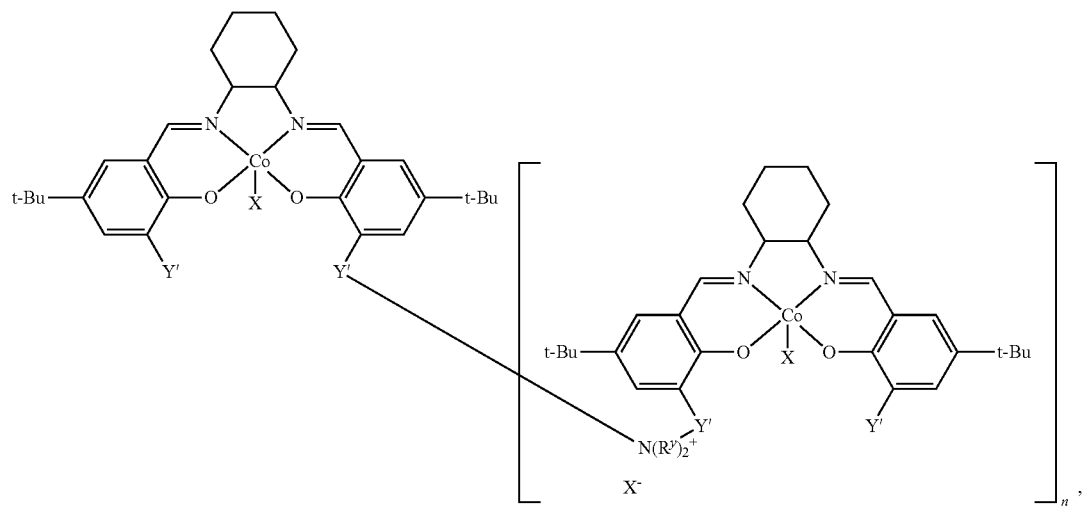
where each of Y', R<sup>y</sup>, and X is as defined above and in the classes and subclasses herein.
In certain embodiments, oligomeric catalysts of the present invention conform to structures selected from the group consisting of:
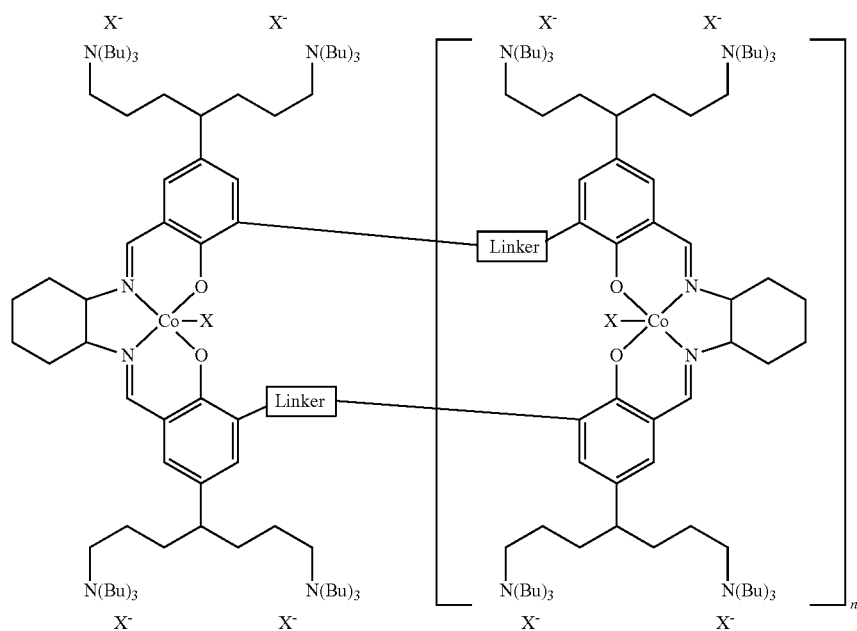

-continued
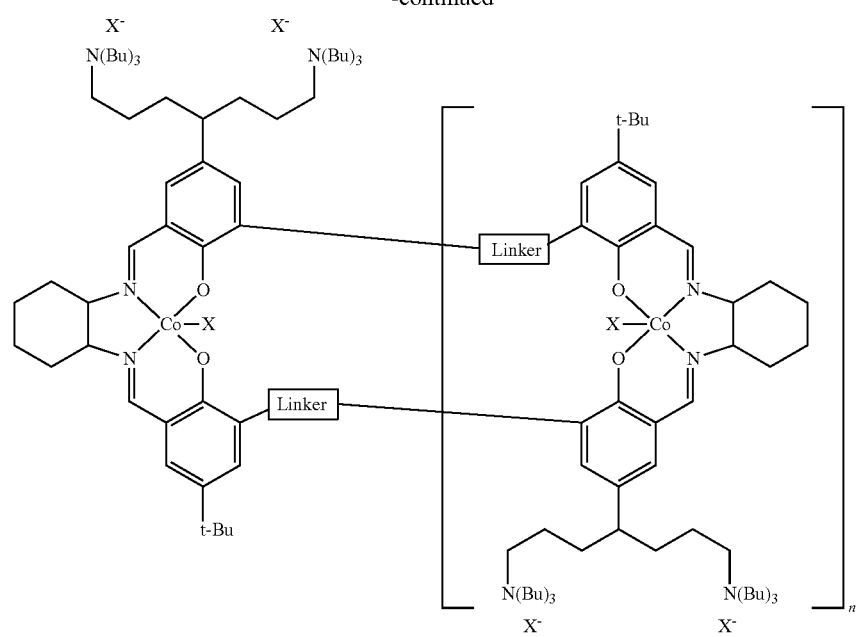
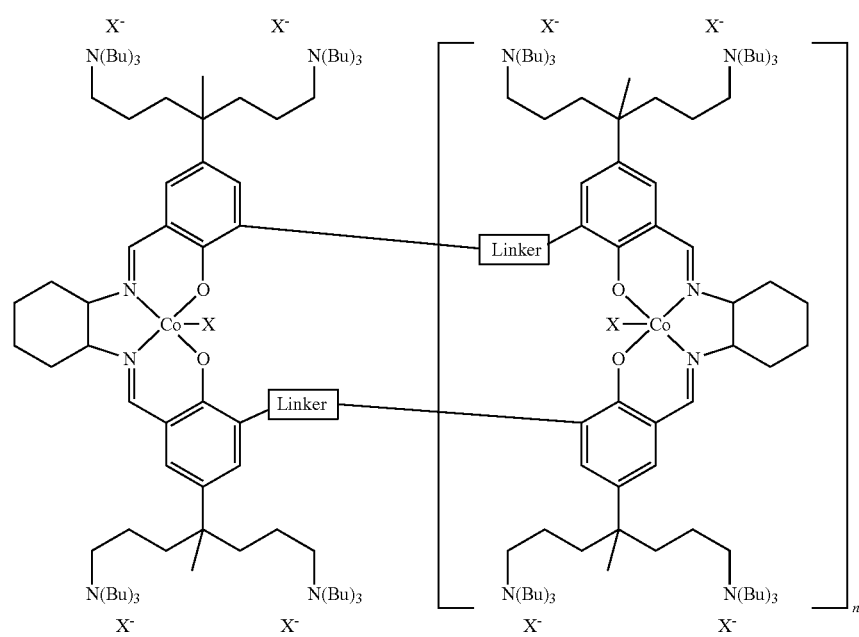

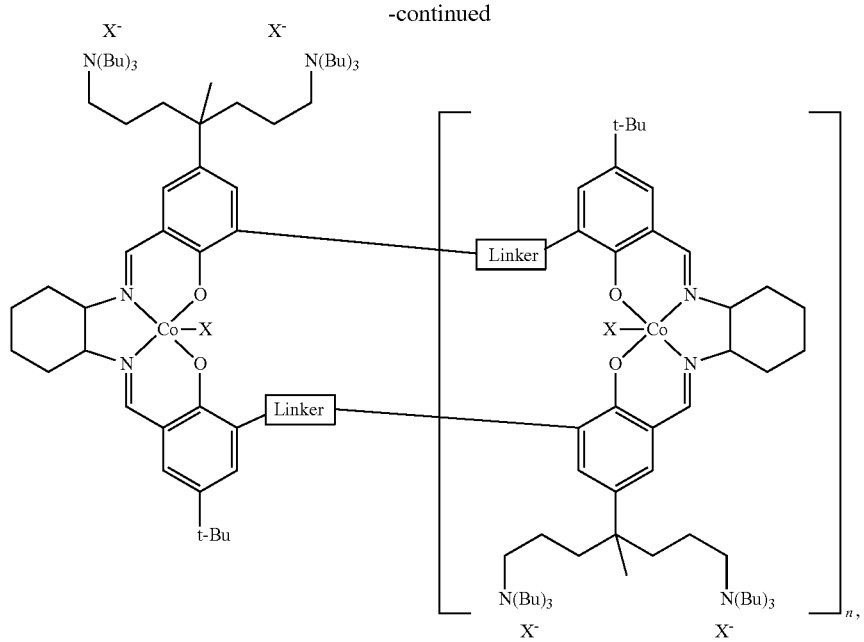

where X and the linker moieties are independently as defined above and in the classes and subclasses herein.

Syntheses of oligomeric catalysts are known in the art and include those described by Jacobsen and co-workers (*J. Am. Chem. Soc.* 2001, 123, 2687-2688), Fan et al., *J. Am. Chem. Soc.* 1999, 121, 7407-7408, and Yu et al., *J. Am. Chem. Soc.* 2000, 122, 6500-6501, the entire contents of each of which are hereby incorporated by reference. Additional synthetic procedures for the synthesis of mono-metal complexes with tethered activating moieties are found in WO 2010/022388, the entire contents of which are hereby incorporated by reference.

III.a. Metal Atoms

In certain embodiments, M is a metal atom selected from periodic table groups 3-13, inclusive. In certain embodiments, M is a transition metal selected from periodic table groups 5-12, inclusive. In certain embodiments, M is a transition metal selected from periodic table groups 4-11, inclusive. In certain embodiments, M is a transition metal selected from periodic table groups 5-10, inclusive. In certain embodiments, M is a transition metal selected from periodic table groups 7-9, inclusive. In some embodiments, M is selected from the group consisting of Cr, Mn, V, Fe, Co, Mo, W, Ru, Al, and Ni. In some embodiments, M is selected from the group consisting of Co, Al, and Cr. In some embodiments, M is a metal atom selected from the group consisting of: cobalt; chromium; aluminum; titanium; ruthenium, and manganese. In some embodiments, M is cobalt. In some embodiments, M is chromium. In some embodiments, M is aluminum. In some embodiments, M is zinc.

In certain embodiments, a metal complex is cobalt complex. In certain embodiments where the metal complex is a cobalt complex, each cobalt atom has an oxidation state of 3+ (i.e., Co(III)). In some embodiments, at least one cobalt metal has an oxidation state of 2+ (i.e., Co(II)).

In certain embodiments, for metal complexes described herein, $M\text{-}(X)_k$ is Co—OC(O)CF$_3$. In certain embodiments, $M\text{-}(X)_k$ is Co—OAc. In certain embodiments, $M\text{-}(X)_k$ is Co—OC(O)C$_6$F$_5$. In certain embodiments, $M\text{-}(X)_k$ is Co—N$_3$. In certain embodiments, $M\text{-}(X)_k$ is Co—Cl. In certain embodiments, $M\text{-}(X)_k$ is Co-nitrophenoxy. In certain embodiments, $M\text{-}(X)_k$ is Co-dinitrophenoxy. In some embodiments, $M\text{-}(X)_k$ is Cr—X.

IV. Polymers

In some embodiments, the present disclosure provides methods of polymerization comprising contacting an epoxide with carbon dioxide in the presence of a provided metal complex to form a polycarbonate. In some embodiments, the present invention provides a method of polymerization, the method comprising:

a) providing an epoxide of formula:

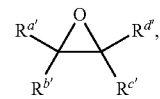

wherein:
$R^{a'}$ is hydrogen or an optionally substituted radical selected from the group consisting of C$_{1-30}$ aliphatic; C$_{1-30}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; and each of $R^{b'}$, $R^{c'}$ and $R^{d'}$ is independently hydrogen or an optionally substituted radical selected from the group consisting of C$_{1-12}$ aliphatic; C$_{1-12}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

wherein any of ($R^{a'}$ and $R^{c'}$), ($R^{c'}$ and $R^{d'}$), and ($R^{a'}$ and $R^{b'}$) can be taken together with intervening atoms to form one or more optionally substituted rings;

b) contacting the epoxide and carbon dioxide in the presence of a metal complex as described herein to provide a polymer having a formula selected from the group consisting of:

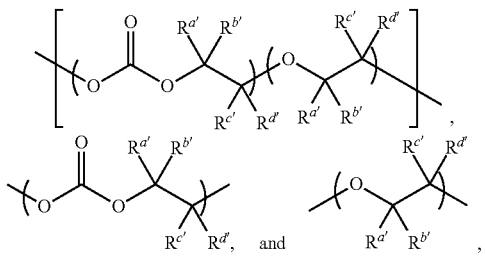

In some embodiments, a provided polymer has a formula:

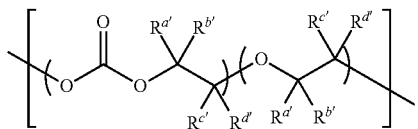

In some embodiments, a provided polymer has a formula:

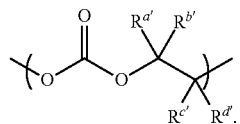

In some embodiments, carbon dioxide is optional and a provided polymer has a formula:

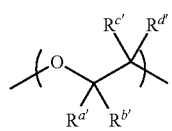

In certain embodiments, $R^{b'}$, $R^{c'}$ and $R^{d'}$ are each hydrogen. In some embodiments, $R^{a'}$ is optionally substituted $C_{1-12}$ aliphatic. In some embodiments, $R^{a'}$ is optionally substituted $C_{1-12}$ heteroaliphatic. In some embodiments, the epoxide is ethylene oxide, propylene oxide, or cyclohexene oxide.

In certain embodiments, one of $R^{a'}$, $R^{b'}$, $R^{c'}$, and $R^{d'}$ is hydrogen. In certain embodiments, two of $R^{a'}$, $R^{b'}$, $R^{c'}$, and $R^{d'}$ are hydrogen. In certain embodiments, three of $R^{a'}$, $R^{b'}$, $R^{c'}$, and $R^{d'}$ are hydrogen. In certain embodiments, three of $R^{a'}$, $R^{b'}$, $R^{c'}$, and $R^{d'}$ are hydrogen, and the remaining R group is $C_{1-12}$ aliphatic. In certain embodiments, three of $R^{a'}$, $R^{b'}$, $R^{c'}$, and $R^{d'}$ are hydrogen, and the remaining R group is $C_{1-6}$ aliphatic. In certain embodiments, three of $R^{a'}$, $R^{b'}$, $R^{c'}$ and $R^{d'}$ are hydrogen, and the remaining R group is methyl. In certain embodiments, three of $R^{a'}$, $R^{b'}$, $R^{c'}$, and $R^{d'}$ are hydrogen, and the remaining R group is ethyl. In certain embodiments, three of $R^{a'}$, $R^{b'}$, $R^{c'}$, and $R^{d'}$ are hydrogen, and the remaining R group is n-butyl. In certain embodiments, three of $R^{a'}$, $R^{b'}$, $R^{c'}$, and $R^{d'}$ are hydrogen, and the remaining R group is chloromethyl.

In certain embodiments, $R^{a'}$ is hydrogen. In certain embodiments, $R^{b'}$ is hydrogen. In certain embodiments, $R^{c'}$ is hydrogen. In certain embodiments, $R^{d'}$ is hydrogen.

In certain embodiments, $R^{a'}$, $R^{b'}$, $R^{c'}$ and $R^{d'}$ are each independently an optionally substituted $C_{1-30}$ aliphatic group. In certain embodiments, $R^{a'}$, $R^{b'}$, $R^{c'}$ and $R^{d'}$ are each independently an optionally substituted $C_{1-20}$ aliphatic group. In certain embodiments, $R^{a'}$, $R^{b'}$, $R^{c'}$ and $R^{d'}$ are each independently an optionally substituted $C_{1-12}$ aliphatic group. In certain embodiments, $R^{a'}$, $R^{b'}$, $R^{c'}$ and $R^{d'}$ are each independently an optionally substituted $C_{1-8}$ aliphatic group. In certain embodiments, $R^{a'}$, $R^{b'}$, $R^{c'}$ and $R^{d'}$ are each independently an optionally substituted $C_{3-8}$ aliphatic group. In certain embodiments, $R^{a'}$, $R^{b'}$, $R^{c'}$ and $R^{d'}$ are each independently an optionally substituted $C_{3-12}$ aliphatic group.

In certain embodiments, $R^{a'}$ is an optionally substituted $C_{1-30}$ aliphatic group. In certain embodiments, $R^{b'}$ is an optionally substituted $C_{1-30}$ aliphatic group. In certain embodiments, $R^{c'}$ is an optionally substituted $C_{1-30}$ aliphatic group. In certain embodiments, $R^{d'}$ is an optionally substituted $C_{1-30}$ aliphatic group.

In some embodiments, an $R^{a'}$ and an $R^{b'}$ attached to the same carbon are taken together to form one or more optionally substituted 3-12-membered carbocyclic rings. In some embodiments, an $R^{a'}$ and an $R^{b'}$ attached to the same carbon are taken together to form a polycyclic carbocycle comprising two or more optionally substituted 3-8-membered carbocyclic rings. In some embodiments, an $R^{a'}$ and an $R^{b'}$ attached to the same carbon are taken together to form a polycyclic carbocycle comprising two or more optionally substituted 5-7-membered carbocyclic rings.

In some embodiments, an $R^{a'}$ and an $R^{b'}$ attached to the same carbon are taken together to form a bicyclic carbocycle comprising two optionally substituted 3-12-membered carbocyclic rings. In some embodiments, an $R^{a'}$ and an $R^{b'}$ attached to the same carbon are taken together to form a bicyclic carbocycle comprising two optionally substituted 3-8-membered carbocyclic rings. In some embodiments, an $R^{a'}$ and an $R^{b'}$ attached to the same carbon are taken together to form a bicyclic carbocycle comprising two optionally substituted 5-7-membered carbocyclic rings.

In certain embodiments, an $R^{a'}$ and an $R^{b'}$ attached to the same carbon are taken together to form an optionally substituted 3-12-membered carbocyclic ring. In certain embodiments, an $R^{a'}$ and an $R^{b'}$ attached to the same carbon are taken together to form an optionally substituted 3-8-membered carbocyclic ring. In certain embodiments, an $R^{a'}$ and an $R^{b'}$ attached to the same carbon are taken together to form an optionally substituted 5-7-membered carbocyclic ring.

In some embodiments, an $R^{b'}$ and an $R^{c'}$ attached to adjacent carbons are taken together to form one or more optionally substituted 3-12-membered carbocyclic rings. In some embodiments, an $R^{b'}$ and an $R^{c'}$ attached to adjacent carbons are taken together to form a polycyclic carbocycle comprising two or more optionally substituted 3-8-membered carbocyclic rings. In some embodiments, an $R^{b'}$ and an $R^{c'}$ attached to adjacent carbons are taken together to form a polycyclic carbocycle comprising two or more optionally substituted 5-7-membered carbocyclic rings.

In some embodiments, an $R^{b'}$ and an $R^{c'}$ attached to adjacent carbons are taken together to form a bicyclic carbocycle comprising two optionally substituted 3-12-membered carbocyclic rings. In some embodiments, an $R^{b'}$ and an $R^{c'}$ attached to adjacent carbons are taken together to form a bicyclic carbocycle comprising two optionally substituted 3-8-membered carbocyclic rings. In some embodiments, an $R^{b'}$ and an $R^{c'}$ attached to adjacent carbons are taken together to form a bicyclic carbocycle comprising two optionally substituted 5-7-membered carbocyclic rings.

In certain embodiments, an $R^{b'}$ and an $R^{c'}$ attached to adjacent carbons are taken together to form an optionally substituted 3-12-membered carbocyclic ring. In certain embodiments, an $R^{b'}$ and an $R^{c'}$ attached to adjacent carbons are taken together to form an optionally substituted 3-8-membered carbocyclic ring. In certain embodiments, an $R^{b'}$ and an $R^{c'}$ attached to adjacent carbons are taken together to form an optionally substituted 5-7-membered carbocyclic ring.

In certain embodiments, the polymer comprises a copolymer of two different repeating units where $R^{a'}$, $R^{b'}$, and $R^{c'}$ of the two different repeating units are not all the same. In some embodiments, a polymer comprises a copolymer of three or more different repeating units wherein $R^{a'}$, $R^{b'}$, and $R^{c'}$ of each of the different repeating units are not all the same as $R^{a'}$, $R^{b'}$, and $R^{c'}$ of any of the other different repeating units. In some embodiments, a polymer is a random copolymer. In some embodiments, a polymer is a tapered copolymer.

In some embodiments, a polymer contains a metal complex as described herein. In some embodiments, a polymer comprises residue of a metal complex as described herein. In some embodiments, a polymer comprises a salt of an organic cation and X, wherein X is a nucleophile or counterion. In some embodiments, X is 2,4-dinitrophenolate anion.

In some embodiments, $R^{a'}$ is optionally substituted $C_{1-12}$ aliphatic. In some embodiments, $R^{a'}$ is optionally substituted $C_{1-12}$ heteroaliphatic. In some embodiments, $R^{a'}$ is optionally substituted phenyl. In some embodiments, $R^{a'}$ is optionally substituted 8- to 10-membered aryl. In some embodiments, $R^{a'}$ is optionally substituted 5- to 10-membered heteroaryl. In some embodiments, $R^{a'}$ is optionally substituted 3- to 7-membered heterocyclic.

In certain embodiments, $R^{a'}$ is selected from methyl, ethyl, propyl, butyl, vinyl, allyl, phenyl, trifluoromethyl,

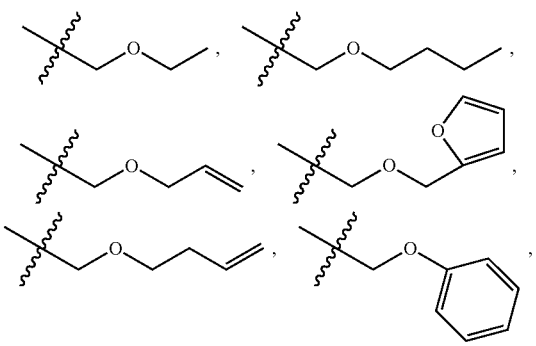

-continued

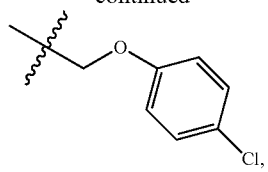

or any two or more of the above. In certain embodiments, $R^{a'}$ is methyl. In certain embodiments, $R^{a'}$ is ethyl. In certain embodiments, $R^{a'}$ is propyl. In certain embodiments, $R^{a'}$ is butyl. In certain embodiments, $R^{a'}$ is vinyl. In certain embodiments, $R^{a'}$ is allyl. In certain embodiments, $R^{a'}$ is phenyl. In certain embodiments, $R^{a'}$ is trifluoromethyl. In certain embodiments, $R^{a'}$ is

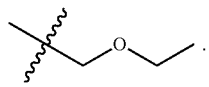 [SMILES: *COCC ; "."]

In certain embodiments, $R^{a'}$ is

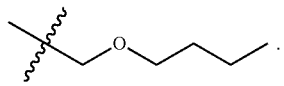 [SMILES: *COCCCC ; "."]

In certain embodiments, $R^{a'}$ is

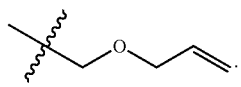 [SMILES: *COCC=C]

In certain embodiments, $R^{a'}$ is

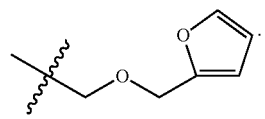

In certain embodiments, $R^{a'}$ is

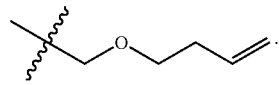 [SMILES: *COCCC=C]

In certain embodiments, $R^{a'}$ is

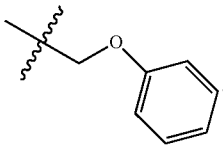

In certain embodiments, $R^{a'}$ is

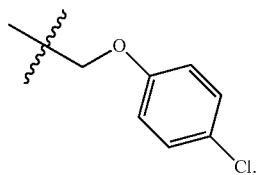 [SMILES: *COc1ccc(Cl)cc1]

In some embodiments, $R^{b'}$ is hydrogen. In some embodiments, $R^{b'}$ is optionally substituted $C_{1-12}$ aliphatic. In some embodiments, $R^{b'}$ is optionally substituted $C_{1-12}$ heteroaliphatic. In some embodiments, $R^{b'}$ is optionally substituted phenyl. In some embodiments, $R^{b'}$ is optionally substituted 8- to 10-membered aryl. In some embodiments, $R^{b'}$ is optionally substituted 5- to 10-membered heteroaryl. In some embodiments, $R^{b'}$ is optionally substituted 3- to 7-membered heterocyclic.

In some embodiments, $R^{c'}$ is hydrogen. In some embodiments, $R^{c'}$ is optionally substituted $C_{1-12}$ aliphatic. In some embodiments, $R^{c'}$ is optionally substituted $C_{1-12}$ heteroaliphatic. In some embodiments, $R^{c'}$ is optionally substituted phenyl. In some embodiments, $R^{c'}$ is optionally substituted 8- to 10-membered aryl. In some embodiments, $R^{c'}$ is optionally substituted 5- to 10-membered heteroaryl. In some embodiments, $R^{c'}$ is optionally substituted 3- to 7-membered heterocyclic.

In some embodiments, $R^{a'}$ and $R^{c'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, $R^{b'}$ and $R^{c'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, $R^{a'}$ and $R^{b'}$ are taken together with intervening atoms to form one or more rings selected from the group consisting of: optionally substituted $C_3$-$C_{14}$ carbocycle, optionally substituted 3- to 14-membered heterocycle, optionally substituted phenyl, optionally substituted $C_8$-$C_{10}$ aryl, and optionally substituted 5- to 10-membered heteroaryl.

In some embodiments, the invention includes methods for synthesizing aliphatic polycarbonates from epoxides and $CO_2$. In certain embodiments, such methods comprise the step of contacting one or more epoxides with $CO_2$ in the presence of one or more of the oligomeric metal complexes described hereinabove. Suitable methods and conditions for performing these polymerizations are disclosed in U.S. Pat. No. 7,304,172, and in Angew. Chem. Int. Ed. 2003, 42, 5484-5487, the entire contents of each of which are hereby incorporated herein by reference.

In some embodiments, the invention includes methods for synthesizing polyethers from epoxides. In certain embodiments, such methods comprise the step of contacting one or more epoxides with one or more of the oligomeric metal complexes described hereinabove. Suitable methods of performing these reactions are disclosed in U.S. Pat. No. 7,399,822, the entire contents of which are hereby incorporated herein by reference.

In some embodiments, the invention includes methods for synthesizing cyclic carbonates from carbon dioxide and epoxides using catalysts described above, suitable methods of performing this reaction are disclosed in U.S. Pat. No. 6,870,004 which is incorporated herein by reference.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been presented by way of example.

What is claimed is:
1. An oligomeric complex having the structure:

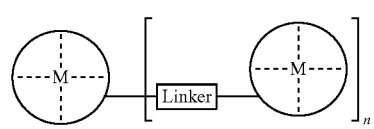

D-I wherein:
each M is independently a metal atom;
each

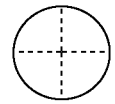

is independently a multidentate ligand;
each linker is independently an optionally substituted $C_{2-30}$ aliphatic group wherein one or more carbons are optionally and independently replaced by -Cy-, —$NR^y$—, —$N(R^y)C(O)$—, —$C(O)N(R^y)$—, —$N(R^y)C(O)O$—, —$OC(O)N(R^y)$—, —$N(R^y)C(O)$ $N(R^y)$—, —$OC(O)$ $O$—, —$O$—, —$C(O)$—, —$OC(O)$—, —$C(O)O$—, —$S$—, —$Si(R^y)_2$—, —$SO$—, —$SO_2$—, —$C(=S)$—, —$C(=NR^y)$—, or —$N=N$—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-12 membered bivalent saturated, partially unsaturated, or aryl bicyclic ring having 0-5 heteroatoms independently selected from nitrogen, oxygen, or sulfur; and
each $R^y$ is independently —H, or an optionally substituted radical selected from the group consisting of $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, a 5-6 membered heteroaryl ring having 1-3 heteroatoms independently selected from nitrogen, oxygen, or sulfur, and 8- to 10- membered aryl; and
n is from 1 to 50;
wherein the oligomeric complex is substituted with one or more activating groups

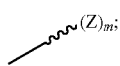

where —⌇⌇ is a linking moiety covalently coupled to the ligand system, m is an integer from 1 to 4 representing the number of Z groups present on an individual linker moiety; and each Z is independently an activating functional group;

and wherein the repeating units of n are optionally joined to form a cyclic oligomeric complex.

2. The oligomeric complex of claim 1, having the formula:

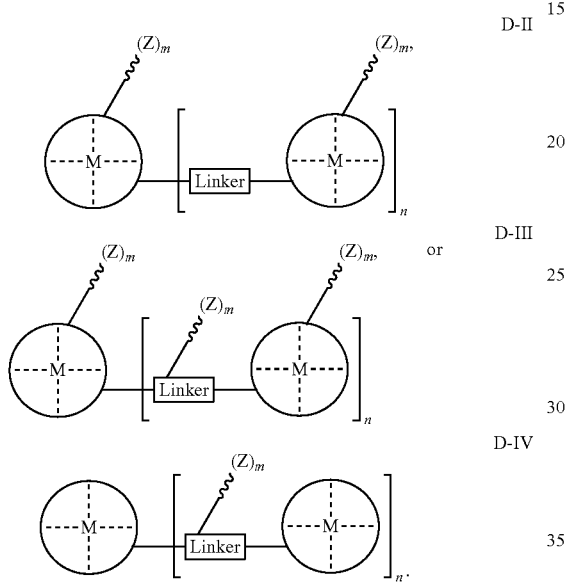

3. The oligomeric complex of claim 2, wherein each

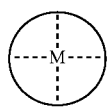

comprises:

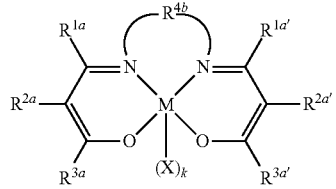

wherein:

$R^{1a}$ and $R^{1a'}$ are independently a —⌇⌇$(Z)_m$ group, a linker, hydrogen, or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated, or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur;

$R^{2a}$, $R^{2a'}$, $R^{3a}$, and $R^{3a'}$ are independently a —⌇⌇$(Z)_m$ group, a linker, hydrogen, —OR, —NR$_2$, —SR, —CN, —NO$_2$, —OC(O)R, —CO$_2$R, —NRC(O)R, —C(O)NR$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated, or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where any of [$R^{2a'}$ and $R^{3a'}$], [$R^{2a}$ and $R^{3a}$], [$R^{1a}$ and $R^{2a}$], and [$R^{1a'}$ and $R^{2a'}$] may optionally be taken together with intervening atoms to form one or more rings which may in turn be substituted with one or more $R^d$ groups;

$R^{4b}$ is selected from the group consisting of:

a)
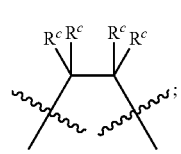

b)
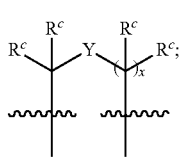

c)
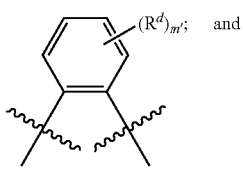
and d)
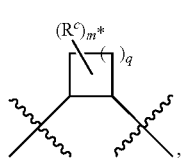

where

R$^c$ at each occurrence is independently a —⌇⌇(Z)$_m$ group, a linker, hydrogen, halogen, —OR, —NR$_2$, —SR, —CN, —NO$_2$, —OC(O)R, —CO$_2$R, —NRC(O)R, —C(O)NR$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more R$^c$ groups may be taken together with the carbon atoms to which they are attached and any intervening atoms to form one or more optionally substituted rings; when two R$^c$ groups are attached to the same carbon atom, they may optionally be taken together along with the carbon atom to which they are attached to form an optionally substituted moiety selected from the group consisting of: an alkene, a 3- to 8-membered spirocyclic ring, a carbonyl, an oxime, a hydrazone, and an imine;

R$^d$ at each occurrence is independently a —⌇⌇(Z)$_m$ group, a linker, a portion of a linker that is connected to another oligomeric unit, a moiety capable of forming a linker, hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7-14 carbon saturated, partially unsaturated, or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more R$^d$ groups may be taken together with intervening atoms to form one or more optionally substituted rings optionally containing one or more heteroatoms, R at each occurrence is independently hydrogen, an optionally substituted radical selected the group consisting of acyl; C$_{1-6}$ aliphatic; C$_{1-6}$ heteroaliphatic; carbamoyl; arylalkyl; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring, each X is independently an anion;

Y is a divalent linker selected from the group consisting of: —NR—, —N(R)C(O)—, —C(O)NR—, —O—, —C(O)—, —OC(O)—, —C(O)O—, —OC(O)O—, —S—, —SO—, —SO$_2$—, —SiR$_2$—, —C(=S)—, —C(=NR)—, or —(R$^c$)C=C(R$^c$)—; —N=N—; a polyether; a C$_3$ to C$_8$ substituted or unsubstituted carbocycle; and a C$_1$ to C$_8$ substituted or unsubstituted heterocycle;

k is 0, 1, or 2;

m* is 0 or an integer from 1 to 6, inclusive;

m' is 0 or an integer from 1 to 4, inclusive;

q is 0 or an integer from 1 to 4, inclusive; and x is 0, 1, or 2.

4. The oligomeric complex of claim 3, wherein

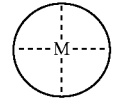

comprises:

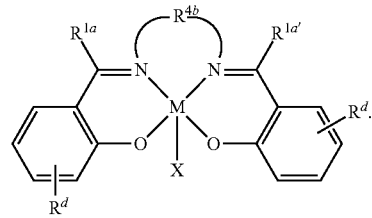

5. The oligomeric complex of claim 4, wherein

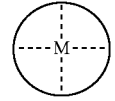

comprises:

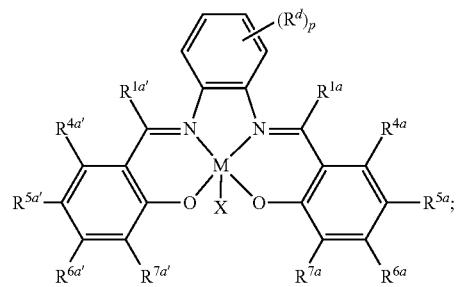

-continued

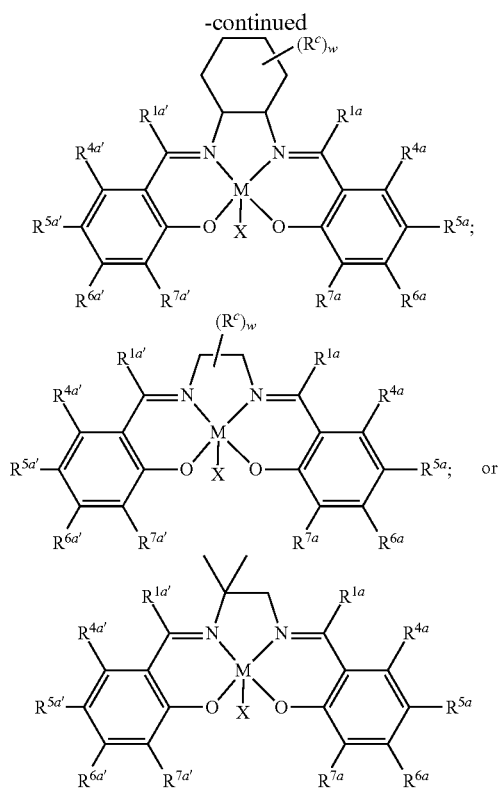

wherein:

$R^{4a}$, $R^{4a'}$, $R^{5a}$, $R^{5a'}$, $R^{6a}$, $R^{6a'}$, $R^{7a}$, and $R^{7a'}$ are each independently a —⁓$(Z)_m$ group, a linker, hydrogen, halogen, —OR, —NR$_2$, —SR, —CN, —NO$_2$, —OC(O)R, —CO$_2$R, —NRC(O)R, —C(O)NR$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7-14 carbon saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur, where [$R^1$ and $R^{4a}$], [$R^{1'}$ and $R^{4a'}$] and any two or more adjacent $R^{4a}$, $R^{4a'}$, $R^{5a}$, $R^{5a'}$, $R^{6a}$, $R^{6a'}$, $R^{7a}$, and $R^{7a'}$ groups can optionally be taken together with intervening atoms to form one or more optionally substituted rings;

w is 0 or an integer from 1 to 6, inclusive; and p is 0 or an integer from 1 to 4, inclusive.

6. The oligomeric complex of claim 3 having a structure selected from the group consisting of:

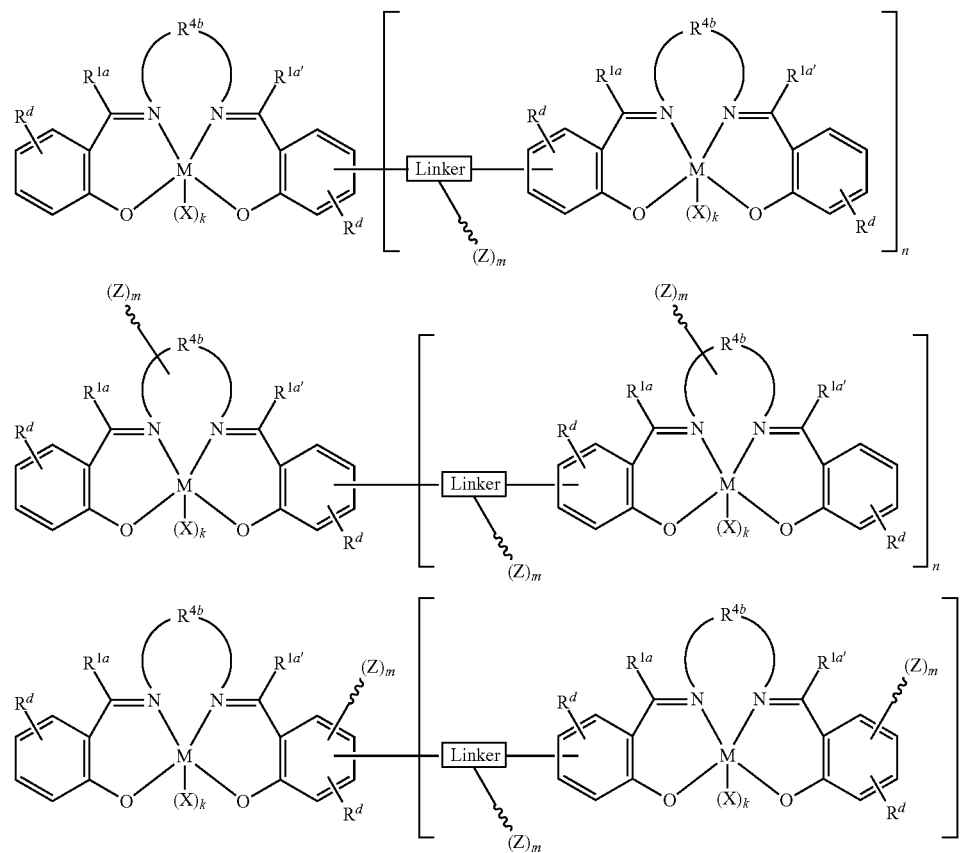

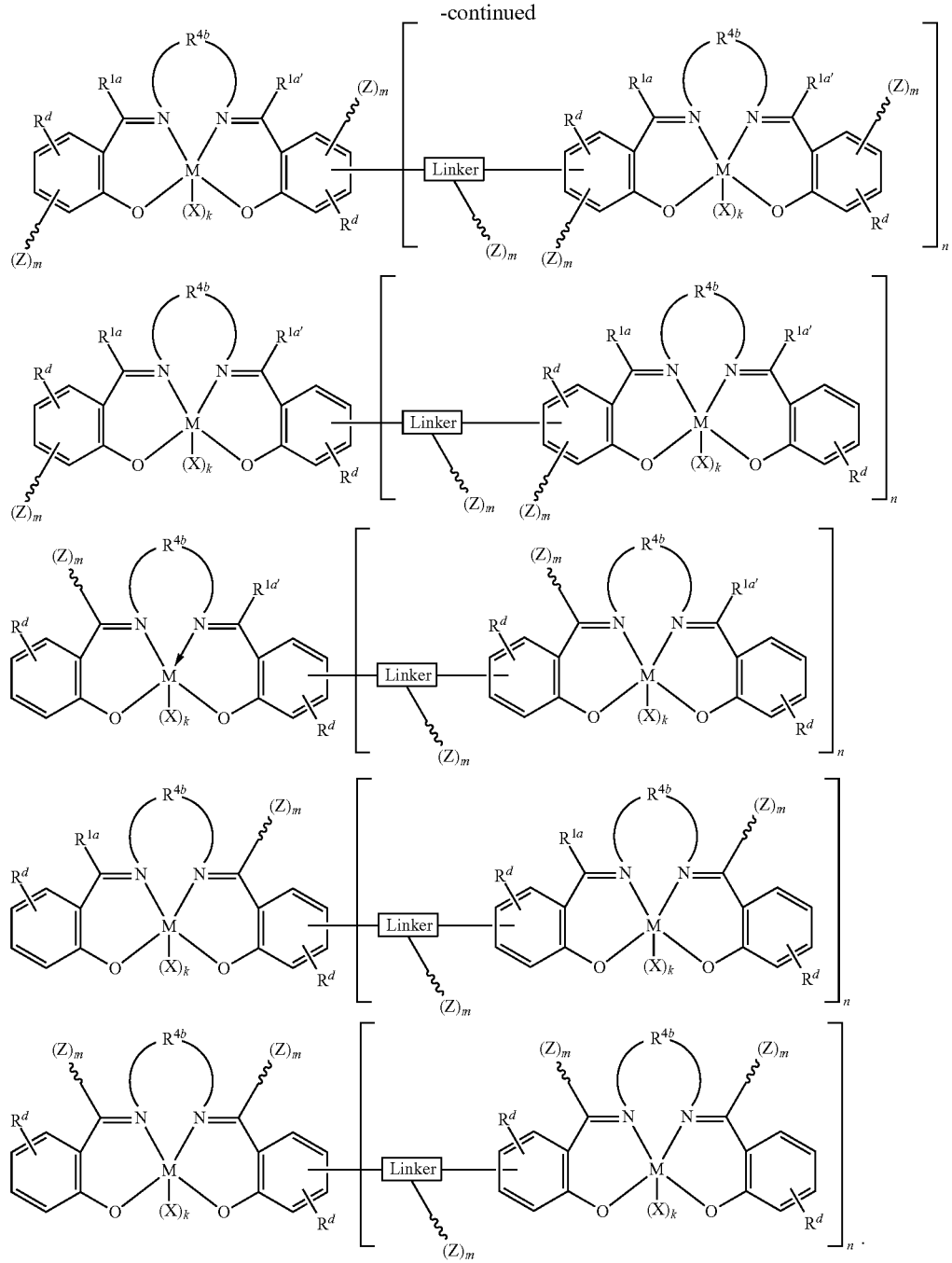
7. The oligomeric complex of claim 6 having a structure selected from the group consisting of:
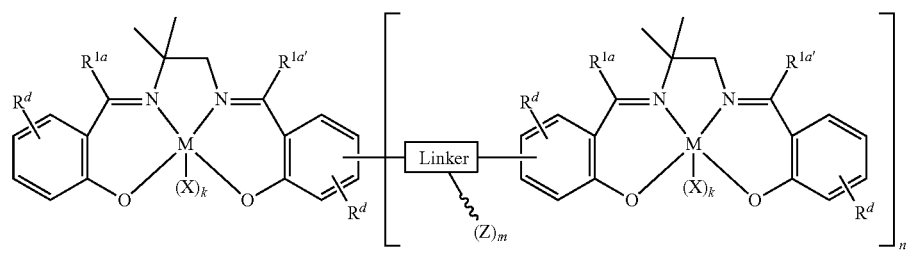

-continued
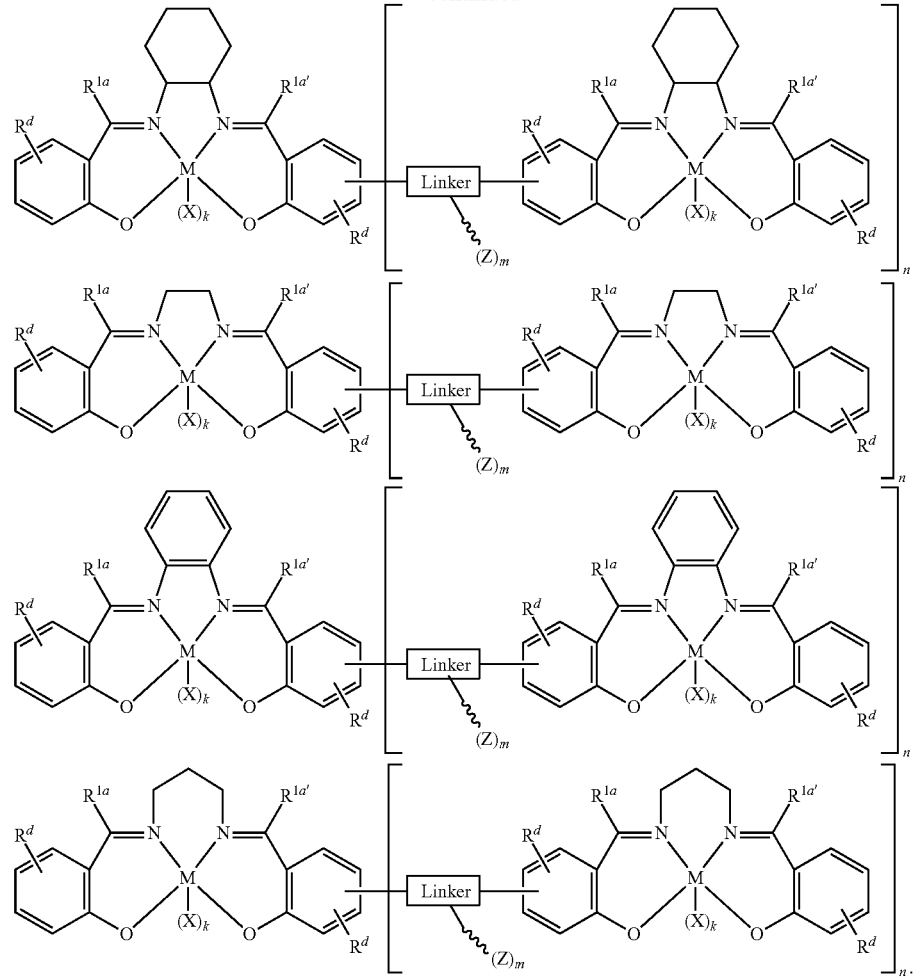
8. The oligomeric complex of claim 3 having a structure selected from the group consisting of:
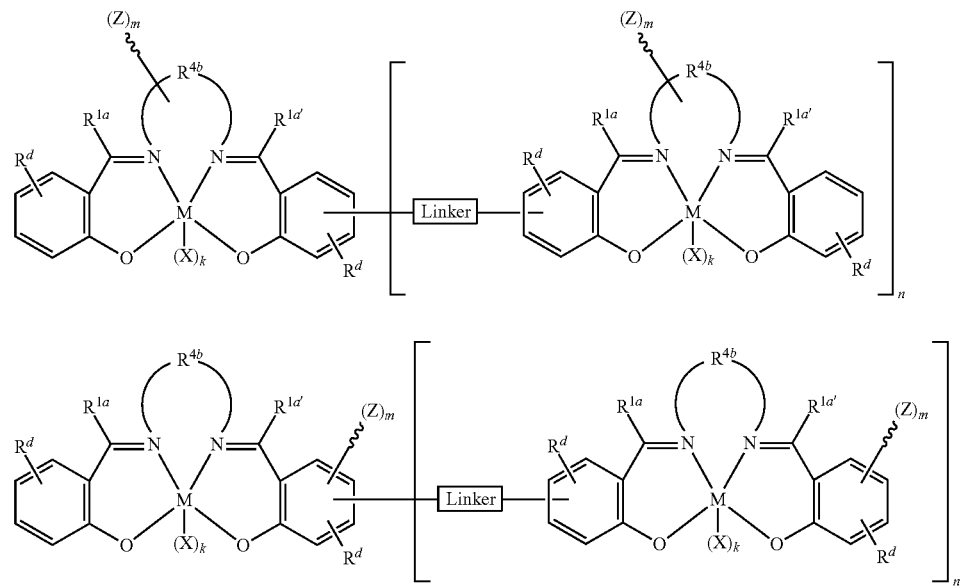

-continued
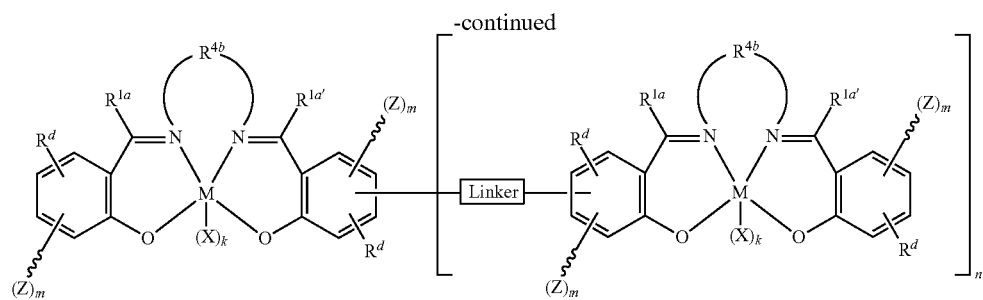
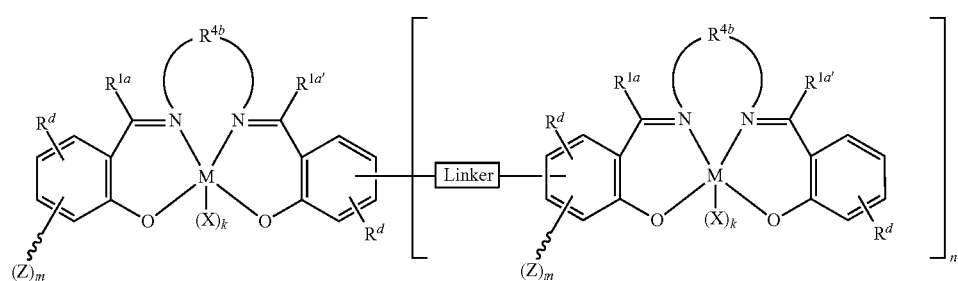
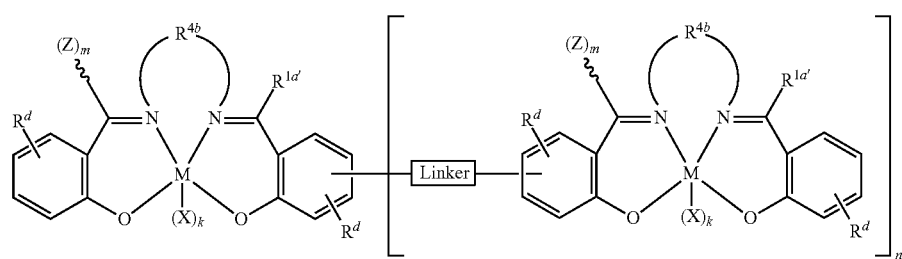
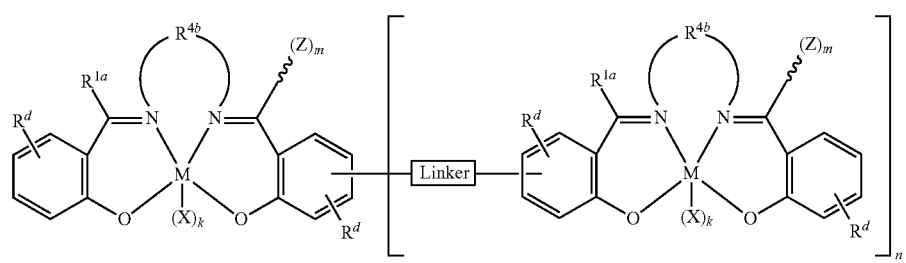
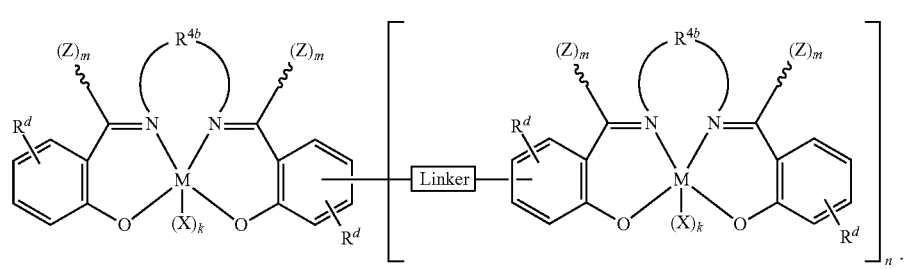

9. The oligomeric complex of claim 3, wherein the repeating units of n are joined to form a cyclic oligomeric complex.
10. The oligomeric complex of claim 9 having a structure selected from the group consisting of:
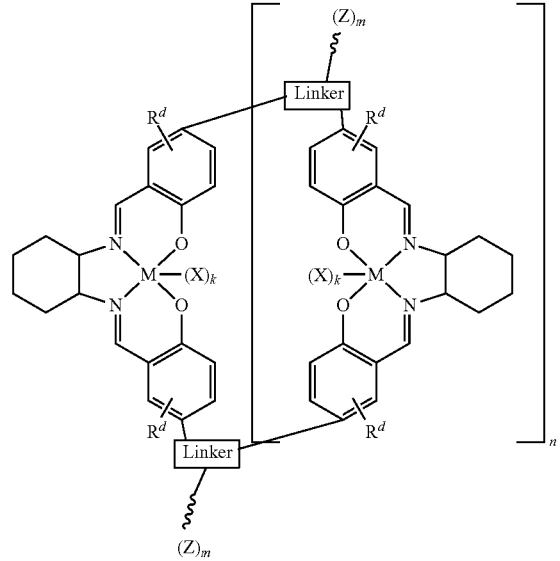
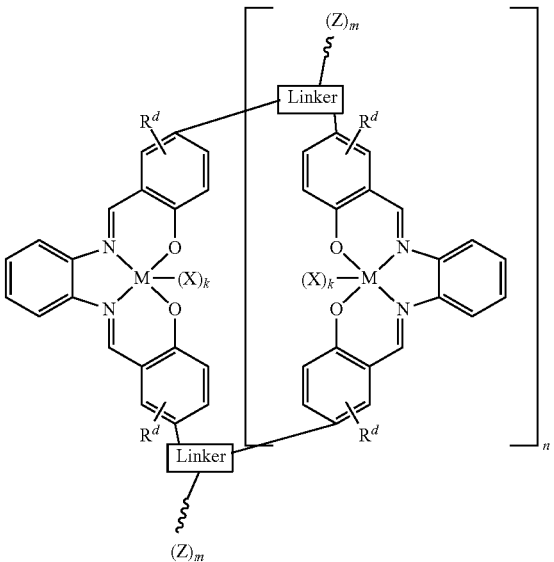
-continued
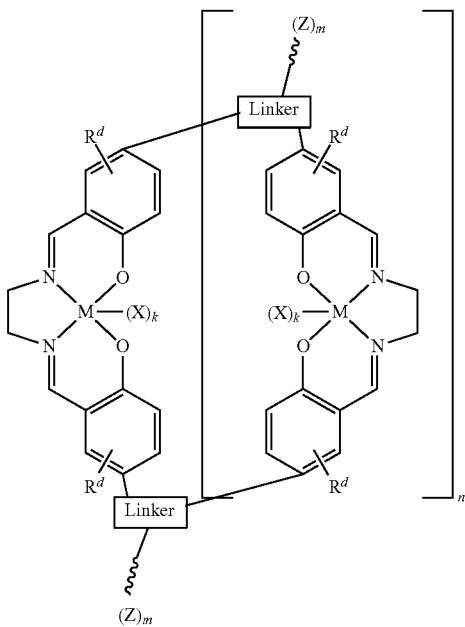
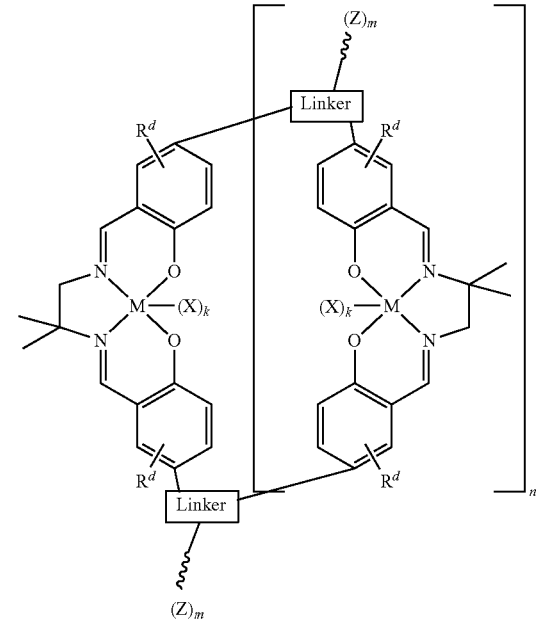

141
-continued
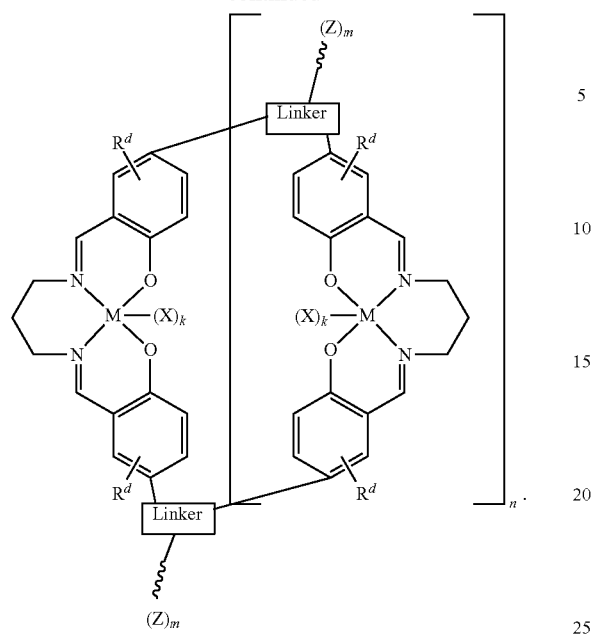
11. The oligomeric complex of claim 9 having a structure selected from the group consisting of:
142
-continued
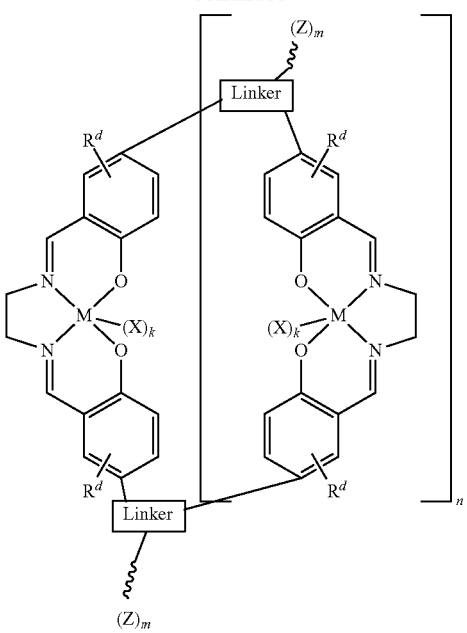
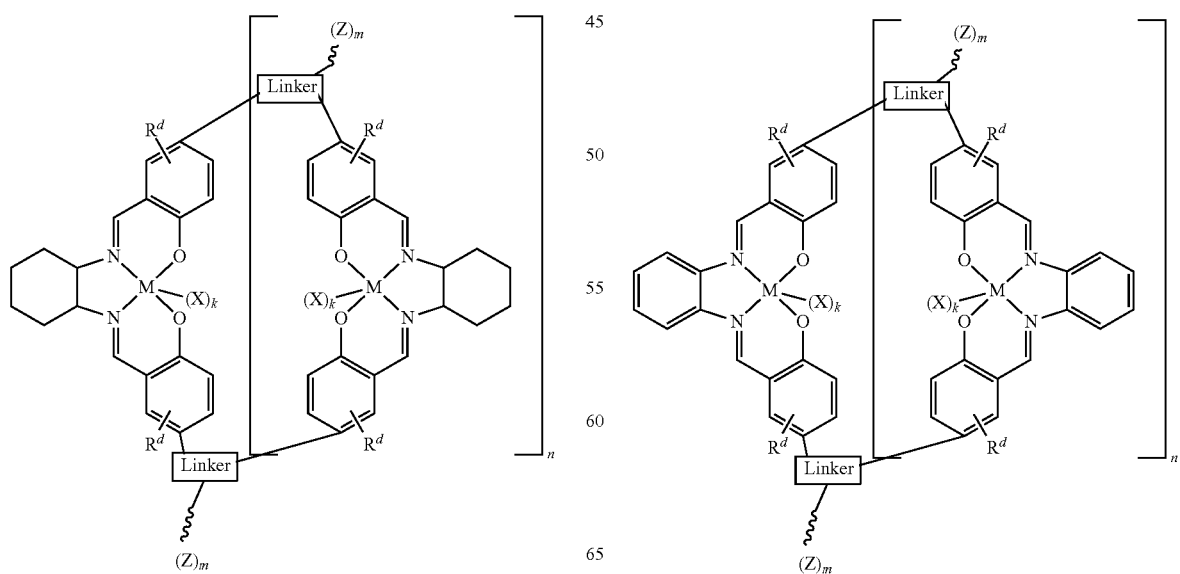

-continued
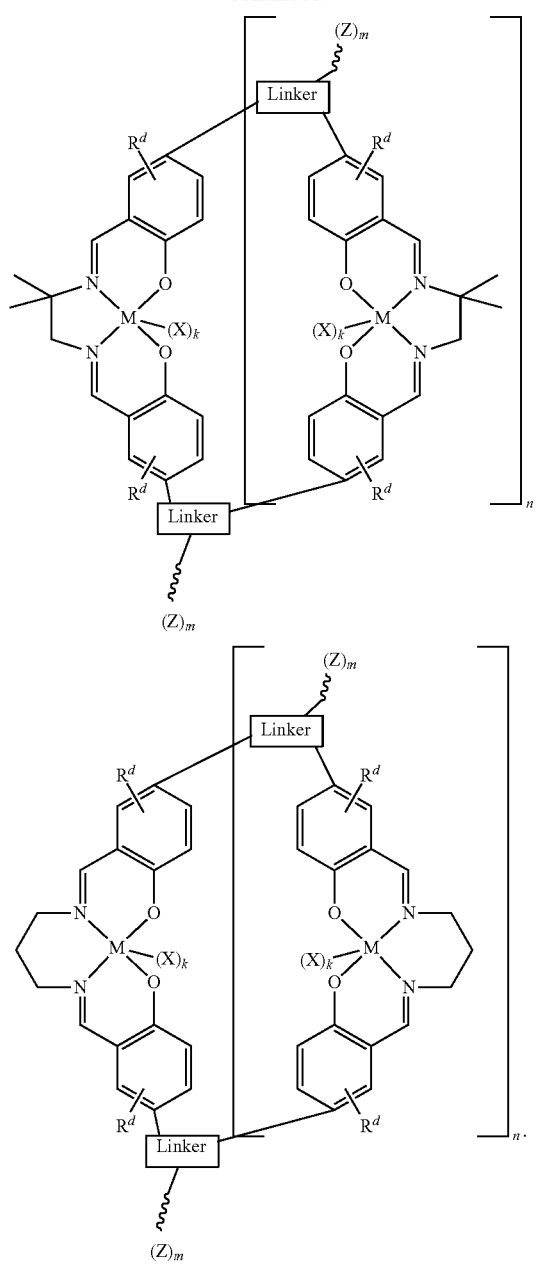
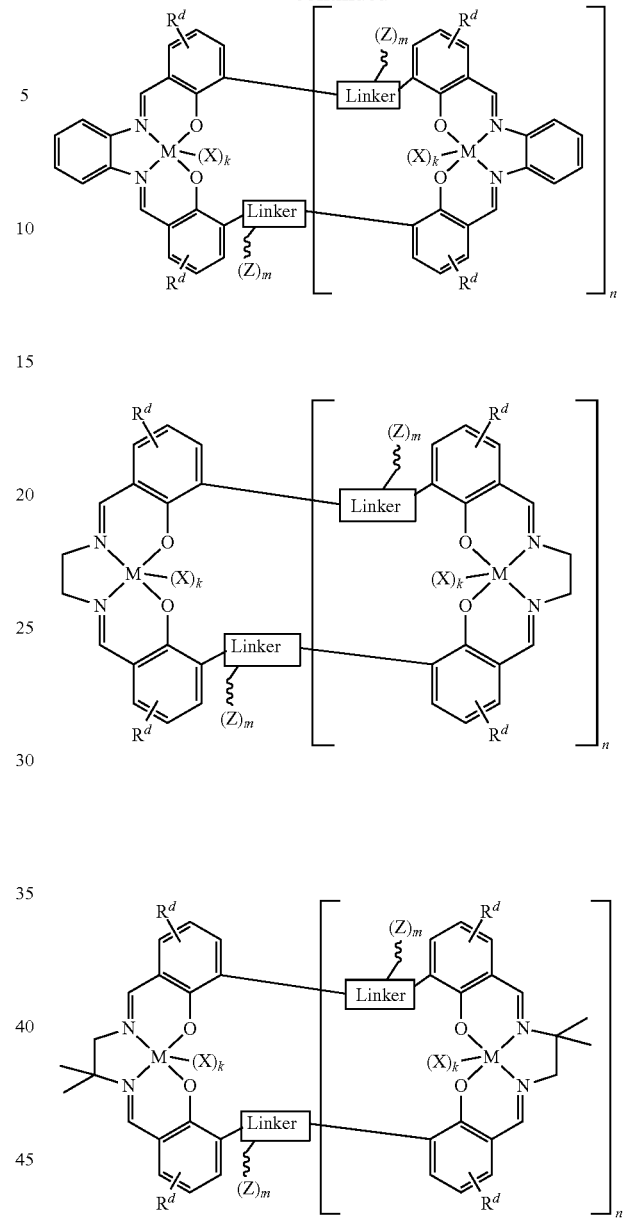
12. The oligomeric complex of claim 9 having a structure selected from the group consisting of:
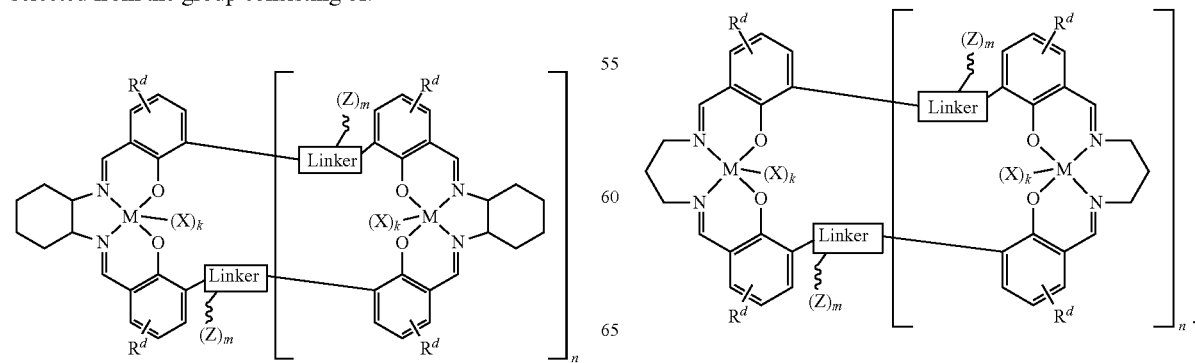

13. The oligomeric complex of claim 9 having a structure selected from the group consisting of:
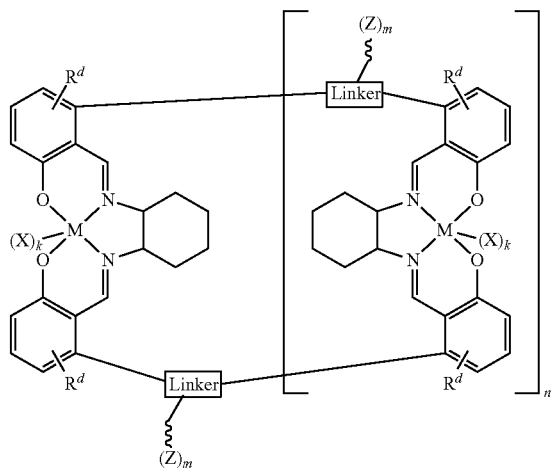
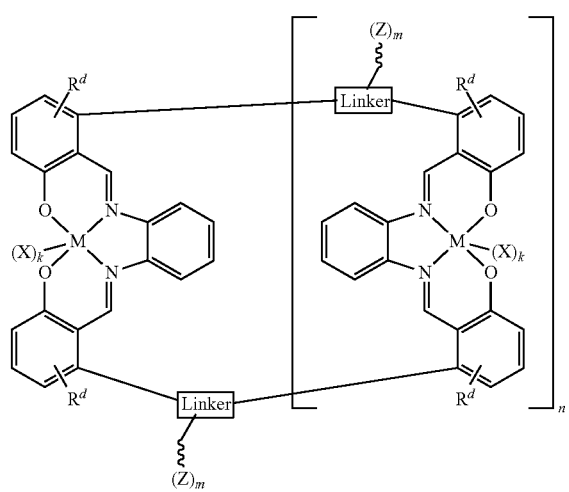
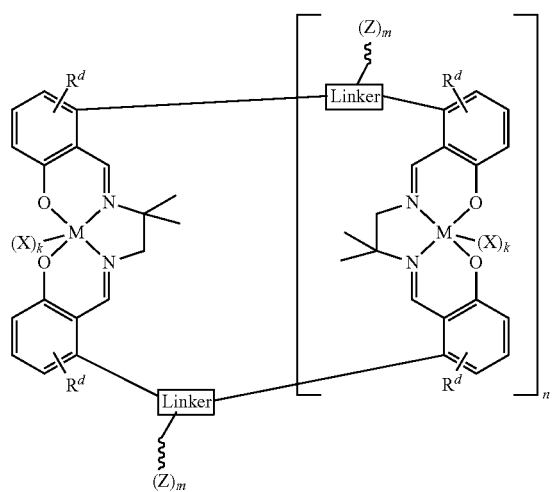
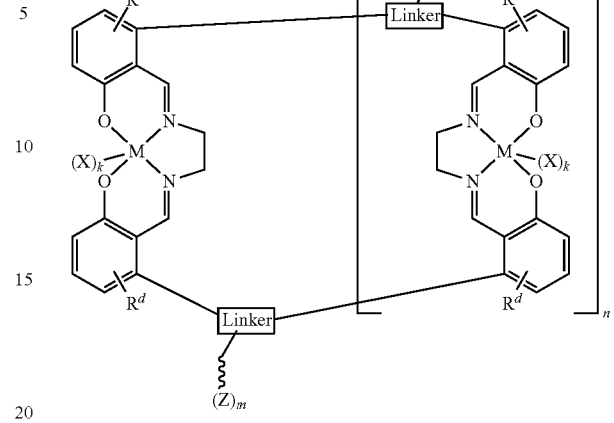
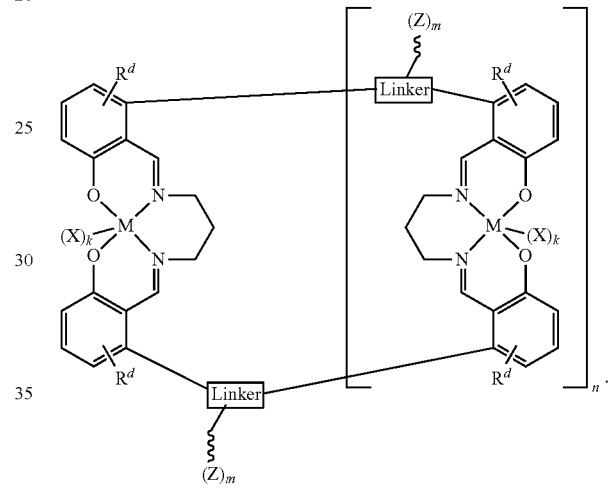
14. The oligomeric complex of claim 1, wherein each Z is independently selected from the group consisting of:
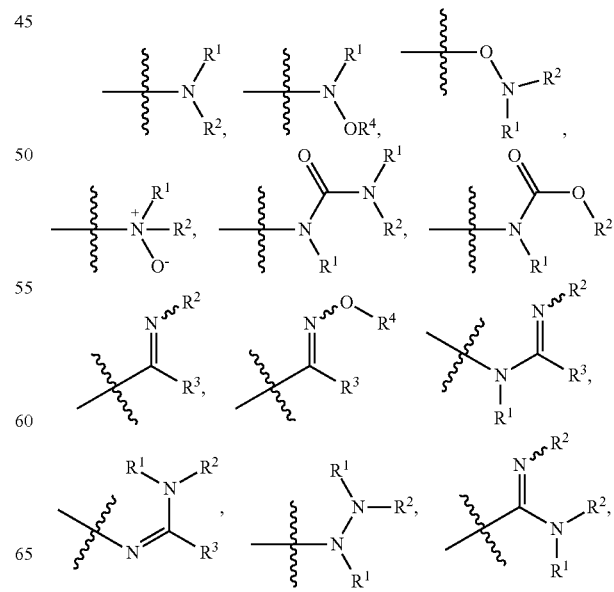

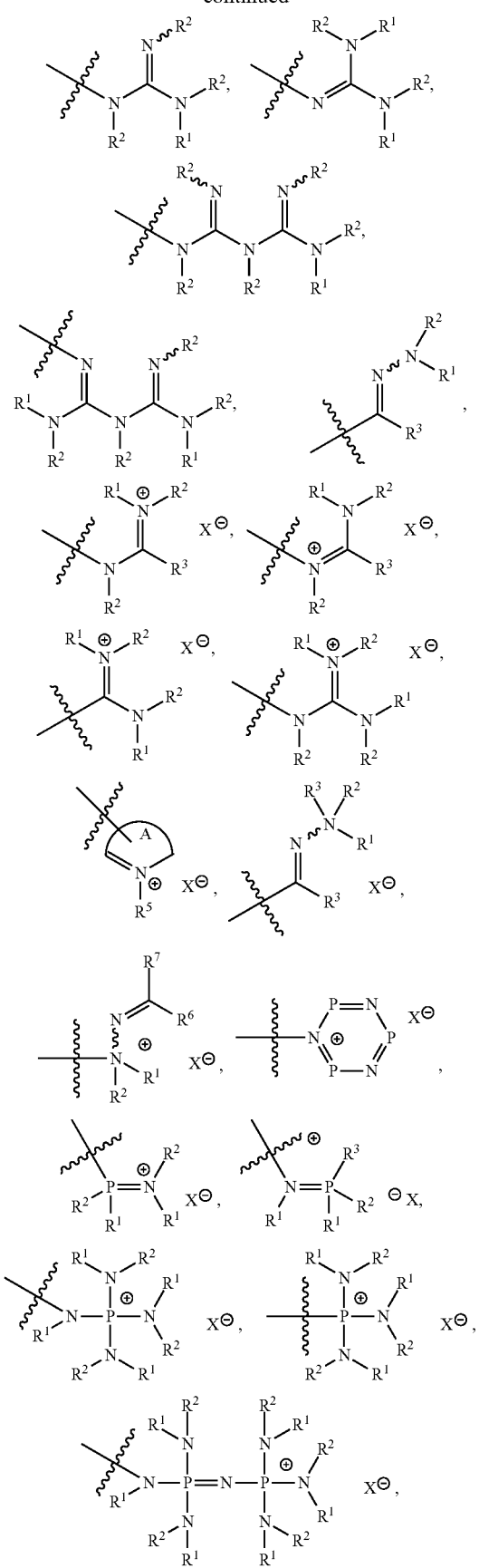
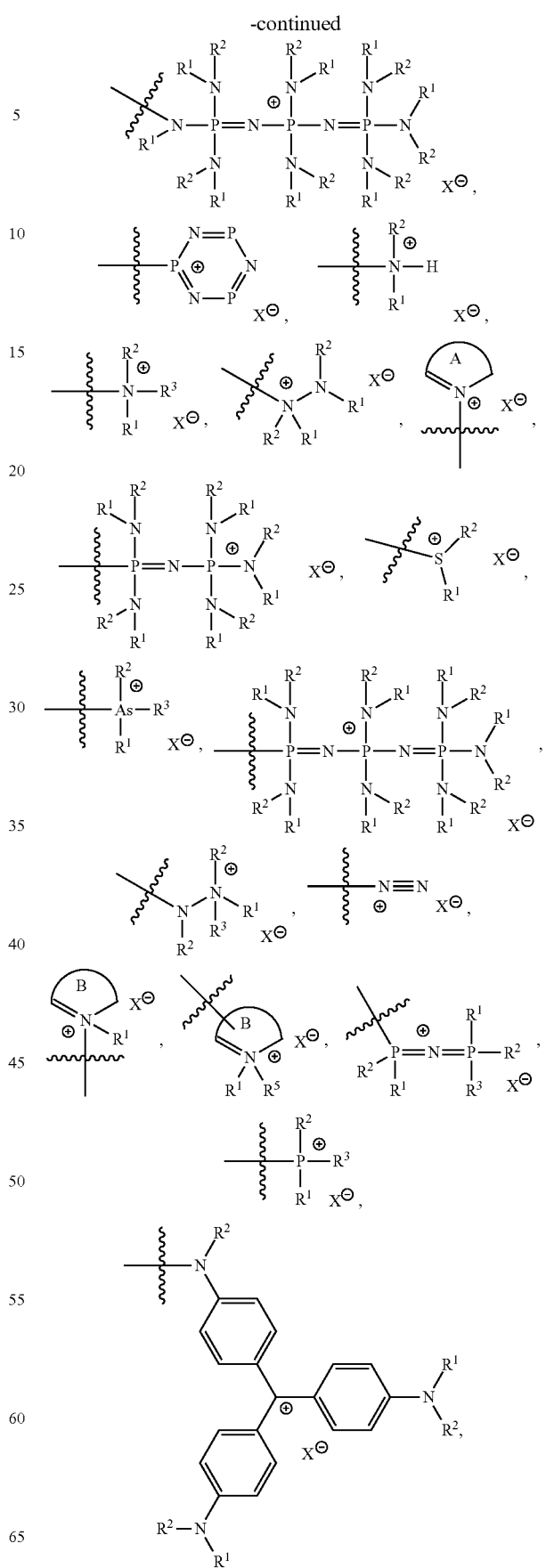

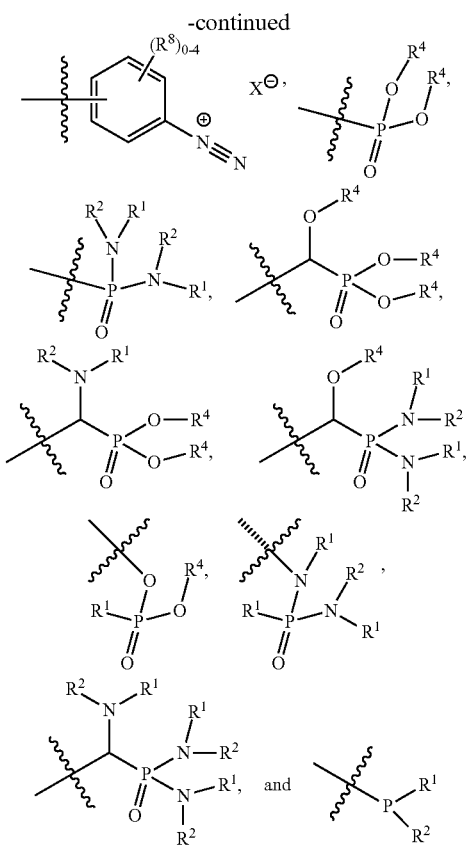

wherein:
each $R^1$ and $R^2$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^1$ and $R^2$ can be taken together with intervening atoms to form one or more optionally substituted rings optionally containing one or more additional heteroatoms;

each $R^3$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^3$ group can be taken with an $R^1$ or $R^2$ group to form one or more optionally substituted rings; and each $R^4$ is independently hydrogen, a hydroxyl protecting group, or an optionally substituted radical selected from the group consisting of $C_{1-20}$ acyl; $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring;

$R^5$ is $R^2$ or hydroxyl; wherein $R^1$ and $R^5$ can be taken together with intervening atoms to form one or more optionally substituted carbocyclic, heterocyclic, aryl, or heteroaryl rings;

each $R^6$ and $R^7$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^6$ and $R^7$ can be taken together with intervening atoms to form one or more optionally substituted rings optionally containing one or more heteroatoms, and an $R^6$ and $R^7$ group can be taken with an $R^1$ or $R^2$ group to form one or more optionally substituted rings;

each occurrence of $R^8$ is independently selected from the group consisting of: halogen, $-NO_2$, $-CN$, $-SR^y$, $-S(O)R^y$, $-S(O)_2R^y$, $-NR^yC(O)R^y$, $-OC(O)R^y$, $-CO_2R^y$, $-NCO$, $-N_3$, $-OR^7$, $-OC(O)N(R^y)_2$, $-N(R^y)_2$, $-NR^YC(O)R^y$, $-NR^yC(O)OR^y$; or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; and where two or more adjacent $R^8$ groups can be taken together to form an optionally substituted saturated, partially unsaturated, or aromatic 5- to 12-membered ring containing 0 to 4 heteroatoms;

$X^-$ is any anion;

Ring A is an optionally substituted, 5- to 10-membered heteroaryl group; and

Ring B is an optionally substituted, 3- to 8-membered saturated or partially unsaturated monocyclic heterocyclic ring having 0-2 heteroatoms in addition to the depicted ring nitrogen atom independently selected from nitrogen, oxygen, or sulfur.

15. The oligomeric complex of claim 1, wherein each M is independently selected from the group consisting of Cr, Mn, V, Fe, Co, Mo, W, Ru, Al, and Ni.

16. The oligomeric complex of claim 1, wherein each M is independently selected from the group consisting of: Co, Al, and Cr.

17. The oligomeric complex of claim 1, wherein M is Co.

18. The oligomeric complex of claim 1, wherein M is Cr.

19. The oligomeric complex of claim 1, wherein M is Al.

20. The oligomeric complex of claim 1, wherein the ⁓ moiety contains 1-30 atoms including at least one carbon atom, and optionally one or more atoms selected from the group consisting of N, O, S, Si, B, and P.

21. The oligomeric complex of claim 1, wherein the ⁓ moiety is a $C_{2-30}$ aliphatic group wherein one or more carbons are optionally and independently replaced by —$NR^y$—, —$N(R^y)C(O)$—, —$C(O)N(R^y)$—, —O—, —C(O)—, —OC(O)—, —C(O)O—, —S—, —$Si(R^y)_2$—, —SO—, —$SO_2$—, —C(=S)—, —C(=$NR^y$)—, or —N=N—, wherein each occurrence of $R^y$ is independently —H, or an optionally substituted radical selected from the group consisting of $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, a 5-6 membered heteroaryl ring having 1-3 heteroatoms independently selected from nitrogen, oxygen, or sulfur, and 8- to 10-membered aryl.

22. The oligomeric complex of claim 21, wherein the ⁓ moiety is selected from the group consisting of:

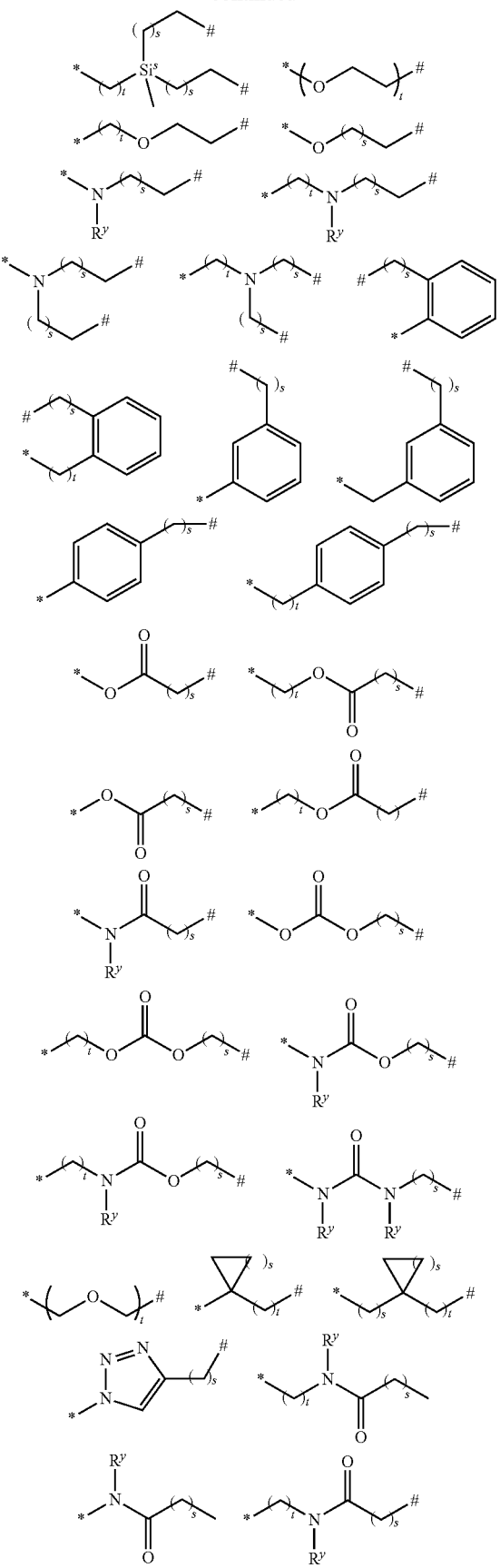

153

-continued

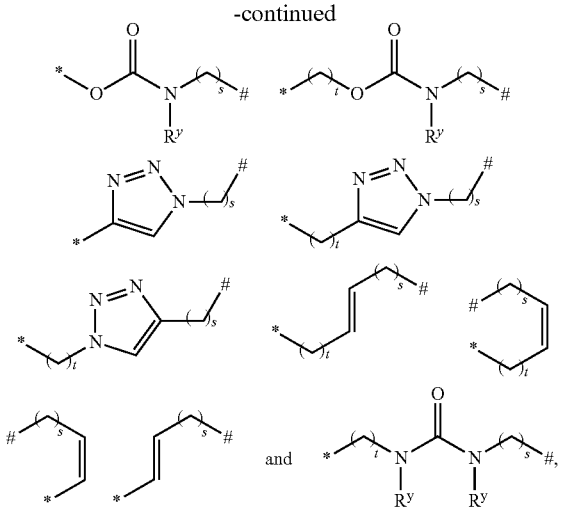

and wherein each s is independently 0-6, t is 0-4, * represents the site of attachment to a ligand, and each # represents a site of attachment of an activating functional group.

23. The oligomeric complex of claim 1, wherein one or more Z group is independently a neutral functional group selected from the group consisting of amines, phosphines, guanidines, bis-guanidines, amidines, and nitrogen-containing heterocycles.

24. The oligomeric complex of claim 1, wherein X is selected from the group consisting of: chlorine, bromine, an optionally substituted $C_{1-12}$ carboxylate, azide, an optionally substituted phenoxide, a sulfonate salt, and a combination of any two or more of these.

25. The oligomeric complex of claim 1, wherein X is selected from the group consisting of chloride, acetate, trifluoroacetate, azide, pentafluorobenzoate, and a nitrophenolate.

26. The oligomeric complex of claim 14, wherein at least one Z group is selected from the group consisting of:

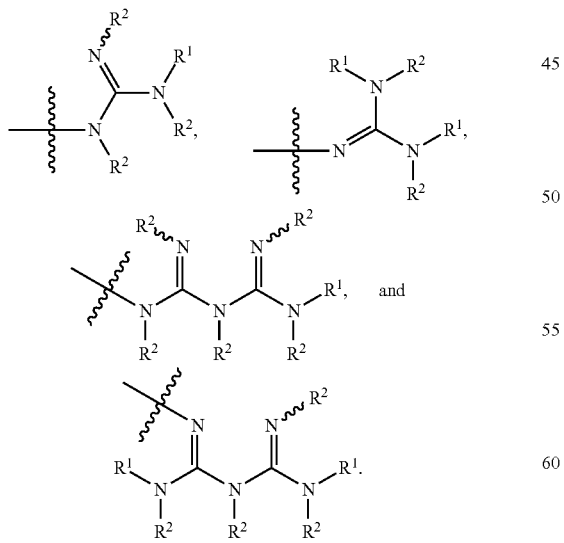

27. The oligomeric complex of claim 26, wherein each $R^1$ and $R^2$ is independently —H or optionally substituted $C_{1-20}$ aliphatic.

154

28. The oligomeric complex of claim 26, wherein each $R^1$ and $R^2$ is independently —H or optionally substituted $C_{1-10}$ aliphatic.

29. The oligomeric complex of claim 26, wherein two or more of $R^1$ and $R^2$ are taken together to form one or more optionally substituted rings optionally containing additional heteroatoms.

30. The oligomeric complex of claim 1, wherein at least one Z group is selected from the group consisting of:

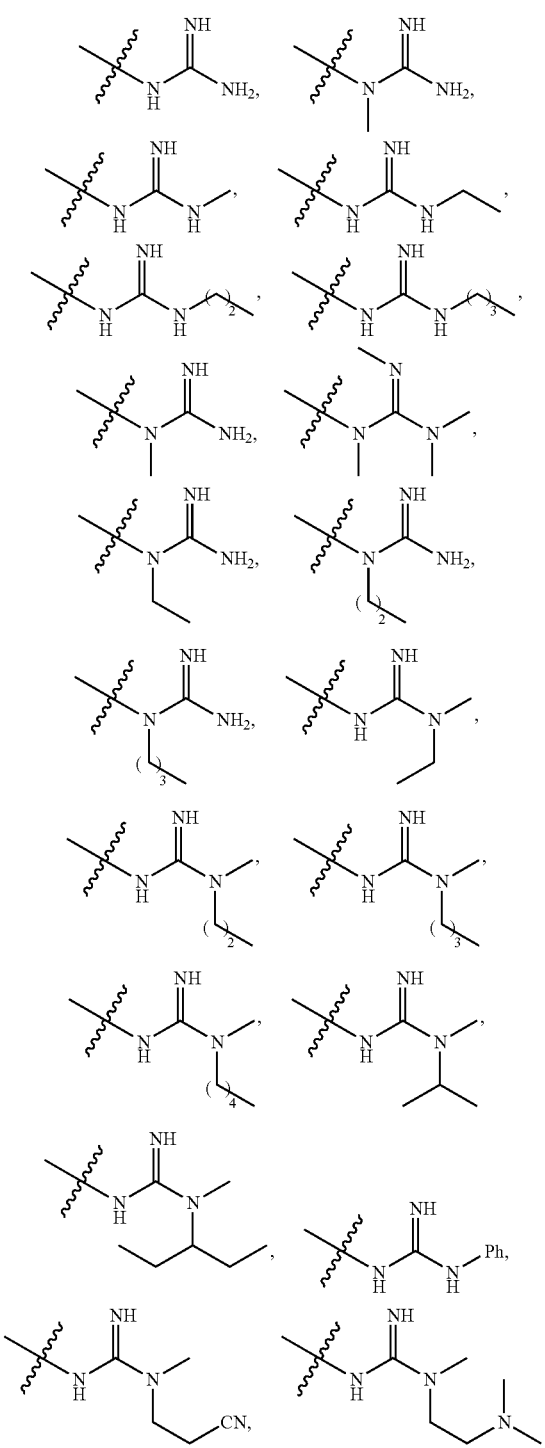

-continued

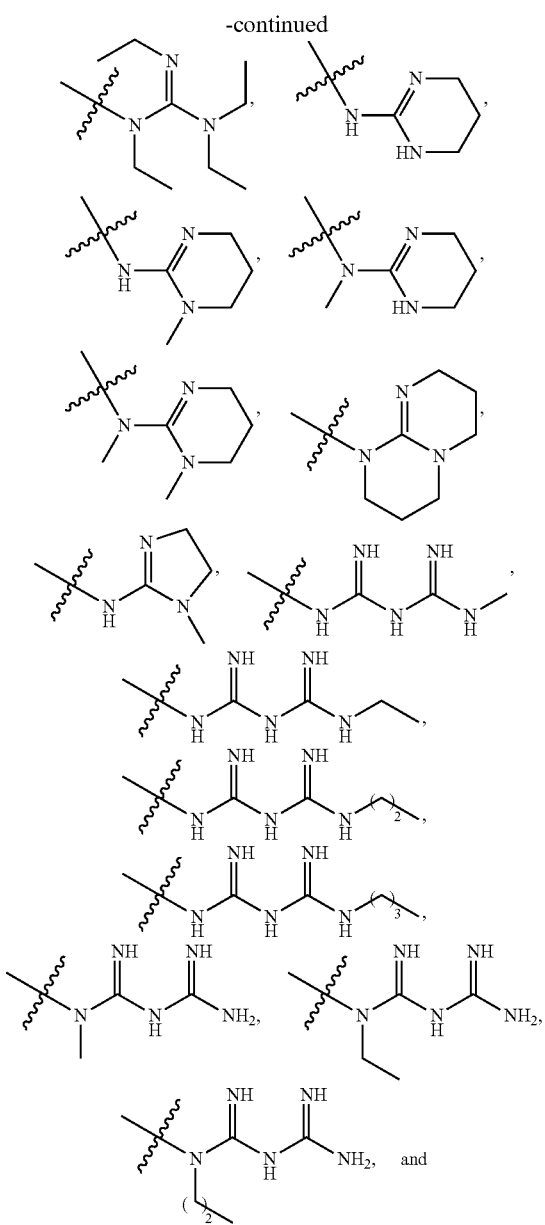

-continued

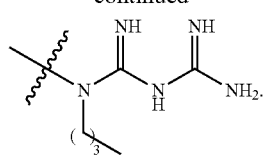

31. The oligomeric complex of claim 14, wherein at least one Z group is

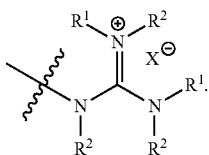

32. The oligomeric complex of claim 31, wherein each $R^1$ and $R^2$ is independently —H or optionally substituted $C_{1-20}$ aliphatic.

33. The oligomeric complex of claim 31, wherein each $R^1$ and $R^2$ is independently —H or optionally substituted $C_{1-10}$ aliphatic.

34. The oligomeric complex of claim 31, wherein two or more of $R^1$ and $R^2$ are taken together to form one or more optionally substituted rings optionally containing additional heteroatoms.

35. The oligomeric complex of claim 1, wherein n is from 1 to 20.

36. The oligomeric complex of claim 35, wherein n is from 1 to 10.

37. The oligomeric complex of claim 35, wherein n is from 2 to 10.

38. The oligomeric complex of claim 35, wherein n is from 2 to 6.

39. The oligomeric complex of claim 35, wherein n is from 1 to 5.

40. A method comprising the step of contacting an epoxide and carbon dioxide with an oligomeric complex of claim 1.

* * * * *